(12) United States Patent
Seliktar et al.

(10) Patent No.: US 12,678,541 B2
(45) Date of Patent: Jul. 14, 2026

(54) CURABLE FIBRINOGEN AND USES THEREOF

(71) Applicant: Technion Research & Development Foundation Limited, Haifa (IL)

(72) Inventors: Dror Seliktar, Haifa (IL); Haneen Simaan-Yameen, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 813 days.

(21) Appl. No.: 17/961,658

(22) Filed: Oct. 7, 2022

(65) Prior Publication Data

US 2023/0113487 A1 Apr. 13, 2023

Related U.S. Application Data

(60) Provisional application No. 63/253,191, filed on Oct. 7, 2021.

(51) Int. Cl.
*A61L 27/48* (2006.01)
*A61L 27/52* (2006.01)

(52) U.S. Cl.
CPC .............. *A61L 27/48* (2013.01); *A61L 27/52* (2013.01)

(58) Field of Classification Search
None
See application file for complete search history.

(56) References Cited

FOREIGN PATENT DOCUMENTS

| | | | | |
|---|---|---|---|---|
| WO | WO 2005/061018 | 7/2005 | | |
| WO | WO 2008/126092 | 10/2008 | | |
| WO | WO 2011/073991 | 6/2011 | | |
| WO | WO 2014/207749 | 12/2014 | | |
| WO | WO-2018225076 A1 * | 12/2018 | ............. | A61L 27/24 |
| WO | WO 2018/225076 | 8/2021 | | |

OTHER PUBLICATIONS

Almany et al. "Biosynthetic Hydrogel Scaffolds Made From Fibrogen and Polyethylene Glycol for 3D Cell Cultures", Biomaterials, 26(15): 2467-2477, Available Online Aug. 20, 2004.

Drzewiecki et al. "Methacrylation Induces Rapid, Temperature-Dependent, Reversible Self-Assembly of Type I Collagen", Langmuir, 30(37): 11204-11211, Aug. 28, 2014.

Gaudet et al. "Characterization of Methacrylated Type-I Collagen as A Dynamic, Photoactive Hydrogel", Biointerphases, 7(1-4): 25-1-25-9 , Published Online Mar. 10, 2012.

Goldshmid et al. "Steric Interference of Adhesion Supports In-Vitro Chondrogenesis of Mesenchymal Stem Cells on Hydrogels for Cartilage Repair", Scientific Reports, 5(1): 12607-1-12607-, Sep. 28, 2015.

Isaacson et al. "3D Bioprinting of A Corneal Stroma Equivalent", Experimental Eye Research, 173: 188-193, Published Online May 30, 2018.

Miller et al. "Editorial: Special Issue on 3D Printing of Biomaterials", ACS Biomaterials Science & Engineering, 2(10): 1658-1661,Oct. 10, 2016.

Murphy et al. "3D Bioprinting of Tissues and Organs", Nature Biotechnology, 32(8): 773-785, Published Online Aug. 5, 2014.

Ouyang et al. "Expanding and Optimizing 3D Bioprinting Capabilities Using Complementary Networks Bioinks", Science Advances, 6: eabc5529-1 eabc5529-13, Sep. 18, 2020.

Seliktar "Designing Cell-Compatible Hydrogels for Biomedical Applications", Science, 336(6085): 1124-1128, Jun. 1, 2012.

Tibbitt et al. "Hydrogels as Aextracellular Matrix Mimics for 3D Cell Culture", Biotechnology and Bioengineering, 103(4): 655-663, Published Online Apr. 13, 2009.

* cited by examiner

*Primary Examiner* — Sergio Coffa

(57) ABSTRACT

Conjugates of fibrinogen and a plurality of curable groups covalently attached thereto, and curable formulations comprising such conjugates, are provided. Also provided are three-dimensional objects (scaffolds) made of the conjugate or the curable formulation, for example, by additive manufacturing, and uses thereof in, for example, tissue healing and/or regeneration.

Figure 3A:
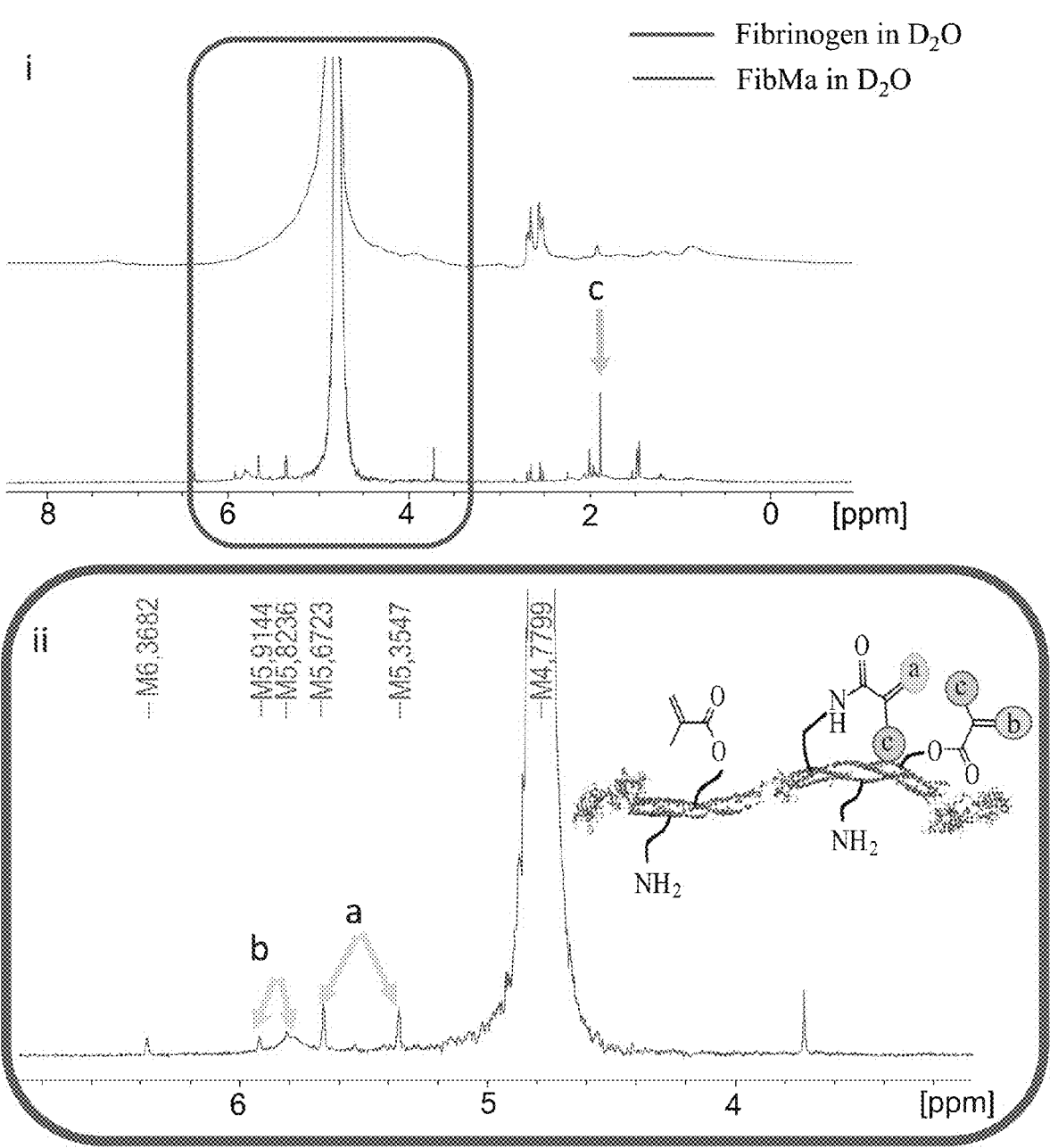

15 Claims, 32 Drawing Sheets
(29 of 32 Drawing Sheet(s) Filed in Color)

*The amino acid composition of the polypeptide chains of fibrinogen and fibrin*

| Amino acid | Fibrinogen (residues per molecule) | | | Fibrin (residues per molecule) | | |
|---|---|---|---|---|---|---|
| | α-Chain | β-Chain | γ-Chain | α-Polymer | β-Chain | γ-Dimer |
| Lysine | 33.2 | 34.1 | 35.4 | 42.5 | 35.6 | 37.1 |
| Histidine | 15.5 | 8.2 | 9.0 | 15.8 | 7.9 | 9.6 |
| Arginine | 32.9 | 23.6 | 10.3 | 37.6 | 26.3 | 11.3 |
| Aspartic acid | 74.7 | 58.1 | 63.9 | 64.0 | 59.2 | 58.6 |
| Threonine | 53.9 | 28.1 | 33.1 | 54.6 | 26.8 | 36.1 |
| Serine | 87.4 | 34.8 | 27.0 | 69.2 | 33.4 | 29.8 |
| Glutamic acid | 75.1 | 67.8 | 55.4 | 70.4 | 61.0 | 54.6 |
| Proline | 49.9 | 33.4 | 20.4 | 44.9 | 36.3 | 24.3 |
| Glycine | 79.5 | 52.4 | 42.5 | 73.6 | 47.0 | 42.5 |
| Alanine | 26.3 | 27.8 | 30.7 | 28.7 | 27.5 | 30.3 |
| Valine | 27.6 | 24.5 | 16.0 | 30.7 | 26.1 | 16.4 |
| Isoleucine | 15.8 | 15.6 | 23.5 | 21.1 | 16.5 | 22.3 |
| Leucine | 36.1 | 33.9 | 32.5 | 37.2 | 34.3 | 30.7 |
| Tyrosine | 11.7 | 21.9 | 22.5 | 15.4 | 22.1 | 21.2 |
| Phenylalanine | 17.9 | 11.6 | 19.8 | 22.2 | 12.6 | 20.8 |

FIG. 1

Fibrinogen          FibMA          Methacrylic acid

FIG. 2A

FIG. 2B

Amplitude Sweep Test

Frequency Sweep Test

Fibrinogen

FibMA$_{0.4\%}$ and PEG-TA solution

FibMA$_{0.4\%}$ and PEG-TA hydrogel

Day 1                    Day 5                    Day 14                    Day 20

Day 2                    Day 7                    Day 10

FibMA and
PEG-TA

Tissue Construct Beads: Tissue
beads with MDA-MB-231 (Mcherry)
and NHDF-GFP cells

*UV light*

MDA-MB-231
NHDF
FibMA
PF

FibMA$_{0.4\%}$ and PEG-DA

FibMA$_{0.4\%}$ and PEG-TA

FibMA$_{0.4\%}$ and PEG-OA 1.2% PEG-TA 1.6% PEG-TA

2% PEG-TA

FIG. 23A          FIG. 23B          FIG. 23C
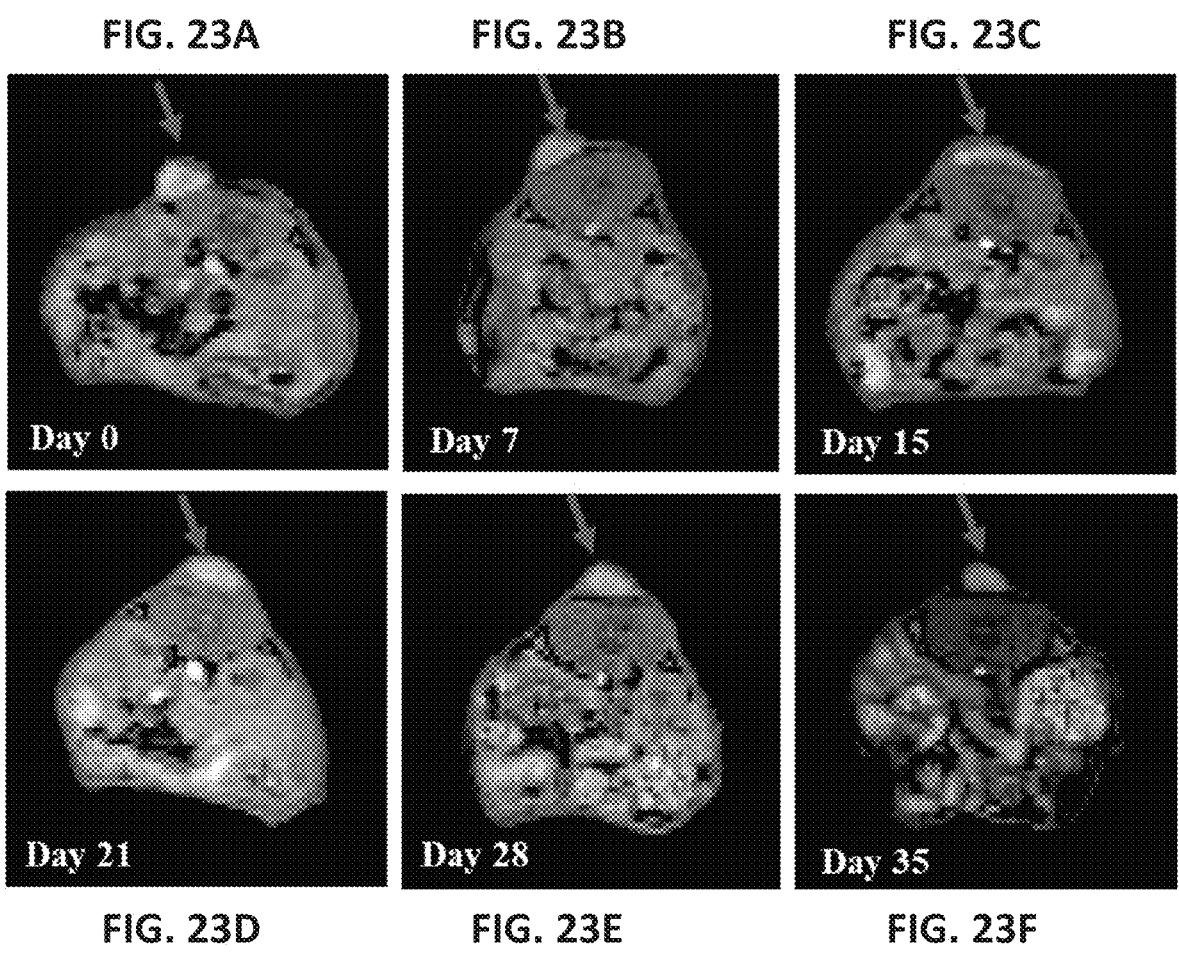
FIG. 23D          FIG. 23E          FIG. 23F
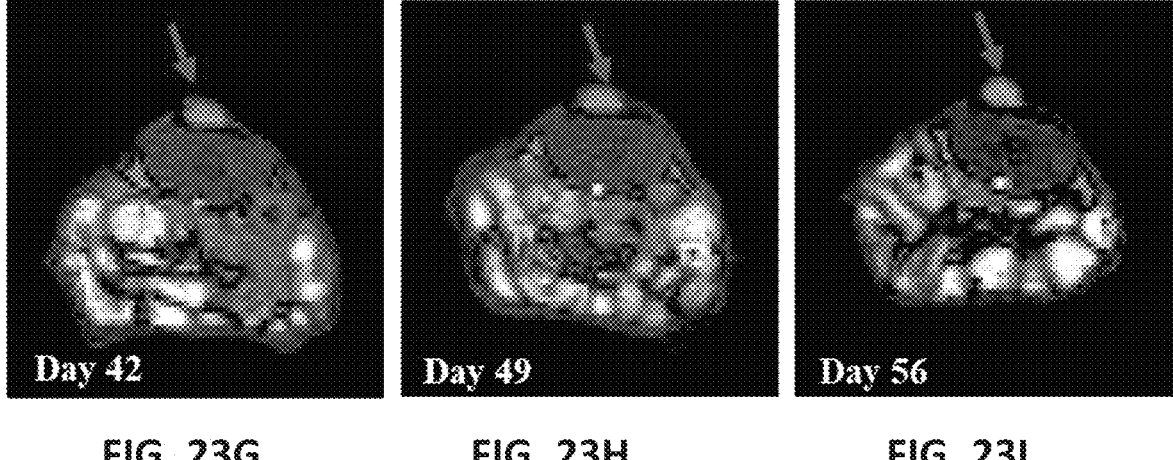
FIG. 23G          FIG. 23H          FIG. 23I 400 μm 500 μm 500 μm FibMA$_{0.2\%}$ 10mg/ml FibMA$_{0.2\%}$ 40 mg/ml

CURABLE FIBRINOGEN AND USES THEREOF

RELATED APPLICATION(S)

This application claims the benefit of priority under 35 USC § 119(e) of U.S. Provisional Patent Application No. 63/253,191 filed on Oct. 7, 2021, the contents of which are all incorporated by reference as if fully set forth herein in their entirety.

FIELD AND BACKGROUND OF THE INVENTION

The present invention, in some embodiments thereof, relates to biological materials and, more particularly, but not exclusively, to a curable fibrinogen, to curable formulations containing same, to scaffolds formed therefrom and to uses of curable fibrinogen, curable formulation and/or scaffold in, for example, tissue healing and/or regeneration.

Hydrogel biomaterials that are biodegradable are often sought in the field of regenerative medicine and 3D bioprinting. Biomedical hydrogels comprised of natural polymers such as chitosan, alginate, gelatin, albumin, fibrin and collagen have gained much research interest for their inherent biocompatibility and high permeability for water-soluble nutrients and metabolites [see, for example, Antoine et. al., *Tissue Engineering—Part B: Reviews.* 2014; Azab, A. K., et al., *Crosslinked chitosan implants as potential degradable devices for brachytherapy: In vitro and in vivo analysis.* Journal of Controlled Release, 2006; Barralet, J. E., et al., *Comparison of bone marrow cell growth on 2D and 3D alginate hydrogels, in Journal of Materials Science: Materials in Medicine.* 2005; Eyrich, D., et al., *Long-term stable fibrin gels for cartilage engineering.* Biomaterials, 2007]. Although these traits are indispensable in biomedical applications [Taghipour, Y. D., et al., Current Medicinal Chemistry, 2020. 27(16): p. 2658-2680], these hydrogels often lack sufficient mechanical strength, and their mechanical properties are not easily controlled.

Synthetic polymers such as poly(vinyl alcohol) (PVA), poly(2-hydroxy ethyl methacrylate (PHEMA) and poly(ethylene oxide) (PEO) provide a well-defined and stable structure that is highly-controllable and tunable. However, these properties are not sufficient in promoting cell functionality, which is key in biological and biomedical applications.

Much effort is directed towards designing biological and synthetic hybrid hydrogels that will enable structural stability, physical control, and biological functionality. By providing cells/tissues with a hydrogel environment having well-defined biological and mechanical properties, one can design materials that guide natural cell processes such as morphogenesis, cell migration, cell differentiation and cell adhesion. See, for example, Almany, L. and D. Seliktar, *Biosynthetic hydro gel scaffolds made from fibrinogen and polyethylene glycol for 3D cell cultures.* Biomaterials, 2005. 26(15): p. 2467-2477].

Among the numerous examples of biosynthetic biomaterials which are highly suitable for working with cells and tissues, there is a class of hydrogels made from polyethylene glycol (PEG) adducts which excel in biomedical applications [Gonen-Wadmany et al., Biomaterials, 2011. 32(26): p. 6025-6033]. PEG is inert to most biological molecules such as proteins, it is non-toxic, non-immunogenic and has the advantage of being FDA approved for various clinical indications. Adducts such as PEG-chitosan, PEG-heparin, PEG-collagen, and PEG-fibrinogen were successfully employed for various biomedical applications, including orthopedic, muscle and nerve repair. PEG-fibrinogen for example, was successfully applied as a regenerative matrix for the repair of focal cartilage defects [Goldshmid, R., et al., Scientific Reports, 2015. 5].

Although progress has been made in the biomedical use of biosynthetic materials [See, for example, Lev, R. and D. Seliktar, *Hydrogel biomaterials and their therapeutic potential for muscle injuries and muscular dystrophies.* Journal of the Royal Society Interface, 2018. 15(138)], many of the new biomaterials still lack injectability for their in vivo administration. Often, injectability of biosynthetic materials requires additional functionalization of the polymer to enable a rapid in situ crosslinking. In this context, the reaction kinetics should be on the scale of seconds to enable proper stabilization of the materials upon in vivo placement.

Certain naturally occurring biological materials have an innate capability to undergo this rapid in situ crosslinking, including, for example, alginate with the divalent cationic cross-linker calcium and fibrinogen with enzymatic modifications (e.g., transglutaminase factor VIII) [Ahmad, E., et al., International Journal of Biological Macromolecules, 2015. 81: p. 121-136; Ahmed et al. Tissue Engineering Part B-Reviews, 2008. 14(2): p. 199-215]. Other biologically-derived materials such as gelatin can be cross-linked using small concentrations of exogenous sodium tetraborate (borax) to give injectability to this system.

With the advent of biosynthetic materials, injectability needs to be engineered into the polymer backbone because the bioprocessing of the biological constituents can substantially reduce their innate crosslinking ability. For these reasons, polymer engineering paradigms have been applied to control the crosslinking towards rapid and cell-compatible in situ hydrogel formation [Seliktar, D., Designing Cell-Compatible Hydrogels for Biomedical Applications. Science, 2012. 336(6085): p. 1124-1128].

Injectable biomaterials are gaining importance not only because they provide an easy route for in vivo administration with minimal invasiveness, they also can be used for 3D bioprinting [See, for example, Ouyang, L. L., et al., *Expanding and optimizing 3D bioprinting capabilities using complementary network bioinks.* Science Advances, 2020. 6(38)].

In this context, bioprinting is the additive manufacturing process of living cells and biomaterials toward the development of three-dimensional constructs with biomimetic structure and function. The basic design concepts that enable injectability of biomaterials is premised on a controlled transition from a viscous fluid to an elastic gel. Such phase transitions are rather straightforward in materials science, but challenges arise when cells are present in the materials during this transition.

Most advances in the design of injectable biomaterials have been made on hydrophilic gels; these are biomaterials that are comprised of hydrophilic polymers and contain large amounts of water [Seliktar, D., *Designing Cell-Compatible Hydrogels for Biomedical Applications.* Science, 2012. 336(6085): p. 1124-1128]. The crosslinked hydrogel network structure is comprised of hydrophilic groups attached to a polymeric backbone, which enable retaining a high water content while maintaining their chemical and mechanical integrity. In addition, their 3D nature makes them an excellent platform for studying cell-cell interactions, cell functionality and cell response to intrinsic as well as extrinsic factors [Tibbitt, M. W. and K. S. Anseth, *Hydrogels as extracellular matrix mimics for* 3D cell culture, in Biotechnology and Bioengineering. 2009].

Additive manufacturing (AM) is generally a process in which a three-dimensional (3D) object is manufactured utilizing a computer model of the objects. The basic operation of any AM system consists of slicing a three-dimensional computer model into thin cross sections, translating the result into two-dimensional position data and feeding the data to control equipment which manufacture a three-dimensional structure in a layerwise manner.

Various AM technologies exist, amongst which are stereolithography, digital light processing (DLP), and three-dimensional (3D) printing such as 3D inkjet printing. Such techniques are generally performed with layer by layer deposition and hardening (e.g., solidification) of one or more building materials, which typically include photopolymerizable (photocurable) materials.

Stereolithography, for example, is an additive manufacturing process which employs a liquid ultraviolet (UV)-curable building material and a UV laser. In such a process, for each dispensed layer of the building material, the laser beam traces a cross-section of the part pattern on the surface of the dispensed liquid building material. Exposure to the UV laser light cures and solidifies the pattern traced on the building material and joins it to the layer below. After being built, the formed parts are immersed in a chemical bath in order to be cleaned of excess building material and are subsequently cured in a UV oven.

In three-dimensional printing processes, for example, a building material is dispensed from a dispensing head having a set of nozzles to deposit layers on a supporting structure. Depending on the building material, the layers may then be cured or solidified using a suitable device.

The building materials may include modeling material formulation(s) and support material formulation(s), which form, upon hardening, the object and the temporary support constructions supporting the object as it is being built, respectively.

The modeling material formulation(s) is/are deposited to produce the desired object and the support material formulation(s) is/are used, with or without modeling material elements, to provide support structures for specific areas of the object during building and assure adequate vertical placement of subsequent object layers, e.g., in cases where objects include overhanging features or shapes such as curved geometries, negative angles, voids, and so on.

Both the modeling and support materials are preferably liquid at the working temperature at which they are dispensed, and subsequently hardened, typically upon exposure to hardening or curing condition such as curing energy (e.g., UV curing), to form the required layer shape. After printing completion, support structures, if present, are removed to reveal the final shape of the fabricated 3D object. The hardening (curing) of the dispensed materials typically involves polymerization (e.g., photopolymerization) and/or crosslinking (e.g., photocrosslinking).

Additive manufacturing has been first used in biological applications for forming three-dimensional sacrificial resin molds in which 3D scaffolds from biological materials were created.

3D bioprinting is an additive manufacturing methodology which uses biological materials, optionally in combination with chemicals and/or cells, which are printed layer-by-layer with a precise positioning and a tight control of functional components placement to create a 3D structure.

Three dimensional (3D) bioprinting is gaining momentum in many medicinal applications, especially in regenerative medicine, to address the need for complex scaffolds, tissues and organs suitable for transplantation.

Inherent to 3D printing in general is that the mechanical properties of the printing media (the dispensed building material) are very different from the post-printed cured (hardened) material.

To allow tight control on the curing (e.g., polymerization) after printing, the building material commonly includes polymerizable (e.g., photopolymerizable) moieties or groups that polymerize (e.g., by chain elongation and/or cross-linking) upon being dispensed, to preserve the geometric shape and provide the necessary physical properties of the final product.

Different technologies have been developed for 3D bioprinting, including 3D Inkjet printing, Extrusion printing, Laser-assisted printing and Projection stereolithography [see, for example, Murphy S V, Atala A, Nature Biotechnology. 2014 32(8).; Miller J S, Burdick J. ACS Biomater. Sci. Eng. 2016, 2, 1658-1661]. Each technology has its different requirements for the dispensed building material (also referred to herein as printing media), which is derived from the specific application mechanism and the curing/gelation process required to maintain the 3D structure of the scaffold post printing.

For all technologies, and particularly for cell-laden printing, i.e., including cells in the building material dispensed during printing, the static and dynamic physical properties of the dispensed building material, including viscosity, shear thinning and thixotropic properties, determine the accuracy and efficiency of the printing. Therefore, it is desirable to have good control on the specific properties of the printing media over a wide range of conditions, i.e., concentration, temperature, ionic strength and pH.

Additional background art includes Drzewiecki, K. E. et al. Langmuir 30, 11204-11211 (2014); Gaudet, I. D. & Shreiber, D. I. Biointerphases 7, 25 (2012); Isaacson et al., Experimental Eye Research 173, 188-193 (2018); WO 2018/225076; WO 2005/061018; WO 2008/126092; WO 2011/073991; and WO 2014/207749.

SUMMARY OF THE INVENTION

According to an aspect of some embodiments of the present invention there is provided a conjugate comprising fibrinogen and a plurality of curable groups covalently attached to the fibrinogen, the conjugate being devoid of a polymeric moiety.

According to some of any of the embodiments described herein, at least a portion, or all, of the curable groups are photopolymerizable (e.g., UV-curable) groups.

According to some of any of the embodiments described herein, at least a portion, or all, of the curable groups are (meth)acrylic groups.

According to some of any of the embodiments described herein, at least a portion, or all, of the curable groups are attached to lysine residues of the fibrinogen.

According to some of any of the embodiments described herein, at least a portion, or all, of the curable groups are attached directly to the fibrinogen.

According to some of any of the embodiments described herein, at least a portion, or all, of the curable groups are attached directly to the lysine residues (e.g., via an amide bond).

According to some of any of the embodiments described herein, the curable groups are attached to 10 to 100% of the lysine residues of the fibrinogen. According to some of these embodiments, at least a portion, or all, of the curable groups are (meth) acrylic groups.

According to some of any of the embodiments described herein, the curable groups are attached to 10 to 100% of the lysine residues of the fibrinogen.

According to some of any of the embodiments described herein, the conjugate further comprises a labeling agent covalently attached thereto.

According to an aspect of some embodiments of the present invention there is provided a process of preparing the conjugate (curable fibrinogen) as described herein in any of the respective embodiments and any combination thereof, the process comprising coupling a compound that features at least one curable group and at least one reactive group to the fibrinogen under conditions that promote formation of a covalent bond between the reactive group and a chemically compatible reactive group of the fibrinogen.

According to some of any of the embodiments described herein, the reactive group of the fibrinogen is part of a lysine residue.

According to an aspect of some embodiments of the present invention there is provided a curable formulation comprising the conjugate (curable fibrinogen) as described herein in any of the respective embodiments and any combination thereof and a carrier (e.g., a pharmaceutically, cosmetically or cosmeceutically acceptable carrier).

According to some of any of the embodiments described herein, the carrier is an aqueous carrier.

According to some of any of the embodiments described herein, a concentration of the conjugate in the formulation ranges from 1 to 500, or from 1 to 20, or from 5 to 20, mg/mL.

According to some of any of the embodiments described herein, the curable formulation further comprises an agent for promoting polymerization and/or cross-linking of the conjugate.

According to some of any of the embodiments described herein, the curable groups are photopolymerizable groups and the agent is a photoinitiator.

According to some of any of the embodiments described herein, an amount of the photoinitiator ranges from 0.1 to 10% by weight of the total weight of the formulation.

According to some of any of the embodiments described herein, the curable formulation further comprises a cross-linking agent.

According to some of any of the embodiments described herein, the cross-linking agent is or comprises a polymeric material that features at least two curable groups.

According to some of any of the embodiments described herein, the polymeric material is a multi-functional curable synthetic polymer.

According to some of any of the embodiments described herein, each of the at least two curable groups of the cross-linking agent is a photopolymerizable group.

According to some of any of the embodiments described herein, an average molecular weight of the polymeric material ranges from 2 to 50 kDa, or from 5 to 30 kDa.

According to some of any of the embodiments described herein, an amount of the cross-linking agent ranges from 0.5 to 10% by weight of the total weight of the formulation.

According to some of any of the embodiments described herein, the curable formulation further comprises a porogen.

According to some of any of the embodiments described herein, the curable formulation further comprises a biological material other than the fibrinogen.

According to some of any of the embodiments described herein, the biological material comprises cells.

According to some of any of the embodiments described herein, the biological material is devoid of non-cellular proteinaceous material (e.g., enzymes such as thrombin).

According to some of any of the embodiments described herein, the curable formulation is devoid of a synthetic polymeric material.

According to some of any of the embodiments described herein, the curable formulation is a modeling material formulation usable for additive manufacturing of a three-dimensional object having in at least a portion thereof a fibrinogen-based material.

According to an aspect of some embodiments of the present invention there is provided a scaffold obtained by subjecting the curable formulation as described herein in any of the respective embodiments and any combination thereof to a suitable curing condition (a condition that affect polymerization and/or cross-linking of the curable groups).

According to an aspect of some embodiments of the present invention there is provided a scaffold comprising a three-dimensional network formed upon subjecting the conjugate (curable fibrinogen) as described herein in any of the respective embodiments and any combination thereof, or a curable formulation comprising the conjugate, as described herein in any of the respective embodiments and any combination thereof, and carrier to a suitable curing condition (a condition that affect polymerization and/or cross-linking of the curable groups).

According to an aspect of some embodiments of the present invention there is provided a pharmaceutical, cosmetic or cosmeceutical composition comprises the scaffold as described herein and a pharmaceutically, cosmetic or cosmeceutically acceptable carrier.

According to some of any of the embodiments described herein, the scaffold is in a form of a hydrogel.

According to some of any of the embodiments described herein, the scaffold is characterized by shear storage modulus (G') of at least 50 Pa, at least 100 Pa, or at least 200 Pa or at least 300 Pa or at least 400 Pa.

According to some of any of the embodiments described herein, the scaffold is characterized by a swelling capacity (a degree of swelling, as defined herein for Qt) higher than 90% or higher than 95%.

According to some of any of the embodiments described herein, the scaffold is characterized by a proteolytic degradation that is lower from a proteolytic degradation of fibrinogen (e.g., lower by at least 50%, for example by 50% to 98%).

According to some of any of the embodiments described herein, the scaffold further comprises cells incorporated thereon and/or therewithin.

According to some of any of the embodiments described herein, a viability of the cells is maintained upon incubating the scaffold for at least 5 days.

According to some of any of the embodiments described herein, the scaffold is devoid of non-cellular proteinaceous material (e.g., enzymes such as thrombin).

According to some of any of the embodiments described herein, the scaffold is devoid of a synthetic polymeric material.

According to an aspect of some embodiments of the present invention there is provided a method of inducing formation of a tissue in a subject in need thereof, the method comprising implanting the scaffold as described herein in any of the respective embodiments and any combination thereof, or a composition comprising same, in the subject, thereby inducing the formation of the tissue.

According to an aspect of some embodiments of the present invention there is provided a method of inducing formation of a tissue in a subject in need thereof, the method comprising administering to the subject the curable fibrinogen (conjugate) or the curable formulation comprising same, as these are described herein in any of the respective embodiments and any combination thereof, and exposing the conjugate or the formulation to a condition that effects polymerization and/or cross-linking of the conjugate, thereby inducing the formation of the tissue.

According to an aspect of some embodiments of the present invention there is provided a method of treating a disorder characterized by tissue damage or loss in a subject in need thereof, the method comprising implanting the scaffold as described herein in the subject, thereby treating the disorder characterized by tissue damage or loss.

According to an aspect of some embodiments of the present invention there is provided a method of treating a disorder characterized by tissue damage or loss in a subject in need thereof, the method comprising administering to the subject the curable fibrinogen (conjugate) or the curable formulation comprising same, as these are described herein in any of the respective embodiments and any combination thereof, or a composition comprising the scaffold, as described herein, and exposing the formulation to a condition that effects polymerization and/or cross-linking of the conjugate, thereby treating the disorder characterized by tissue damage or loss.

According to an aspect of some embodiments of the present invention there is provided a process of additive manufacturing a three-dimensional object featuring, in at least a portion thereof, a fibrinogen-based material, the process comprising dispensing at least one modeling material formulation to sequentially form a plurality of layers in a configured pattern corresponding to a shape of the object, wherein for at least a portion of the layers, the dispensing is of a modeling material formulation that comprises the conjugate (curable fibrinogen) or a curable formulation comprising the conjugate, as these are described herein in any of the respective embodiments and any combination thereof, and a carrier, thereby manufacturing the three-dimensional object.

According to some of any of the embodiments described herein, the process further comprises exposing the portion of the layers to a curing condition suitable for hardening the conjugate or the formulation.

According to some of any of the embodiments described herein, at least a portion of the curable groups are photo-curable groups, and the curing condition comprises irradiation.

According to an aspect of some embodiments of the present invention there is provided a three-dimensional biological object featuring, in at least a portion thereof, a fibrinogen-based material, obtainable by the additive manufacturing process as described herein.

According to an aspect of some embodiments of the present invention there is provided a kit comprising the conjugate (curable fibrinogen) or a curable formulation comprising the conjugate, as these are described herein in any of the respective embodiments and any combination thereof packaged therein, the kit being identified for use in forming a scaffold or a three-dimensional object that comprises, in at least a portion thereof, a fibrinogen-based material. In some embodiments, the kit is identified for use in additive manufacturing of the scaffold, as described herein, for example, as a modeling material formulation. In some embodiments, the kit is identified for use in any of the methods described herein in which forming a scaffold in vivo or ex vivo is beneficial.

According to an aspect of some embodiments of the present invention there is provided a kit comprising the scaffold as described herein in any of the respective embodiments, or a composition comprising same, as described herein. According to some embodiments, the kit further comprises means for administering the scaffold or the composition, or for implanting the scaffold, in a subject, and is identified for use in any of the methods described herein (e.g., inducing formation of a tissue and treating disorders associated with tissue damage or loss).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a table presenting the amino acid composition of the polypeptide chains of fibrinogen and fibrin.

Figures 2A, 2B:
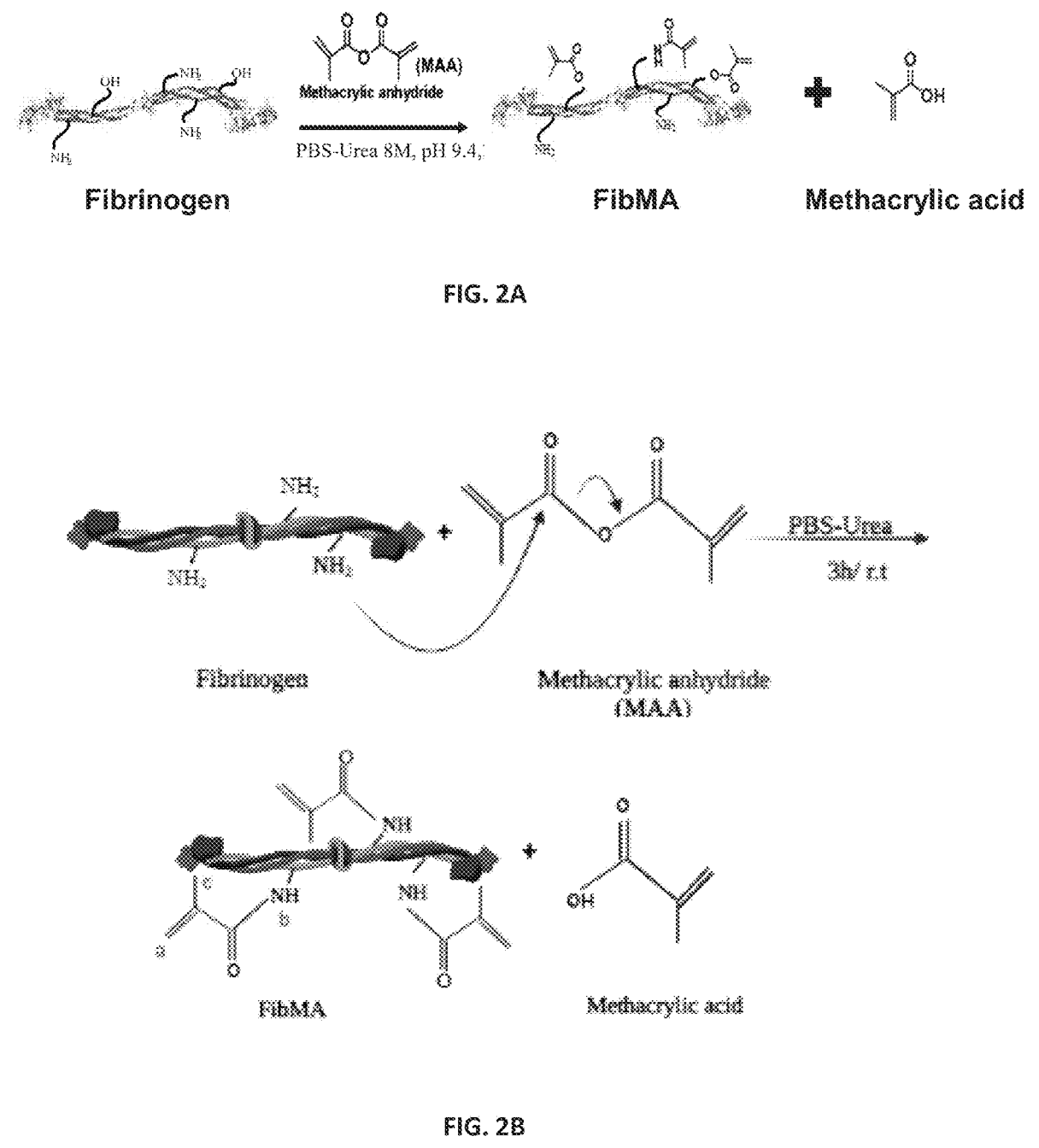

FIGS. 2A-B present schemes showing the conjugation of methacrylate to fibrinogen, according to some embodiments of the present invention.

Figure 3B:
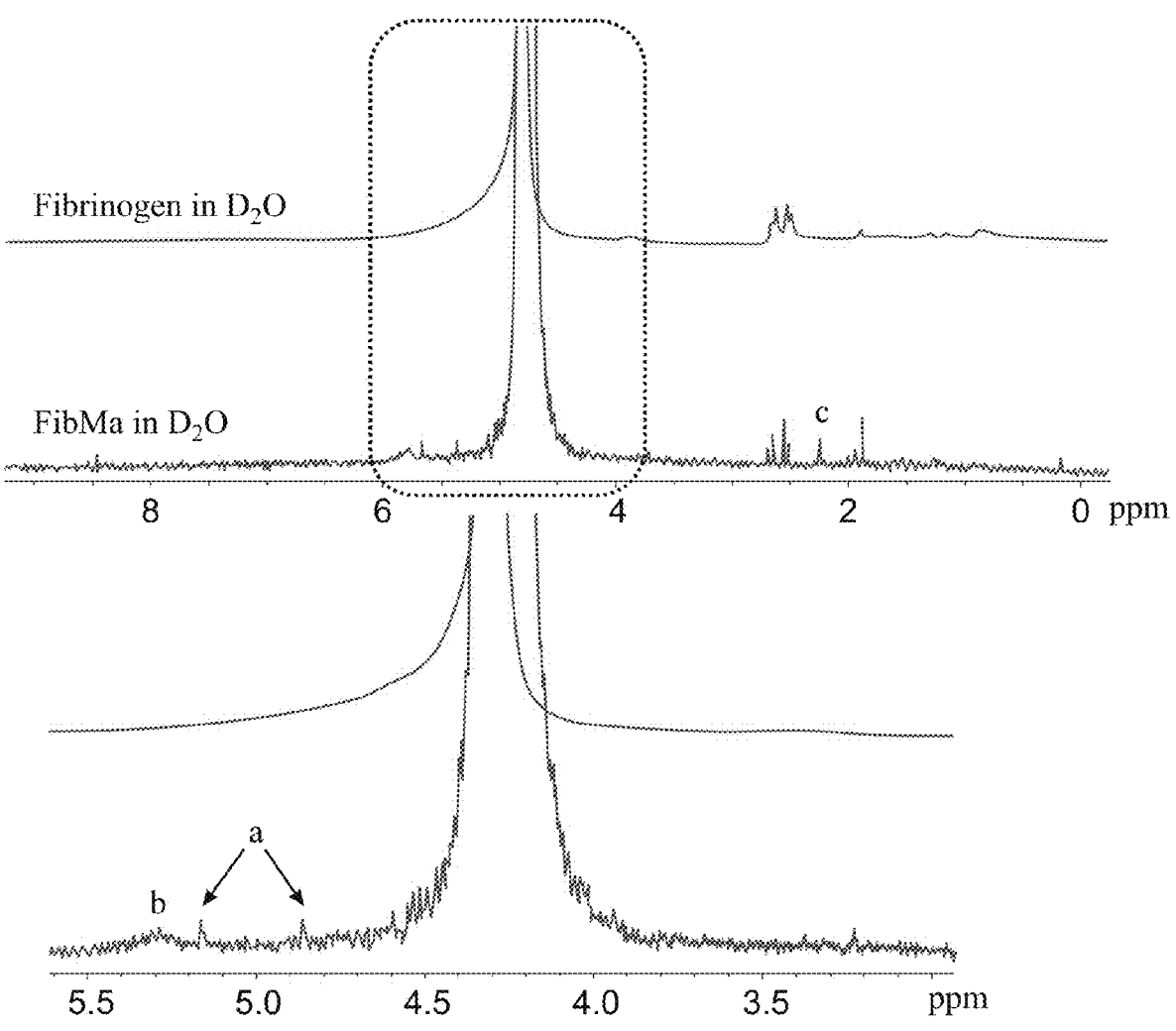

FIGS. 3A-B present $^1$H-NMR spectra of Fibrinogen and FibMA samples in $D_2O$. In FIG. 3A (i) (upper panel) presents the full spectra (0-8 ppm) showing an identified new peak (denoted (c)) in the range of 1.9 ppm; and (ii) (lower panel) is a close-up of the region between 3-7 ppm showing the peaks between 6.4-5.3 (denoted (a) and (b)). Each proton peak corresponds to its respective region on the methacrylate attached to the fibrinogen (insert). In FIG. 3B, the upper panel presents the full spectra (upper panel) and a close up (lower panel) of native fibrinogen and of FibMA$_{0.4\%}$, with the new proton peaks belonging to methacryloyl groups of FibMA$_{0.4\%}$ appearing between 5.8-5.3 ppm (denoted (a) and (b) and at 2.2 ppm (denoted (c).

Figure 4A:
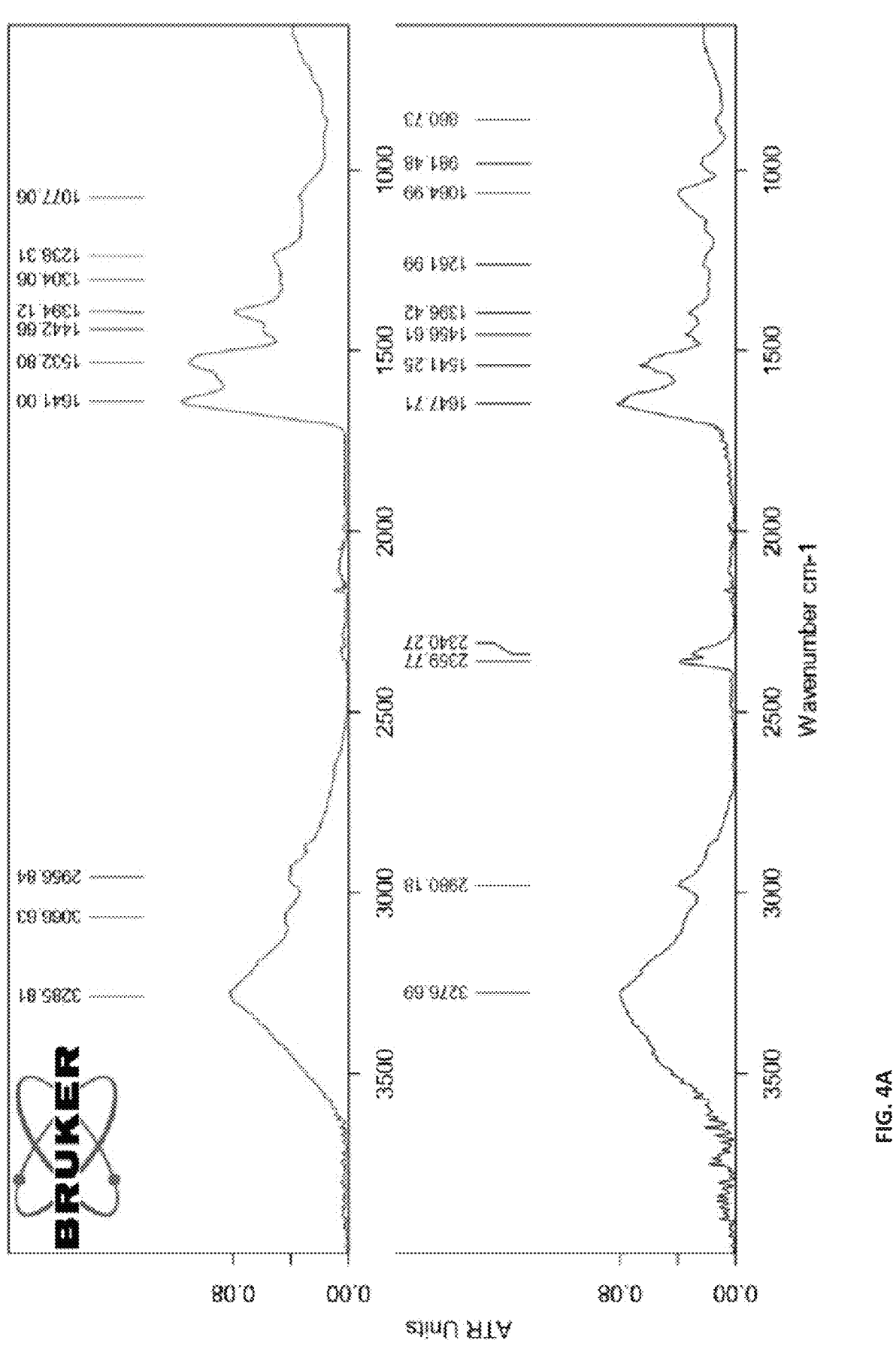
Figure 4B:
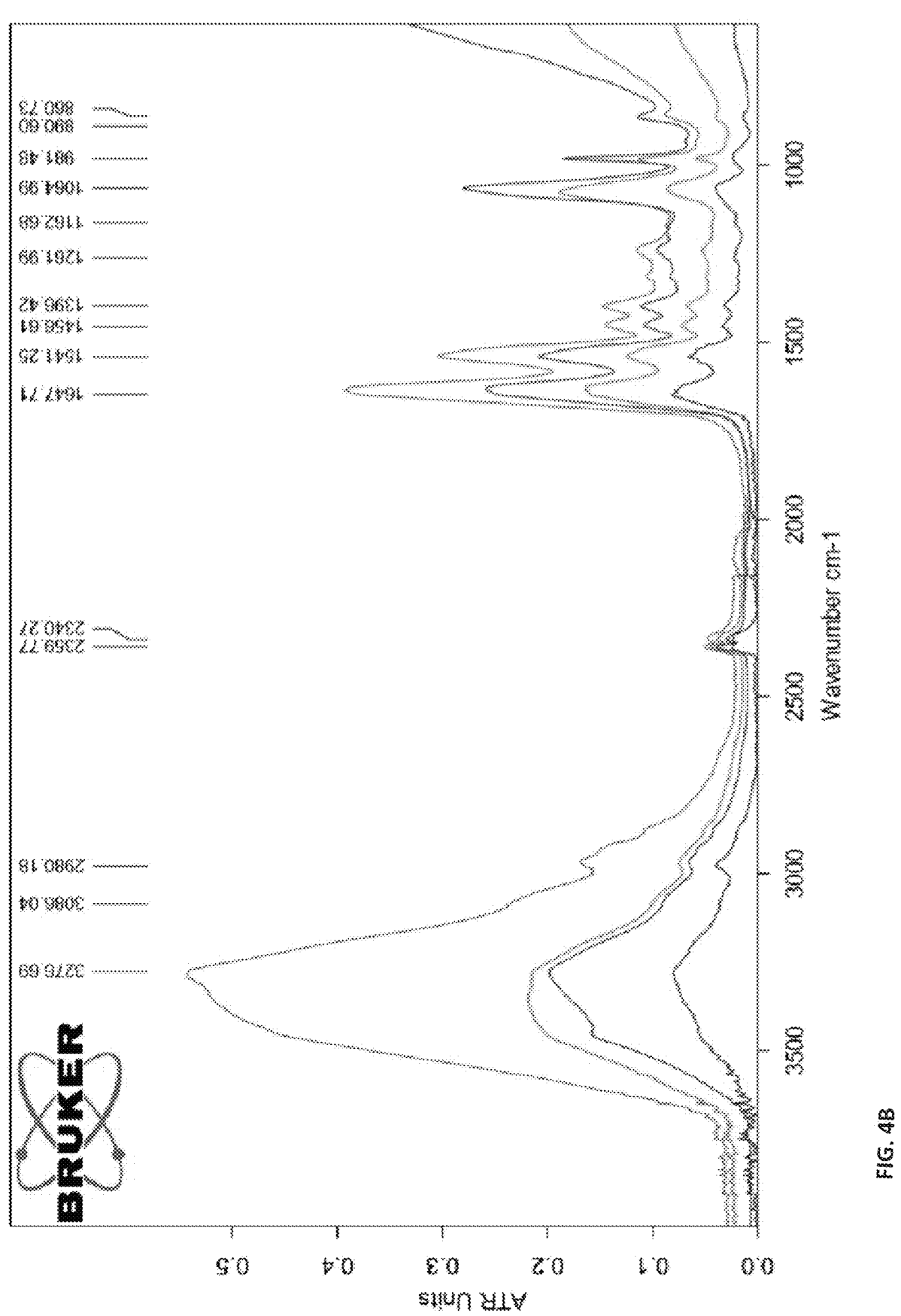

FIGS. 4A-B present FTIR spectra of fibrinogen and FibMA samples. FIG. 4A presents the full spectra for both the methacrylated (blue) and unreacted (red) fibrinogen, with a distinct new peak on the FibMA visible at around 980 ppm. FIG. 4B presents the spectra of FibMA with different degrees of methacrylation: FibMA (FibMA$_{0.4\%}$) in blue, FibMA0.5 (FibMA$_{0.2\%}$) in pink, FibMA0.25 (FibMA$_{0.1\%}$) in green and FibMA0.125 (FibMA$_{0.05\%}$) in brown.

Figure 5A:
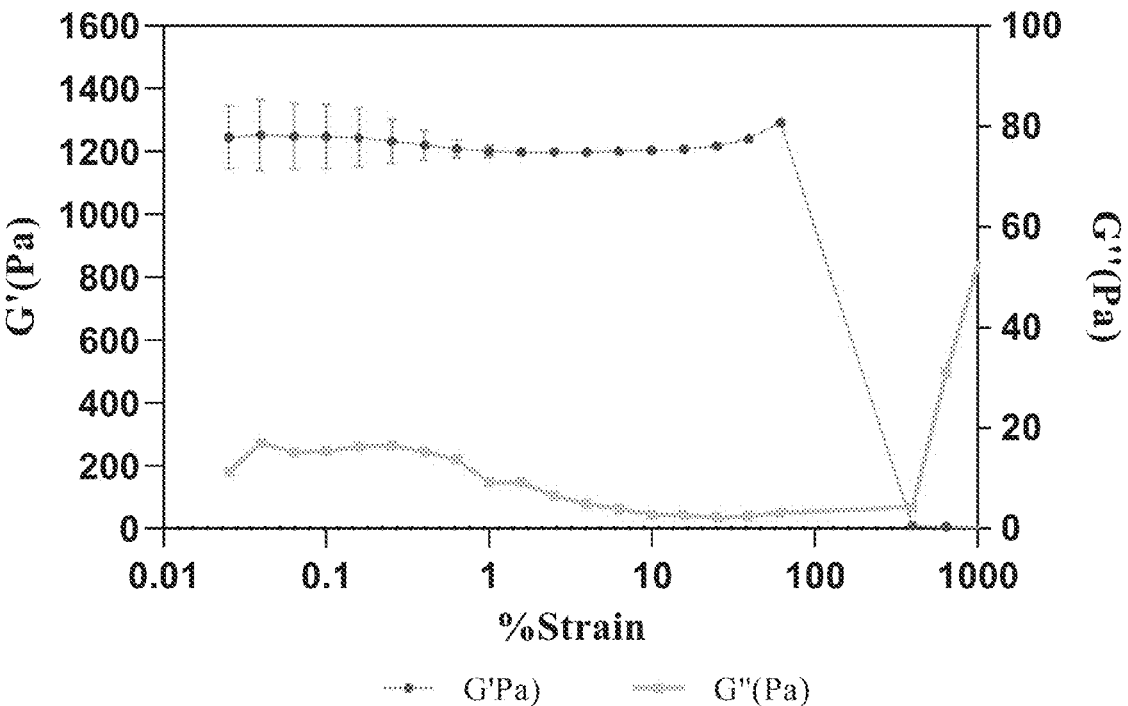
Figure 5B:
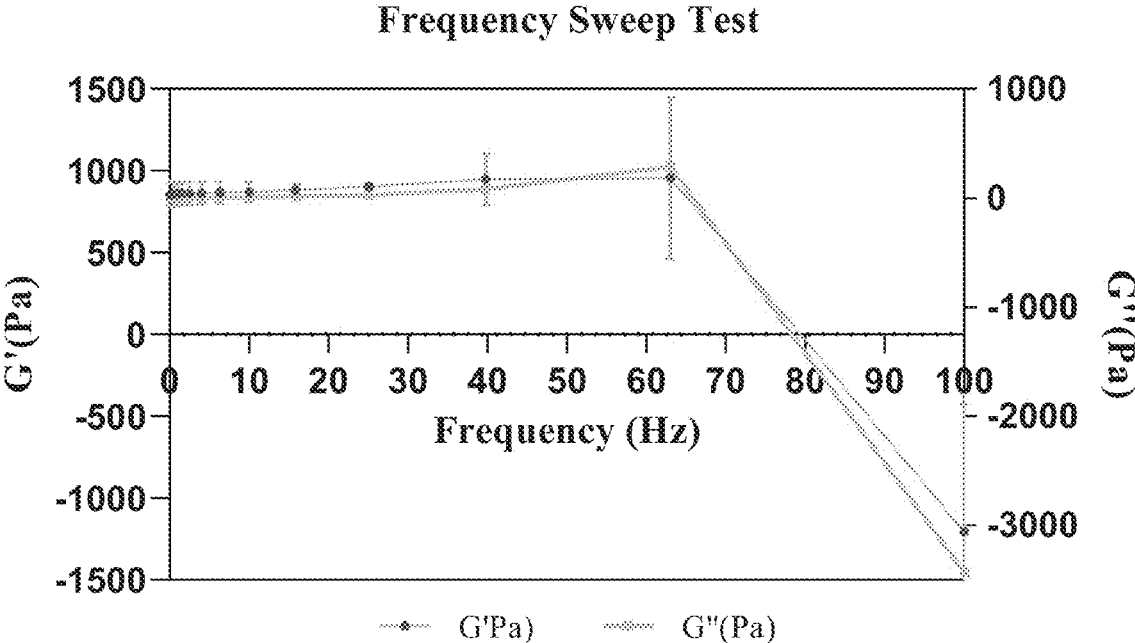

FIGS. 5A-B present data showing the rheological properties of FibMA (FibMA$_{0.4\%}$; 8 mg/ml) hydrogel under oscillatory shear. The FibMA was analyzed by amplitude sweeps in oscillatory shear at a constant frequency of 2 Hz and an oscillation strain of 0.025-1000%.

Figure 6:
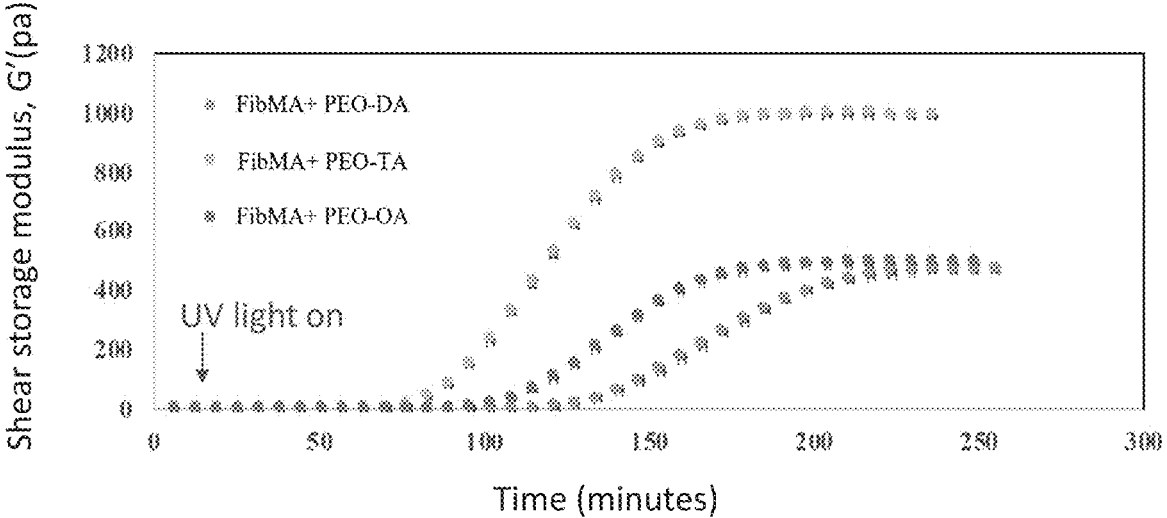

FIG. 6 presents the shear storage modulus of FibMA hydrogel prepared in the presence of different compositions of PEO-Acrylate. Time sweep oscillatory shear experiments were performed on FibMA (FibMA$_{0.4\%}$; 8 mg/ml) with addition of 2% (w/v) PEO-DA, PEO-TA or PEO-OA. The samples were tested at room temperature; UV irradiation was initiated after 15 seconds.

Figure 7A:
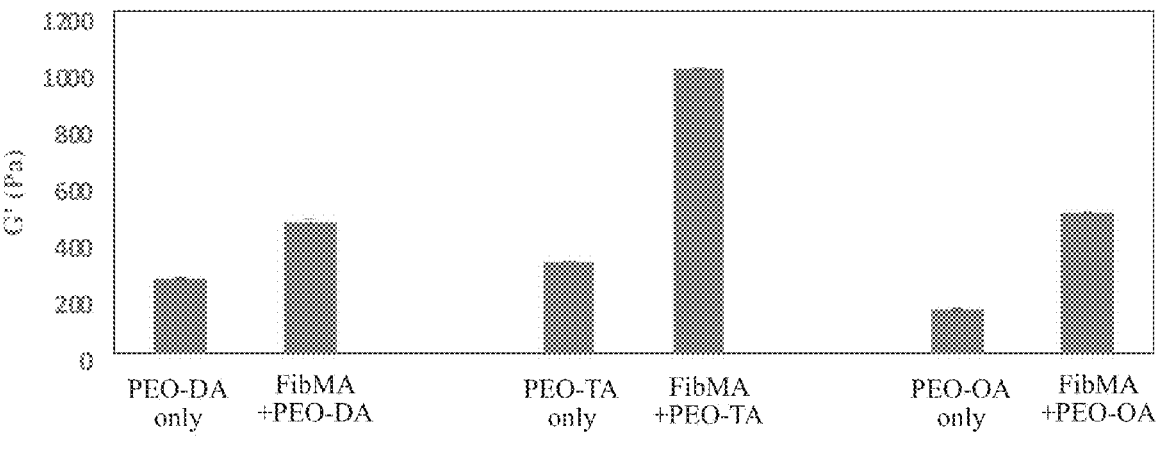
Figure 7B:
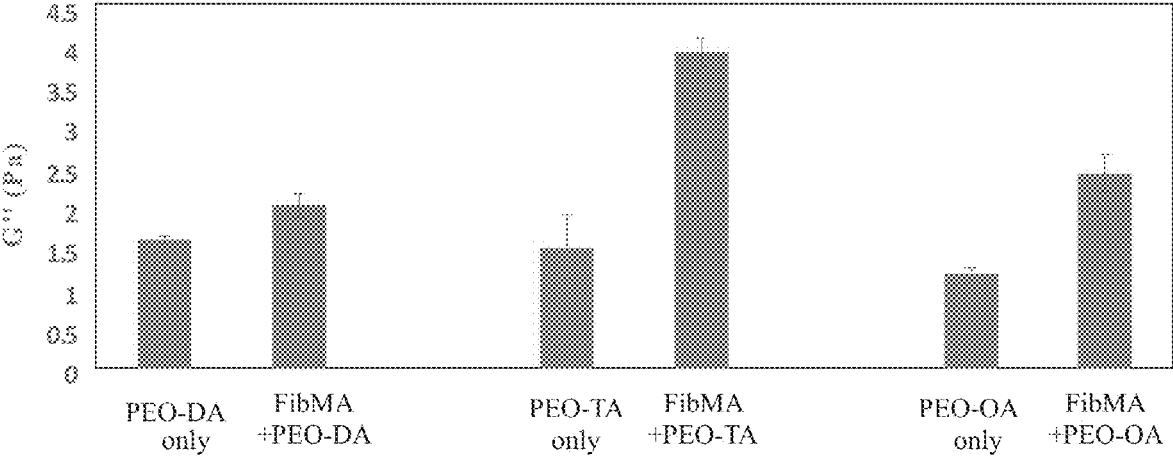

FIGS. 7A-B present the data obtained in rheological measurements, showing the storage modulus, G' (FIG. 7A) and the loss modulus, G" (FIG. 7B) for hydrogels made of three FibMA (FibMA$_{0.4\%}$) formulations: FibMA 8 mg/ml with 2% PEO-DA (10 KDa), FibMA 8 mg/ml with 2% PEO-TA (20 KDa) and FibMA 8 mg/ml with 2% of PEO-OA (20 KDa) vs. the hydrogels made with the three respective acrylated PEOs only (2% w/v).

Figure 8:
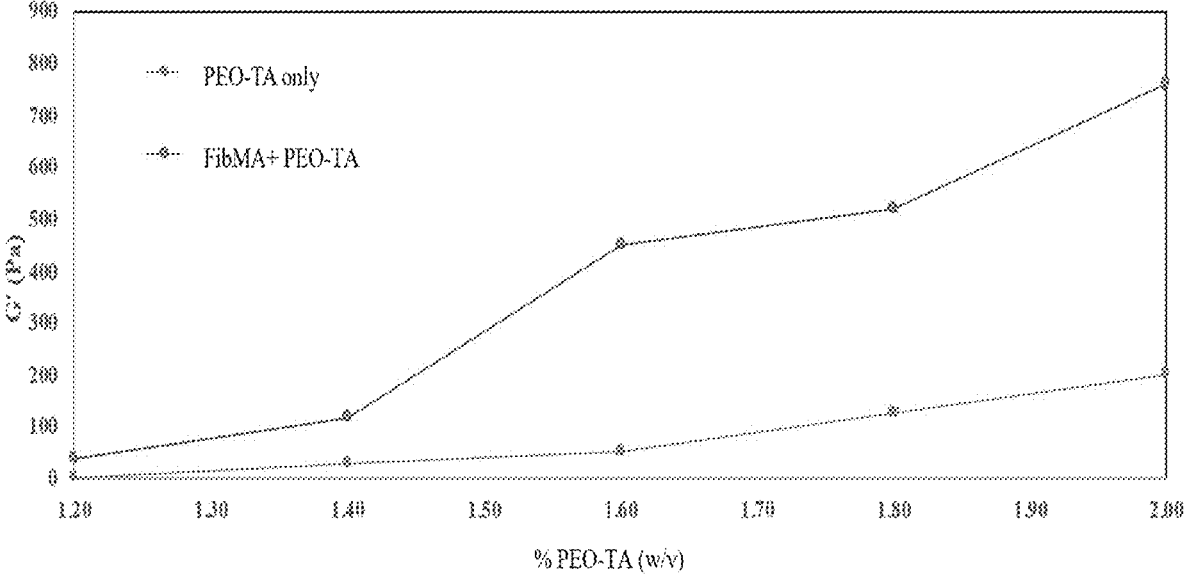

FIG. 8 presents data obtained in rheological oscillatory shear measurements, showing the storage modulus, G'(Pa), of hydrogels made of formulations containing 5 mg/ml FibMA hydrogels with different percent (w/v) of a PEO-TA crosslinker. The storage modulus of hydrogels formed by PEO-TA alone is shown for comparison.

Figure 9A:
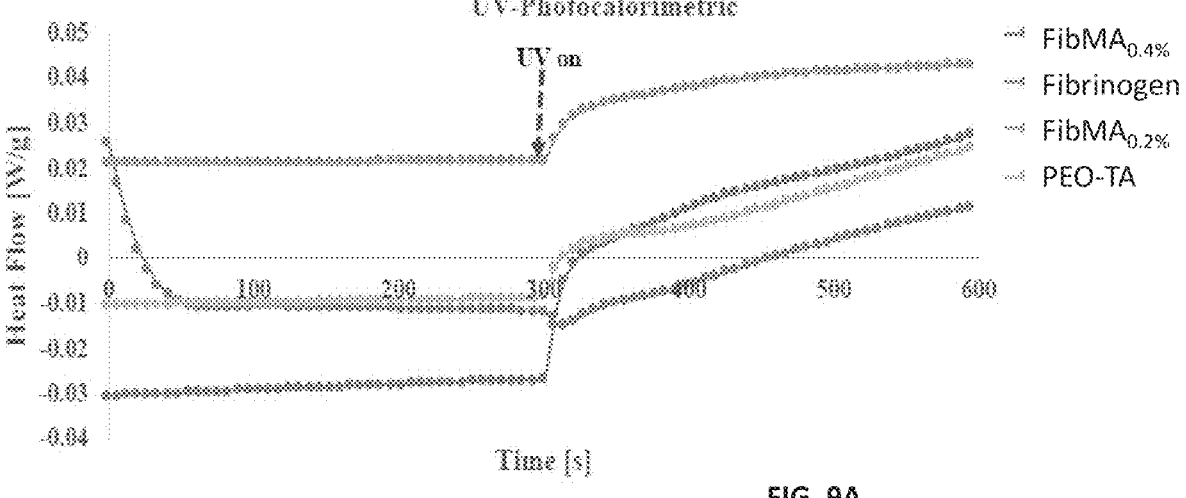
Figure 9B:
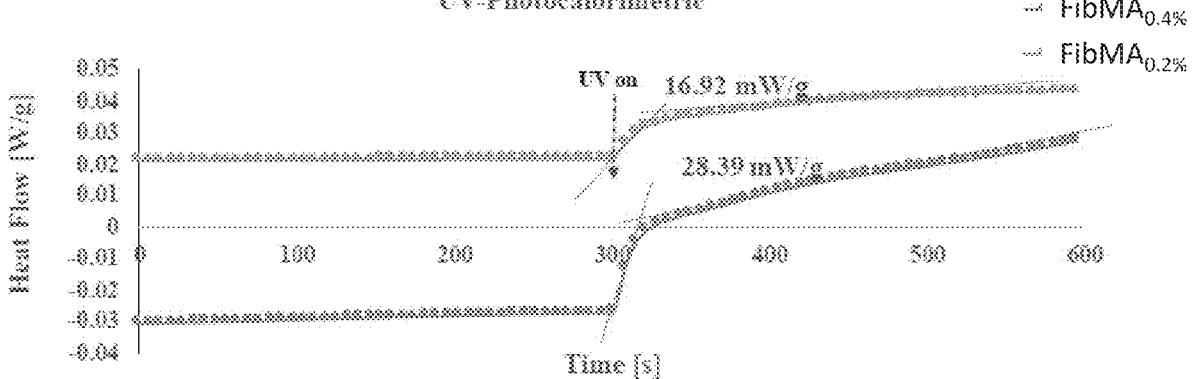

FIGS. 9A-B present Differential Photocalorimetry (DPC) results showing the enthalpy changes in the FibMA materials as measured during and after exposure to UV light (wavelength 365 nm) for 5 minutes. FIG. 9A presents data of Differential Scanning calorimeter (DSC) with a curing cell adaptor used to measure the heat flow upon irradiation of UV light. The samples tested include FibMA (FibMA$_{0.4\%}$) and FibMA0.5 (FibMA$_{0.2\%}$); fibrinogen (unmodified) and PEO-TA were used as negative and positive controls, respectively. FIG. 9B show that the enthalpy of the photopolymerization reaction (shown in red) was nearly two-fold higher for the FibMA (FibMA$_{0.4\%}$) when compared to the FibMA0.5 (FibMA$_{0.2\%}$).

Figure 10:
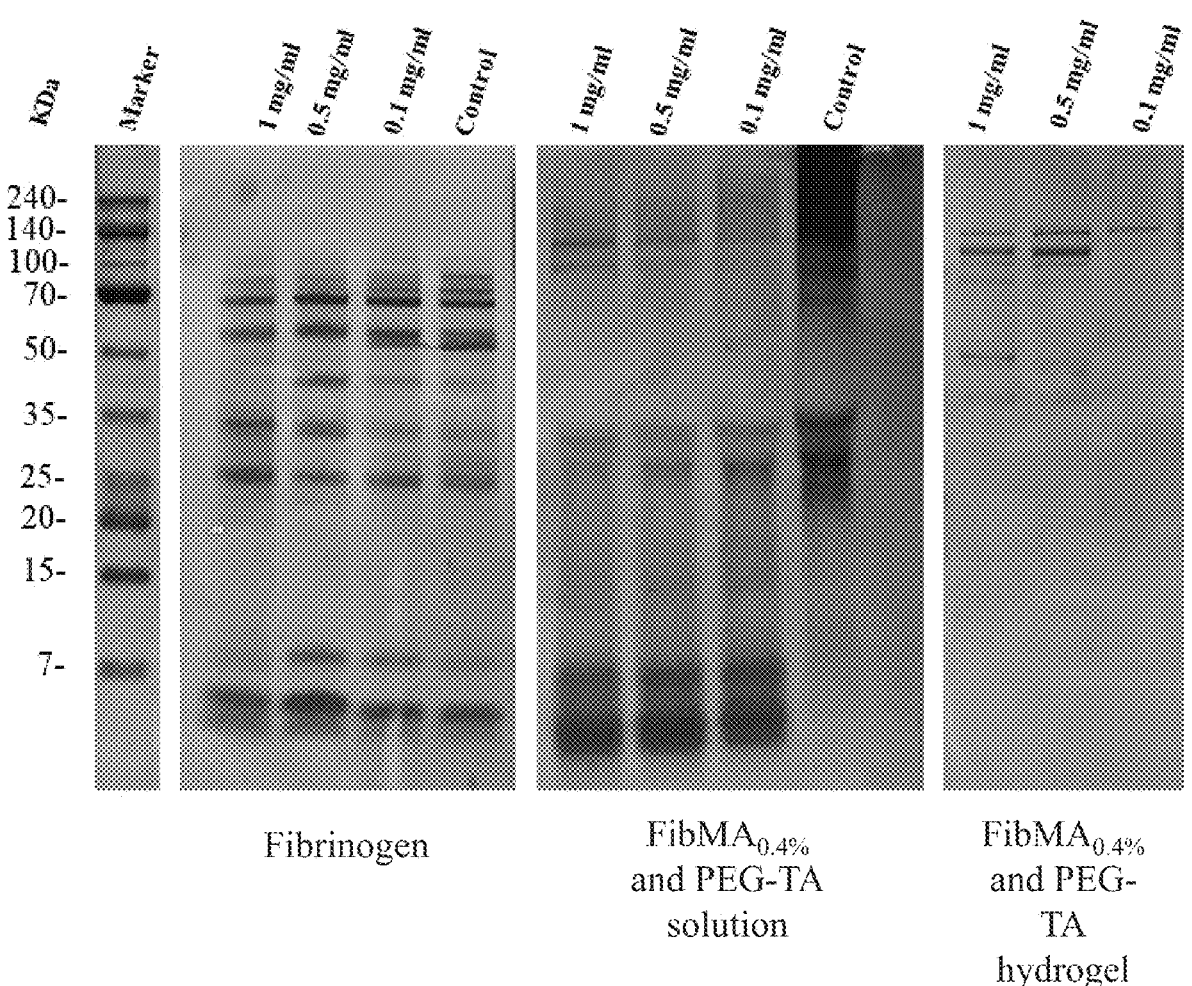

FIG. 10 presents SDS-PAGE analyses showing degradation products of fibrinogen and FibMA after incubation in 0.1 mg/ml, 0.5 mg/ml and 1 mg/ml collagenase, as indicated. The SDS-PAGE results are shown for the degradation products of fibrinogen (left), of a precursor solution of FibMA$_{0.4\%}$ and PEG-TA (center), and of hydrogels made from FibMA$_{0.4\%}$ and PEG-TA (right). Control (Marker) samples without collagenase are shown for comparison.

Figure 11:
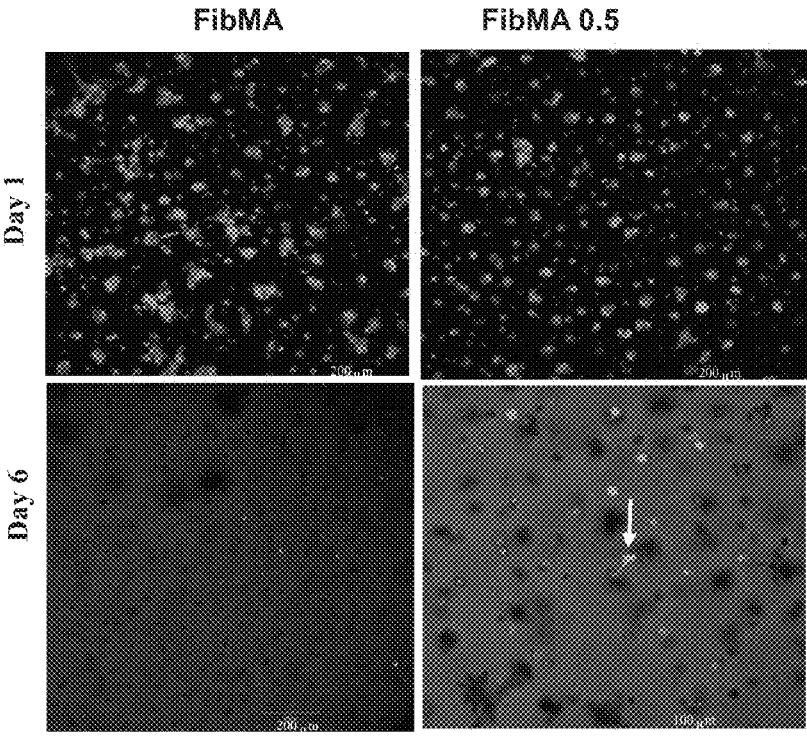

FIG. 11 presents florescence and phase-contrast imaging of NHDF-GFP cells (green) ($3 \times 10^6$ cell/ml) encapsulated in 8 mg/ml FibMA (FibMA$_{0.4\%}$) with 1.2% PEO-TA and FibMA0.5 (FibMA$_{0.2\%}$) with 1.4% PEO-TA. Both hydrogels were formed with 0.1% Irgacure 2959 after 5 minutes UV irradiation. Arrow shows a cell spreading in the FibMA matrix after 6 days in 3D culture.

Figure 12:
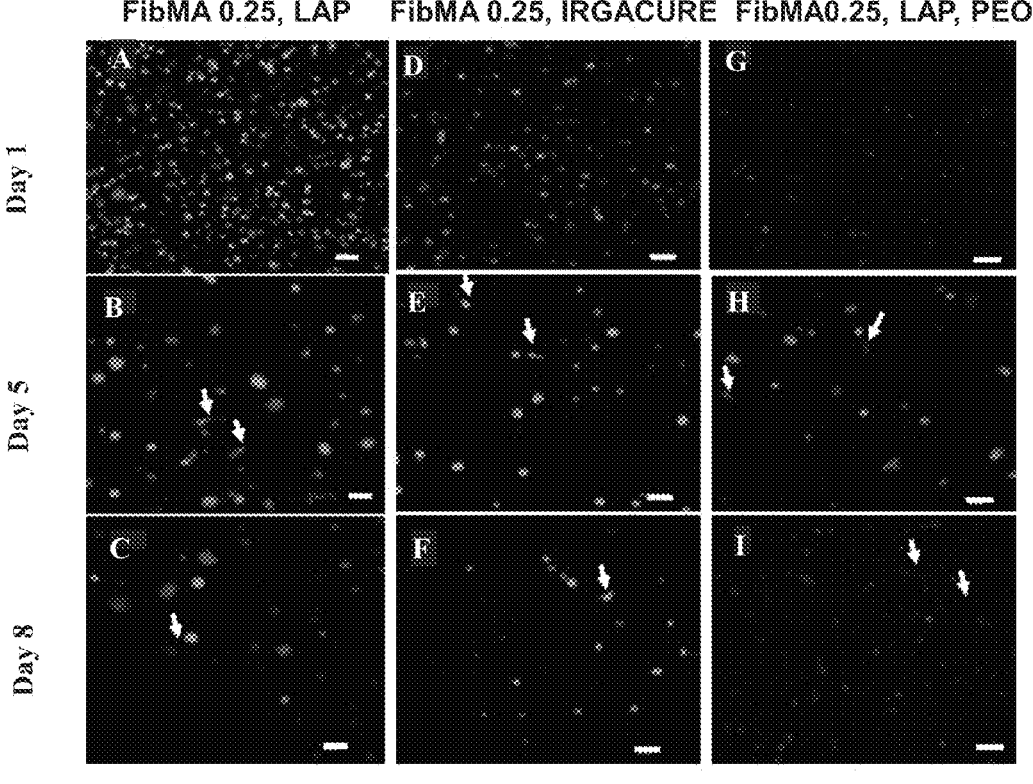

FIG. 12 presents fluorescence images of NHDF ($3 \times 10^6$ cell/ml) encapsulated in hydrogels formed of different formulations of FibMA, where calcein (green) represents live cells, and ethidium (red) represents dead cells. Scale bar 50 (A-C) FibMA0.25 (FibMA$_{0.1\%}$), 1.8% PEO-TA, 0.1% LAP and 1 minute irradiation time. (D-F) FibMA0.25 (FibMA$_{0.1\%}$), 1.8% PEO-TA, 0.1% IRGACURE 2959 with 5 minutes UV irradiating. (G-I) FibMA0.25 (FibMA$_{0.1\%}$), 1.8% PEO-TA, 0.8% PEO and 0.1% LAP and 0.5 minute irradiation time.

Figure 13A:
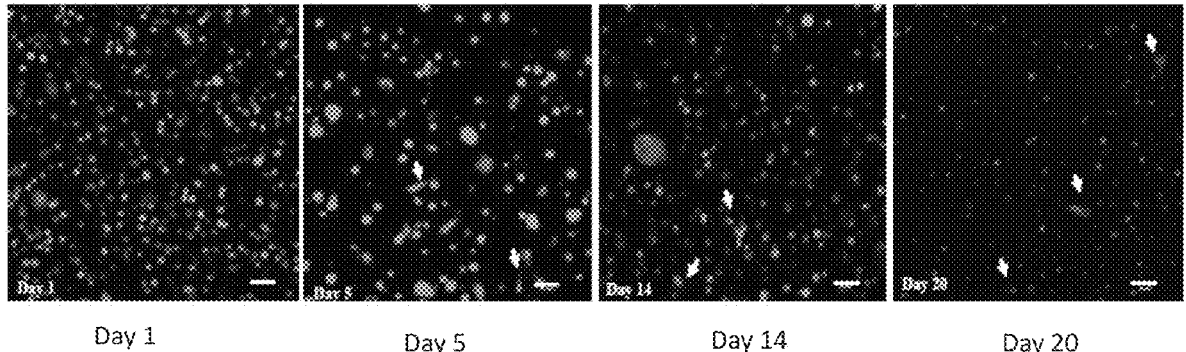
Figure 13B:
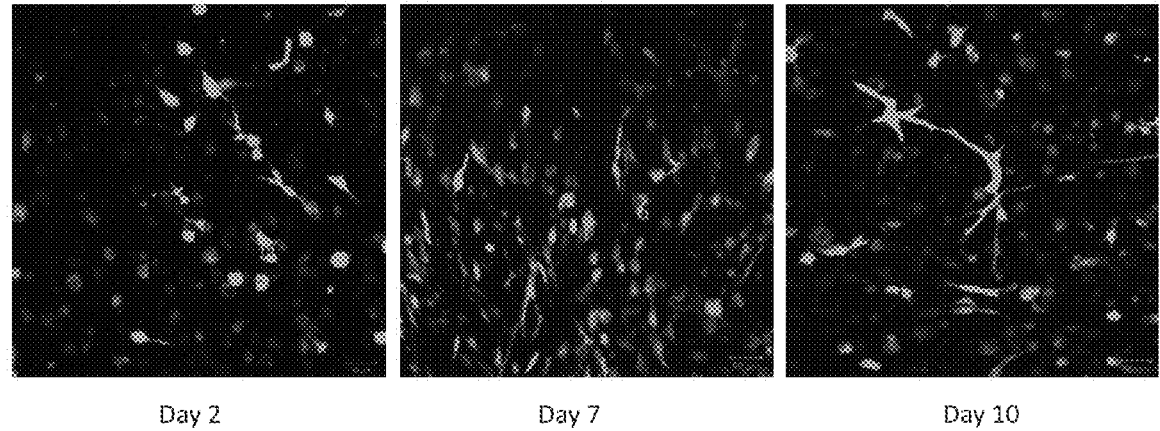

FIGS. 13A-B present florescence imaging of NHDF cells ($3 \times 10^6$ cells/ml) encapsulated in 8 mg/ml FibMA0.25 (FibMA$_{0.1\%}$) with 1.8% PEO-TA (G'=360 Pa), 0.1% LAP and blue light irradiation (405 nm) for 1 minute (FIG. 13A), and of NHDF cells ($3 \times 10^6$ cells/ml) encapsulated in 40 mg/ml FibMA$_{0.2\%}$ with 0.1% LAP and blue light irradiation (405 nm) for 1 minute (FIG. 13B). Scale bar=50 μm.

Figure 14:
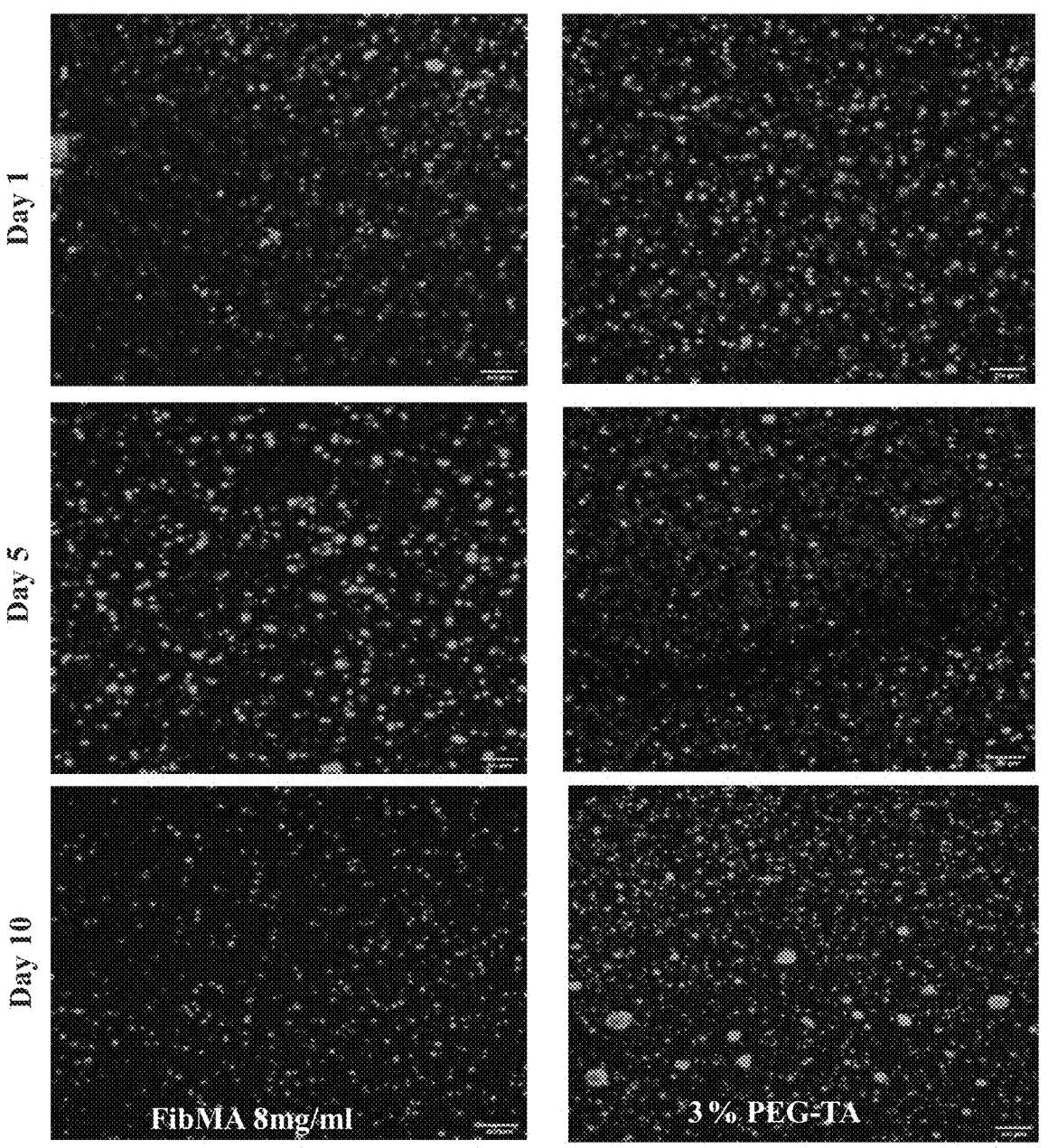

FIG. 14 presents fluorescence images of C2C12 ($6 \times 10^6$ cells/ml) encapsulated in FibMA (left) and PEO-TA (right) hydrogels, where calcein (green) represents live cells, and ethidium (red) represents dead cells. Scale bar=200 μm.

Figure 15:
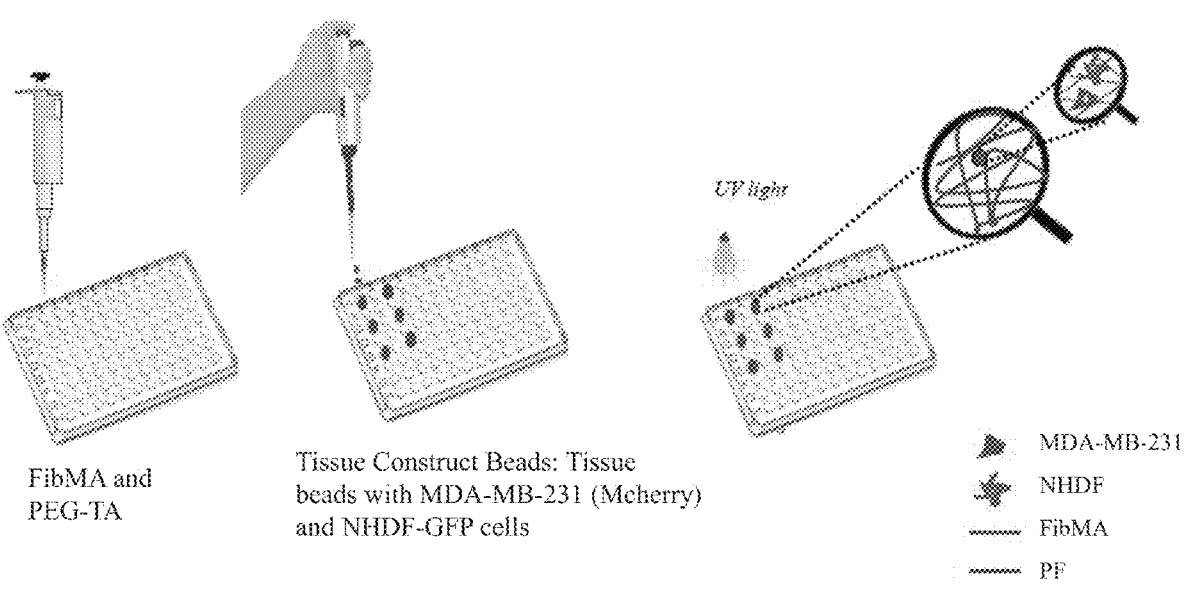

FIG. 15 is a schematic illustration of a gel-in-gel assay that uses dense tissue construct beads and encapsulates these into the FibMA hydrogel in order to study cell invasion into the bioactive matrix.

Figure 16:
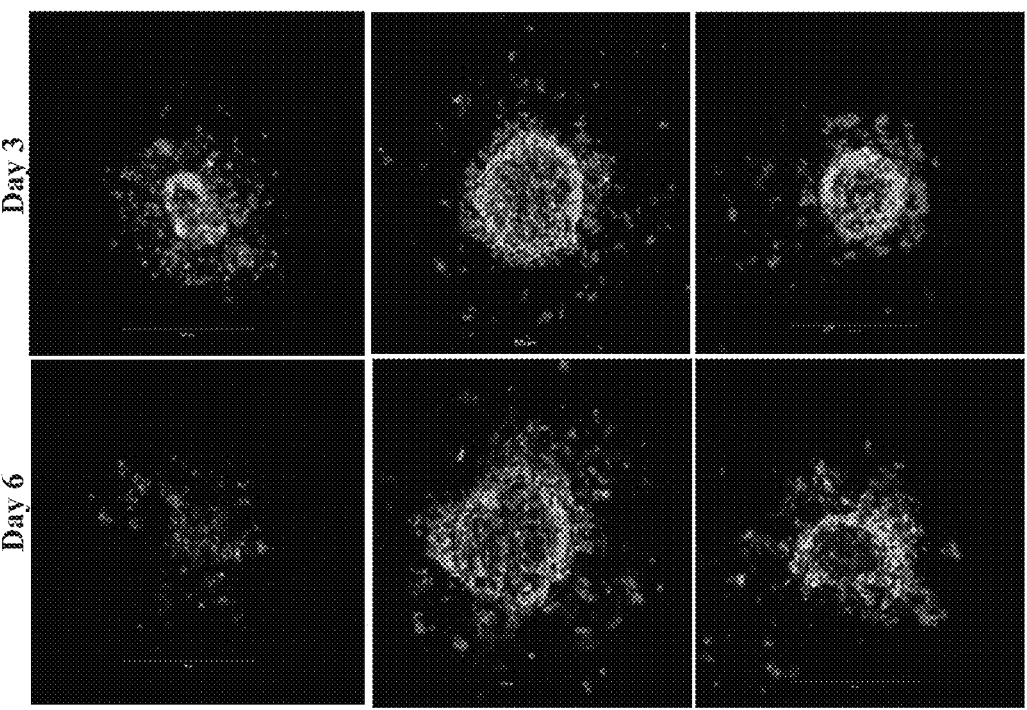

FIG. 16 presents the results from the gel-in-gel invasion assay with MDA-MB231-mCherry (red) and NHDF-GFP (green) within tissue construct beads, invading into a FibMA hydrogel made from 6 mg/ml FibMA and supplemented with 1.2% w/v PEO-TA. Three independent samples of invasion from the bead constructs are shown.

Figure 17:
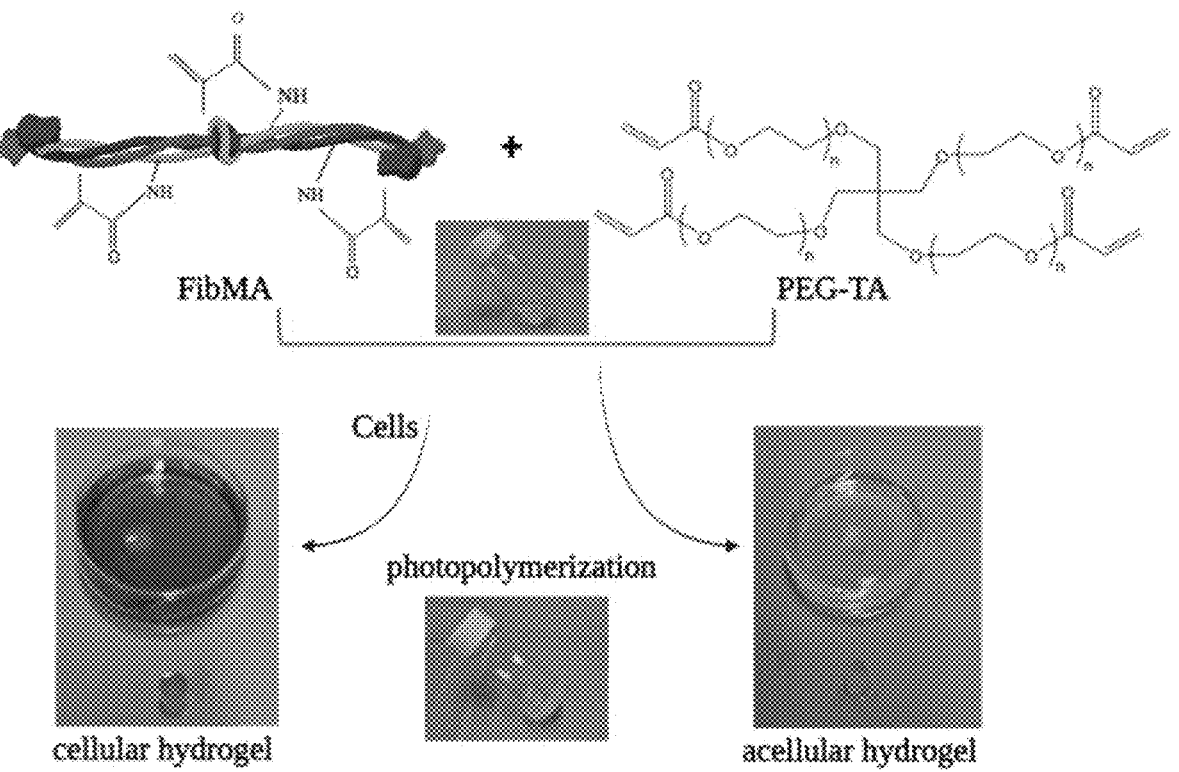

FIG. 17 is a schematic illustration accompanied by photographs showing the preparation of hydrogel constructs for 3D cell culture and acellular applications via photopolymerization of FibMA and PEG-TA.

Figure 18A:
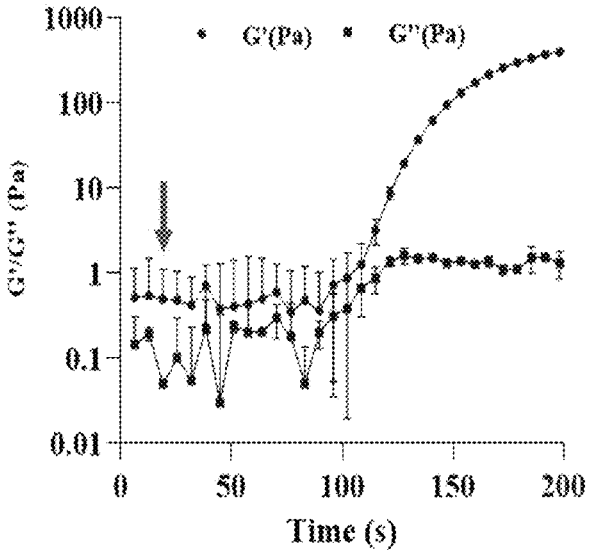
Figure 18B:
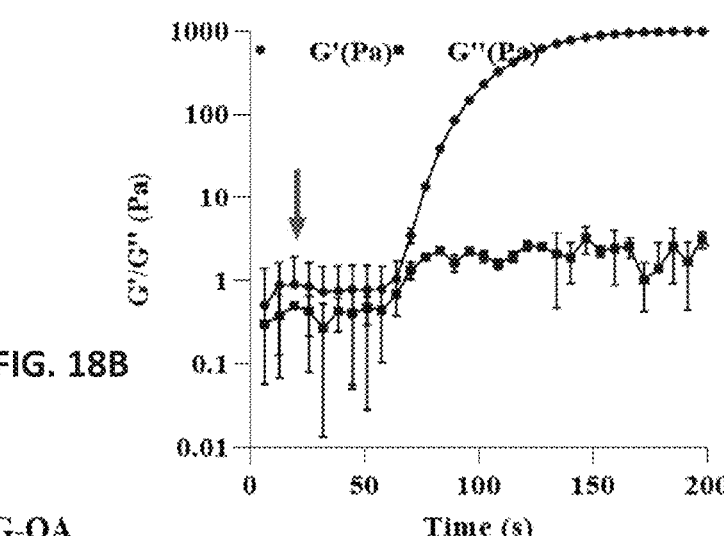
Figure 18C:
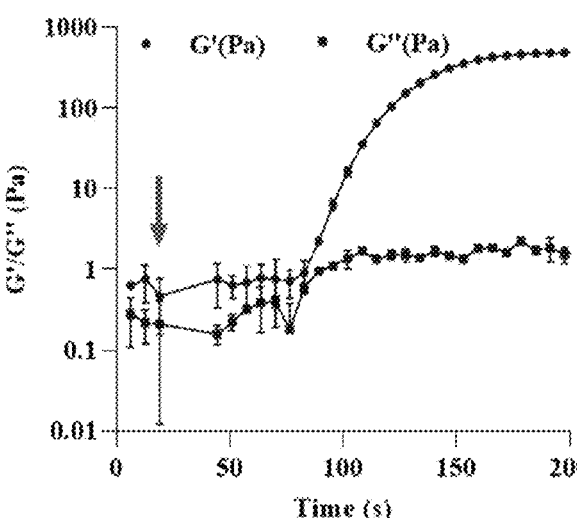

FIGS. 18A-C present the shear storage modulus and loss modulus of compositions made of FibMA$_{0.4\%}$ (8 mg/ml) with 2% w/v PEG-DA (FIG. 18A), PEG-TA (FIG. 18B), or PEG-OA (FIG. 18C). The samples were tested at room temperature; UV irradiation was initiated after 15 seconds (indicated by red arrow).

Figure 18D:
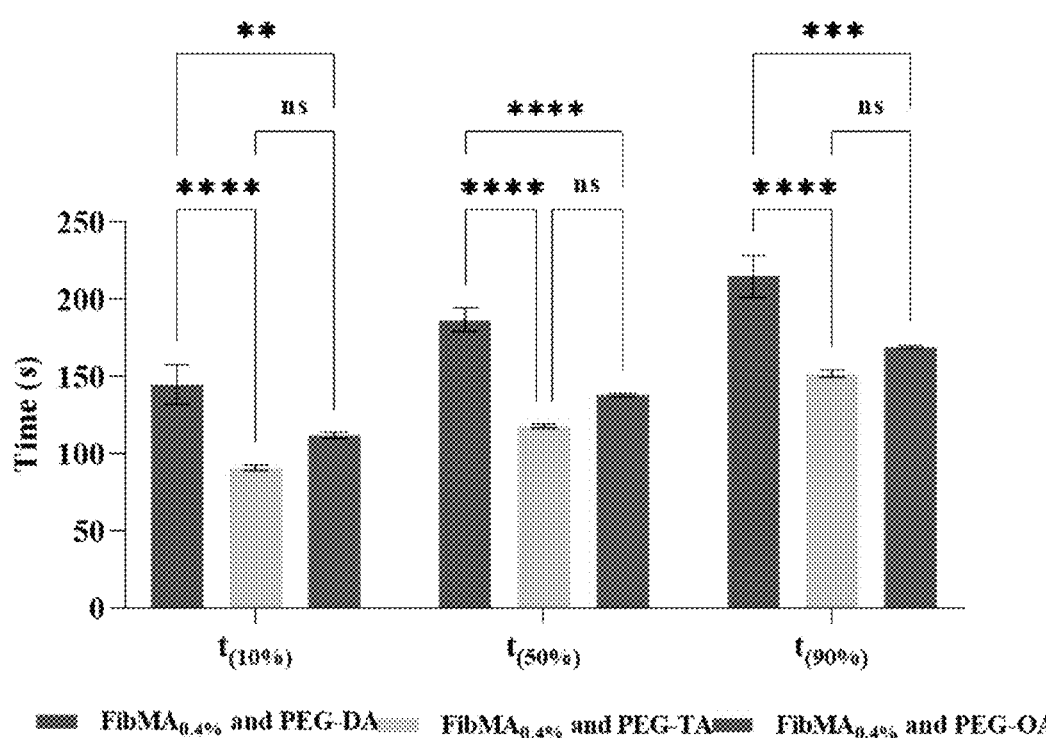
Figure 18E:
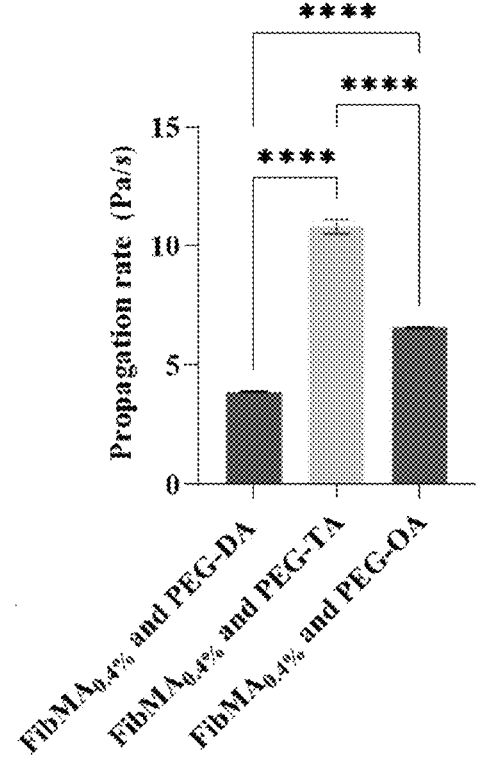

FIGS. 18D-E show the quantification of $t_{10}$, $t_{50}$ and $t_{90}$ kinetic values (FIG. 18D) and the propagation rates (FIG. 18E) of hydrogel formation for the three FibMA formulations: FibMA$_{0.4\%}$ 8 mg/ml with 2% PEG-DA (10 KDa), FibMA$_{0.4\%}$ 8 mg/ml with 2% PEG-TA (20 KDa) and FibMA$_{0.4\%}$ 8 mg/ml with 2% of PEG-OA (20 KDa) shown in FIGS. 18A-C. "ns" indicates p>0.05,  indicates p<0.01, * indicates p<0.001, and **** indicates p<0.0001; values are given as mean±SD; n=3.

Figure 19A:
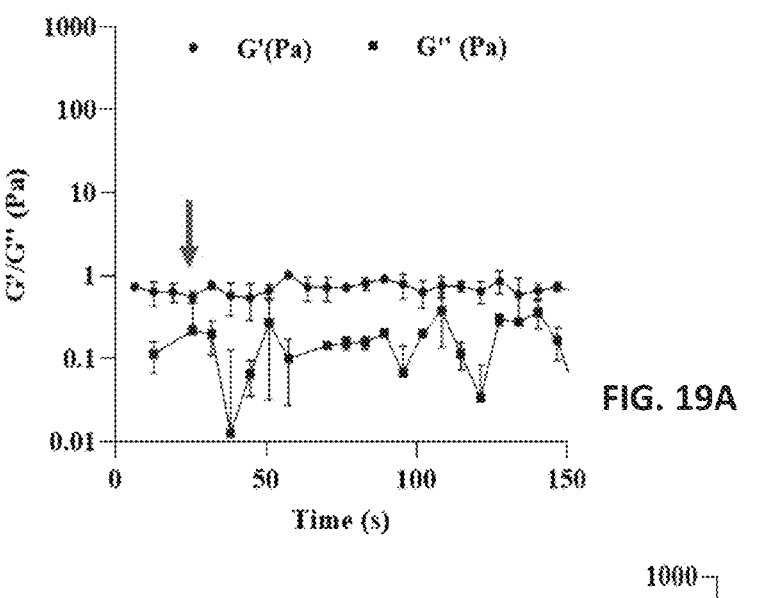
Figure 19B:
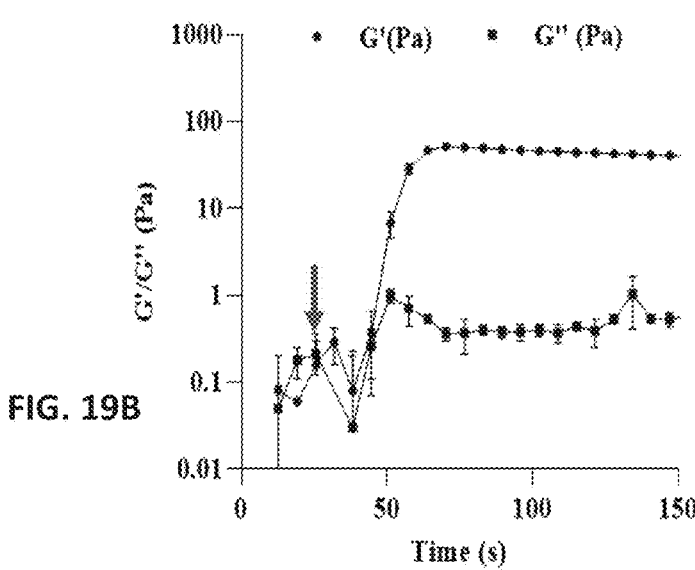
Figure 19C:
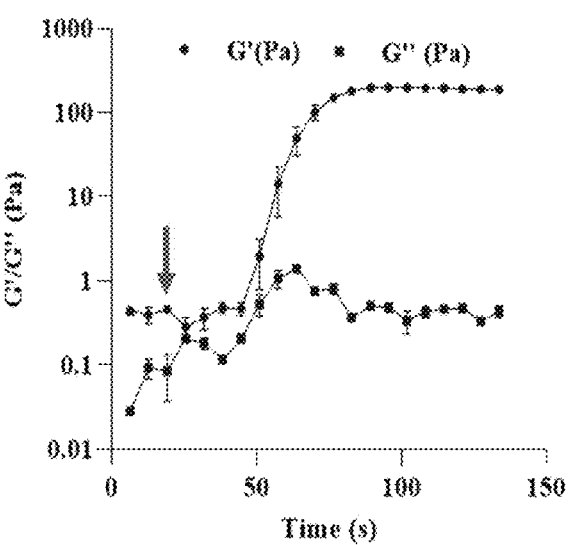
Figure 19D:
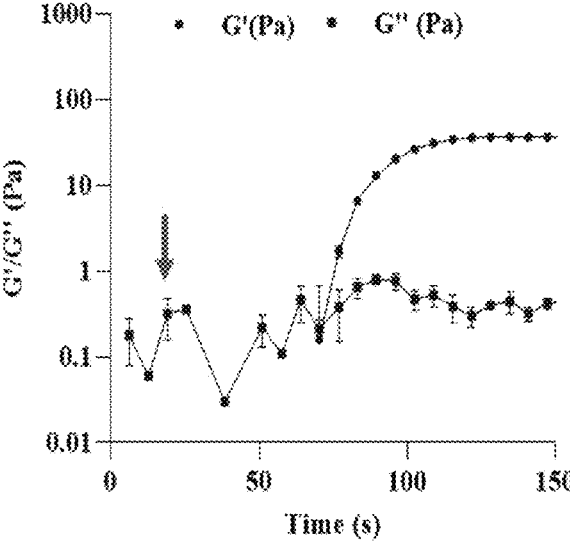
Figure 19E:
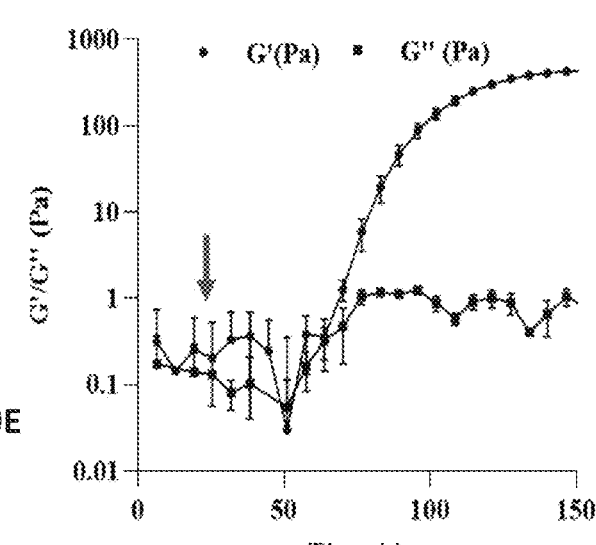
Figure 19F:
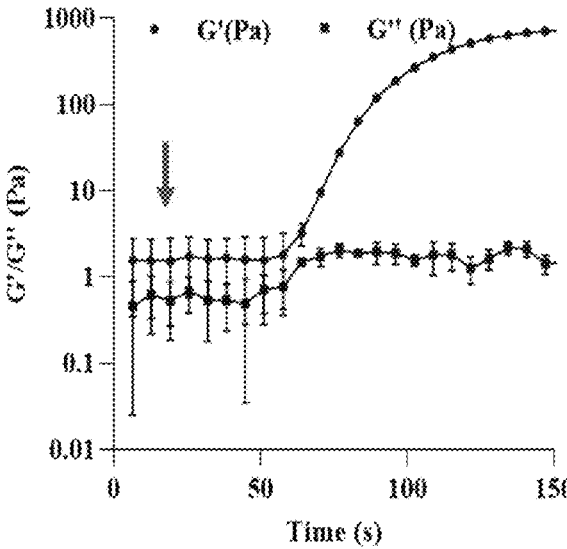

FIGS. 19A-F present shear storage modulus, G'(Pa), of hydrogels formed with different concentrations (w/v) of a PEG tetra-acrylate (PEG-TA) crosslinker alone (FIGS. 19A-C) and in the presence of 5 mg/ml FibMA$_{0.4\%}$ (FIGS. 19D-F). Red arrows indicate the beginning of polymerization by photoinitiation.

Figure 19G:
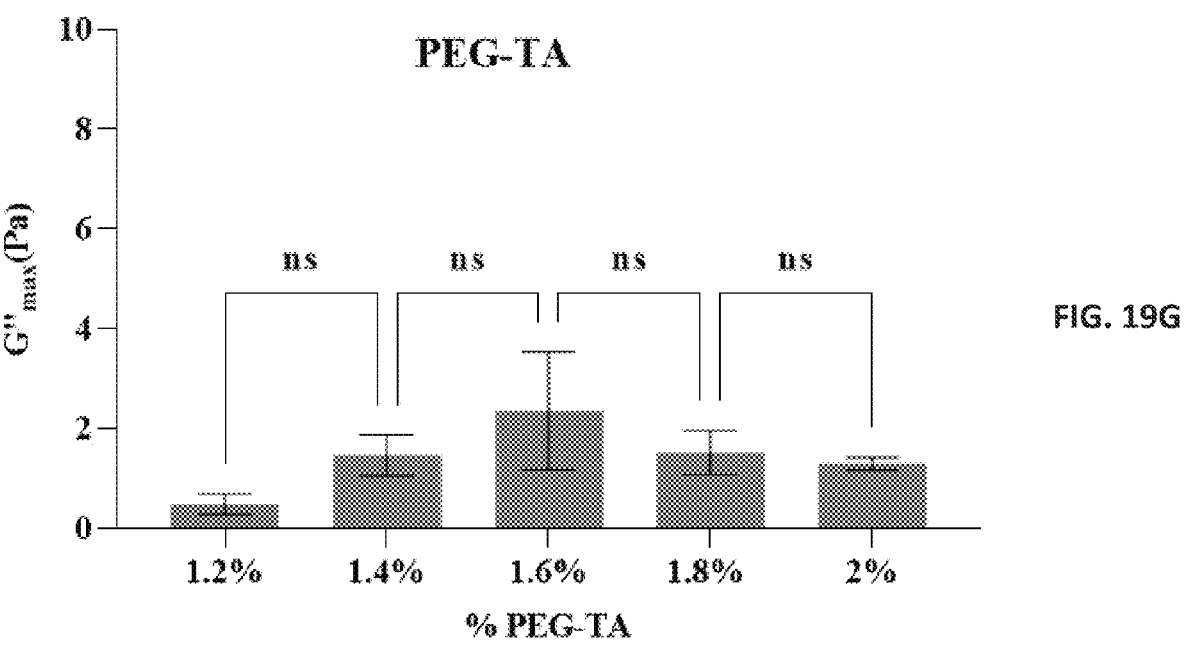
Figure 19H:
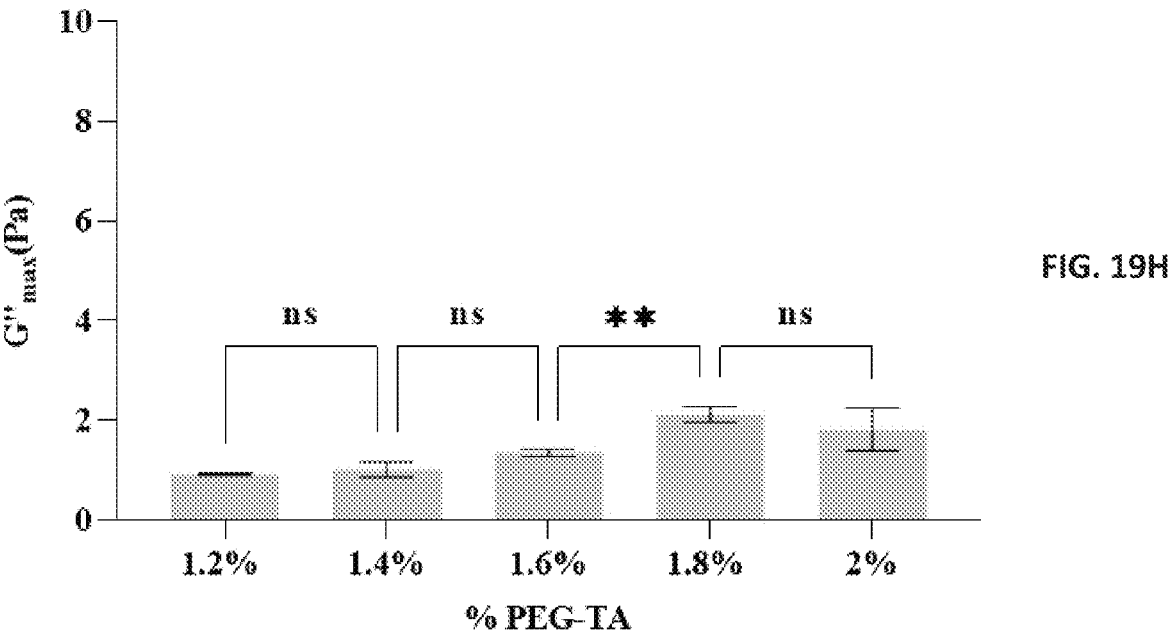

FIGS. 19G-H are bar graphs presenting the G"$_{max}$ values of the PEG-TA hydrogels shown in FIGS. 19A-C (FIG. 19G) and the G"$_{max}$ values for the FibMA$_{0.4\%}$+PEG-TA hydrogels shown in FIGS. 19D-F (FIG. 19H). "ns" indicates p>0.05,  indicates p<0.01 and ** indicates p<0.0001; values are given as mean±SD; n=3.

Figure 20A:
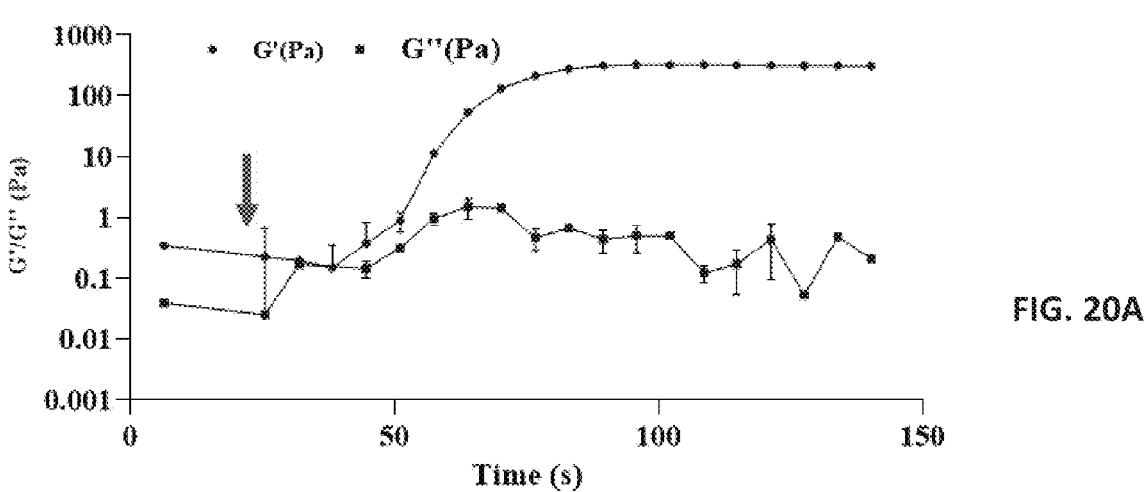
Figure 20B:
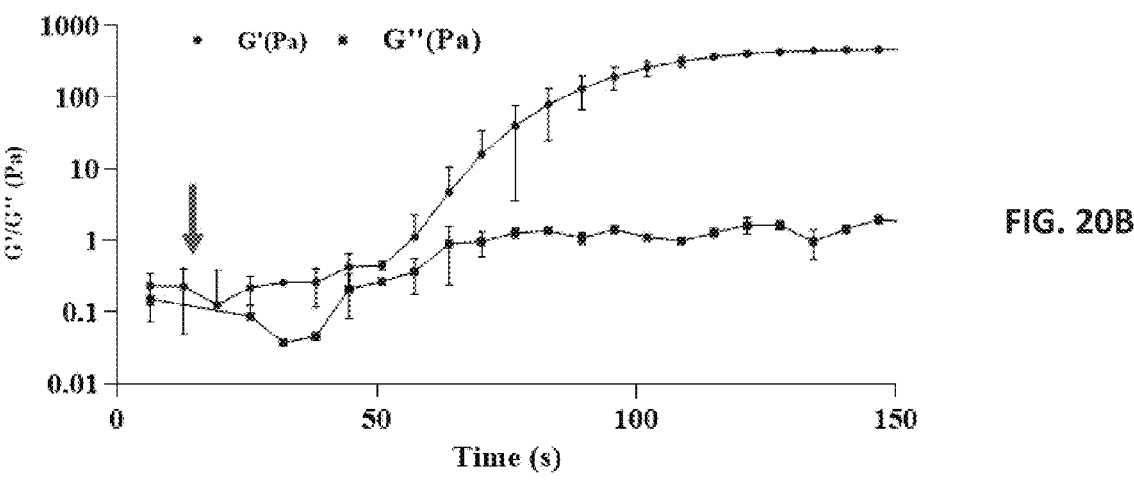
Figure 20C:
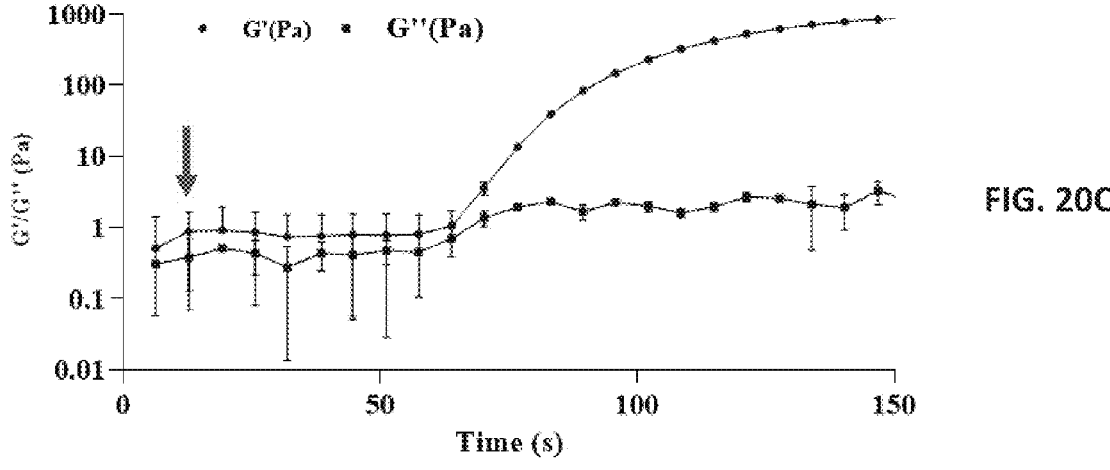

FIGS. 20A-C present the data obtained in rheological and kinetic measurements of hydrogel formation, while polymerizing hydrogel precursors on the rheometer, showing the shear storage modulus G'(Pa) and loss modulus G"(Pa) of the three formulations. The characterization was performed on formulations including 2% PEG-TA (FIG. 20A), 8 mg/ml FibMA$_{0.1\%}$ with 2% PEG-TA (FIG. 20B), and 8 mg/ml FibMA$_{0.4\%}$ with 2% PEG-TA (FIG. 20C). The samples were tested at room temperature; UV irradiation was initiated after 15 seconds (indicated by red arrow).

Figure 20D:
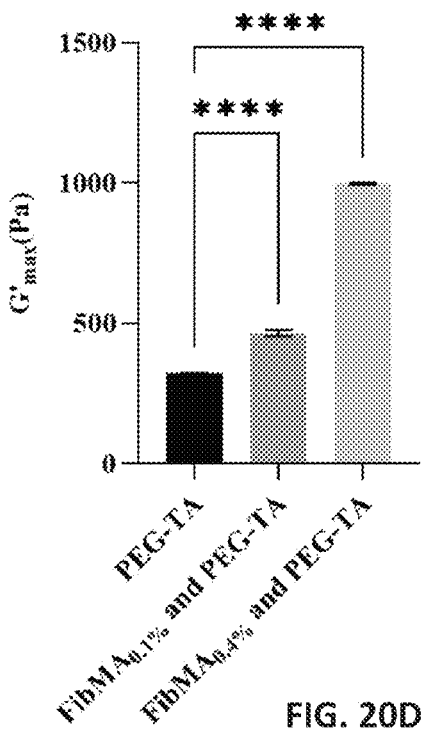
Figure 20E:
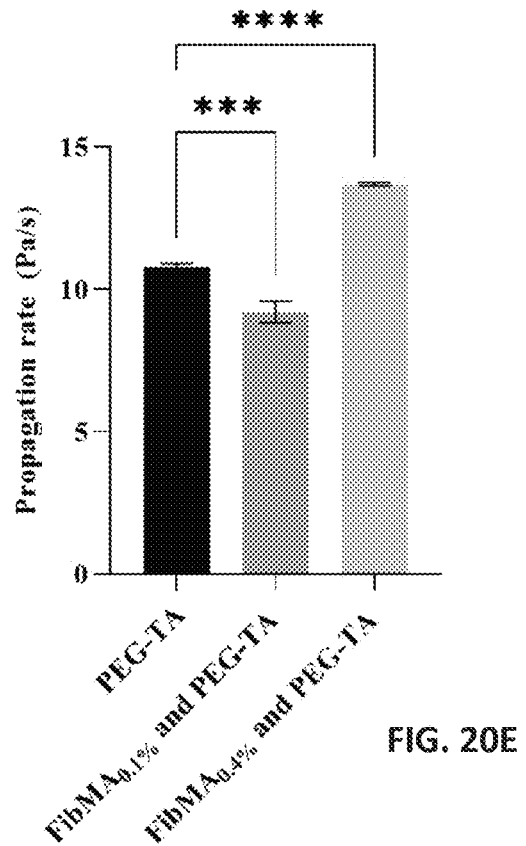
Figure 20F:
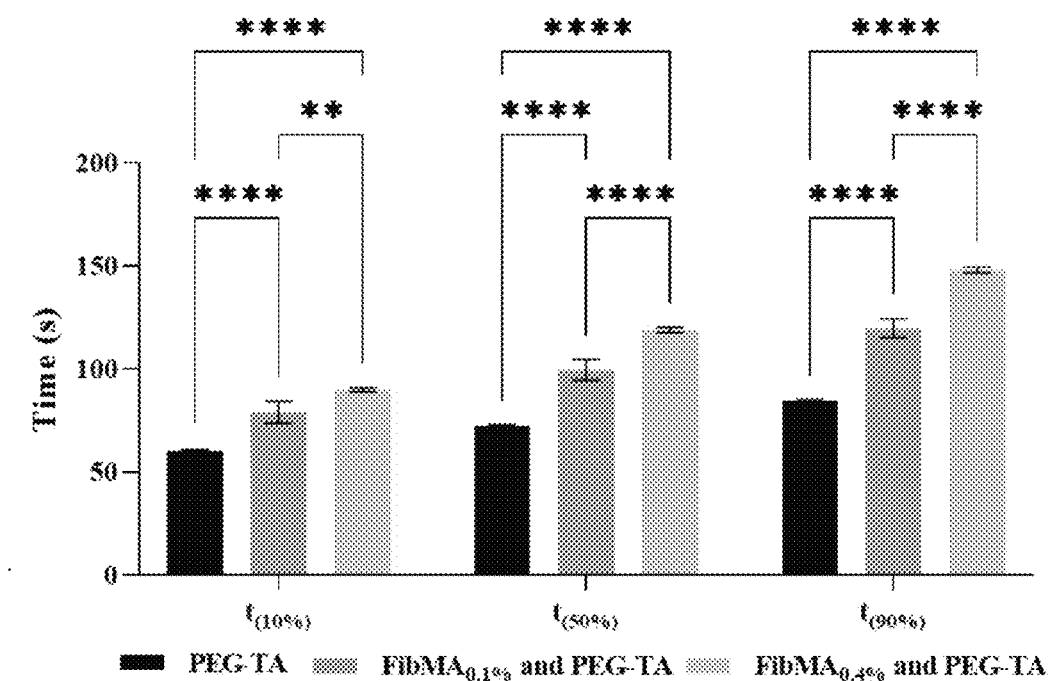

FIGS. 20D-F are bar graphs presenting the G'$_{max}$ values (FIG. 20D), the $t_{10}$, $t_{50}$ and $t_{90}$ values (FIG. 20E), and the propagation rate of the hydrogel formation (FIG. 20F) for the formulations presented in FIGS. 20A-C. * indicates p<0.05,  indicates p<0.01, * indicates p<0.001 and **** indicates p<0.0001; n=3.

Figure 21A:
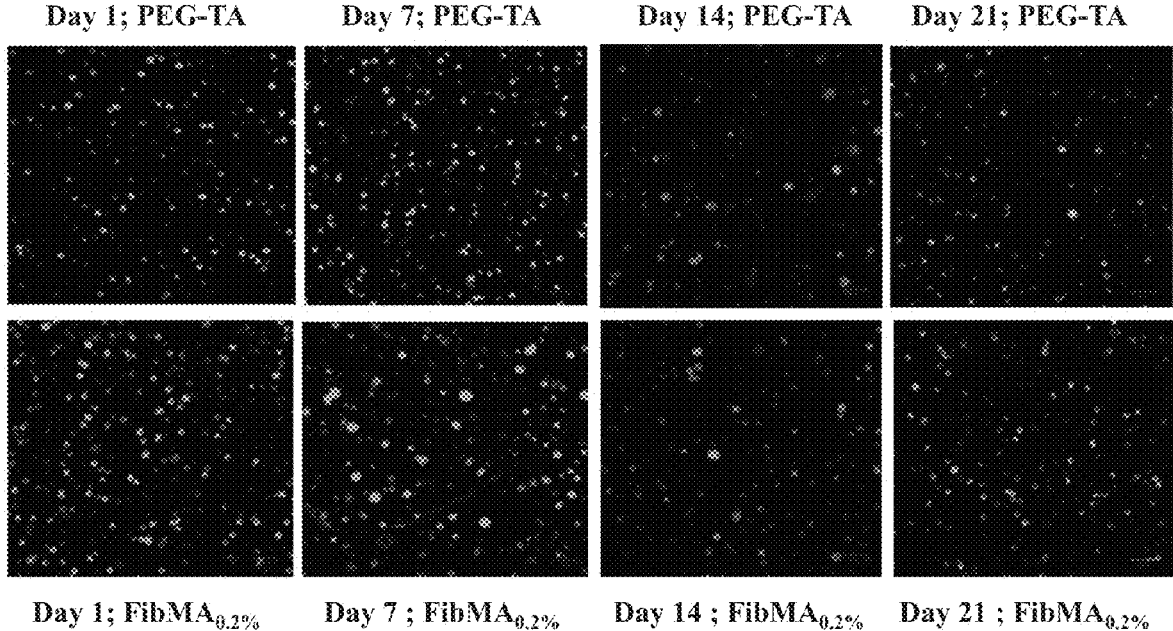
Figure 21B:
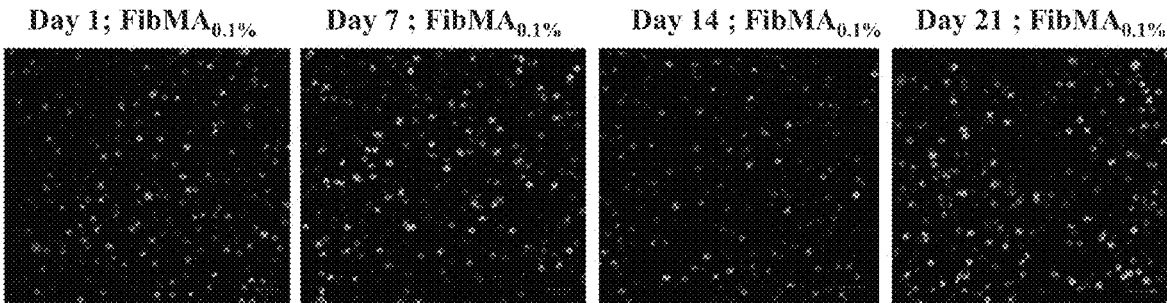

FIGS. 21A-B present fluorescence images of NHDF ($3*10^6$ cell/ml) encapsulated in FibMA$_{0.2\%}$, and PEG-TA (FIG. 21A) and FibMA$_{0.1\%}$ (FIG. 21B) hydrogels. wherein calcein (green) represents live cells, and ethidium (red) represents dead cells. Scale bar=50 μm.

Figure 21C:
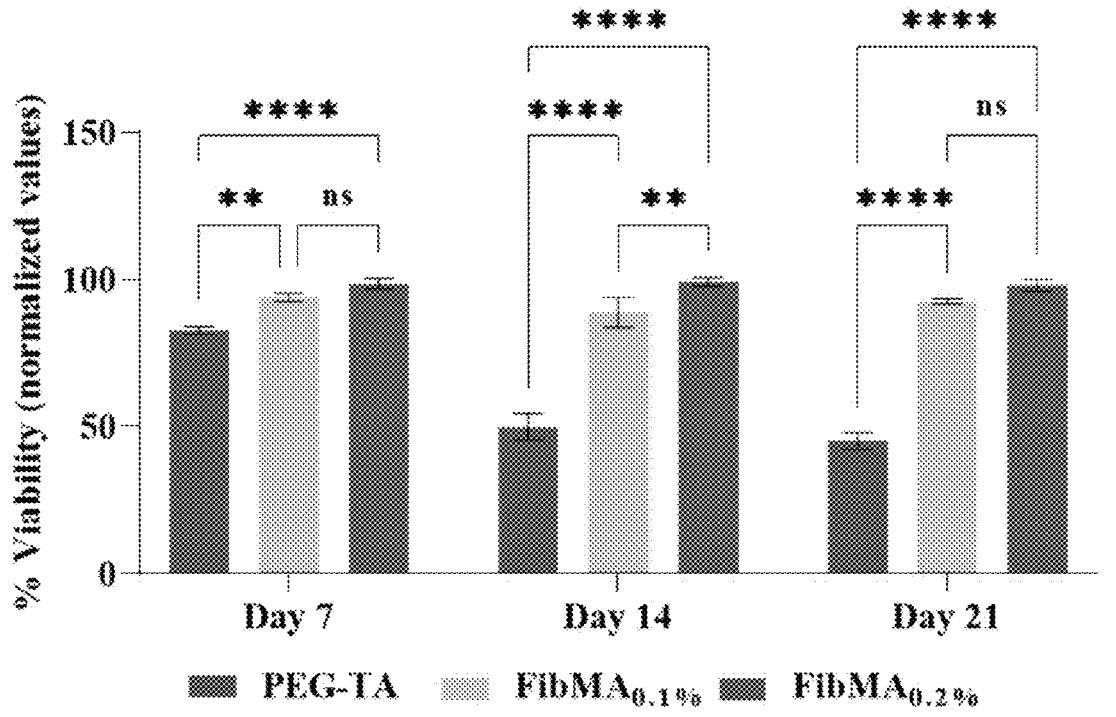
Figure 21D:
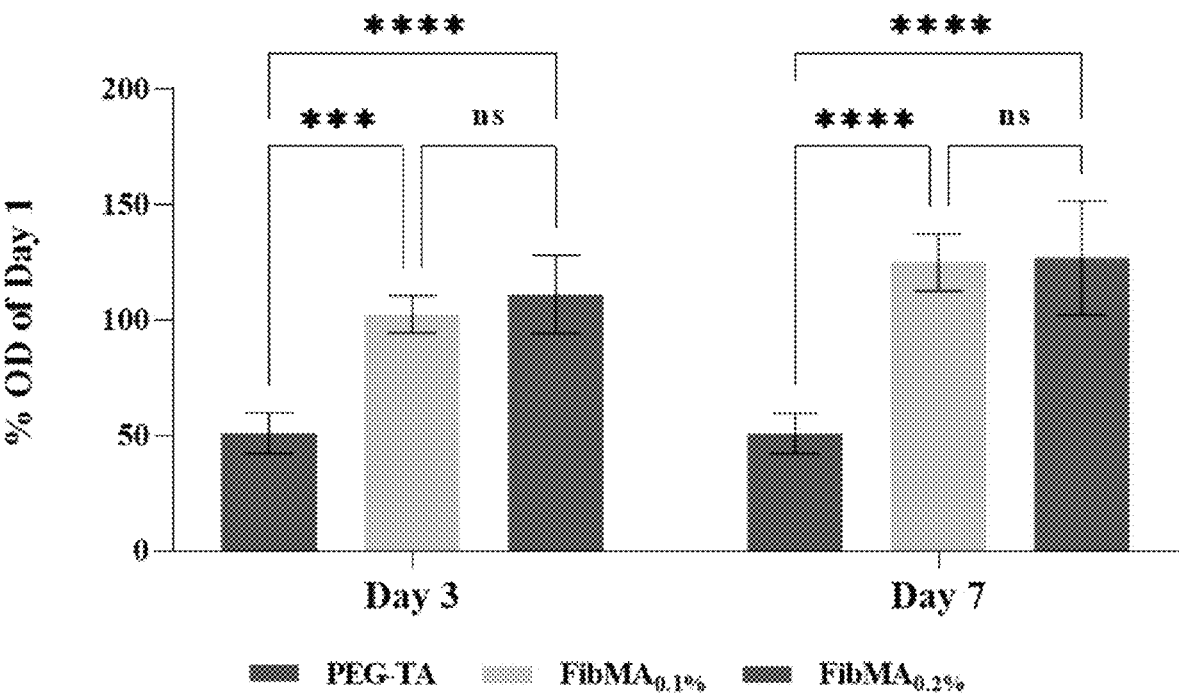

FIGS. 21C-D are bar graphs, showing the normalized viability percent of NHDF cells encapsulated in FibMA$_{0.2\%}$, FibMA$_{0.1\%}$ and PEG-TA (FIG. 21C) and the respective percent of OD at day 3 and day 7, normalized to day 1 (FIG. 21D). * indicates p<0.001 and ** indicates p<0.0001 and ns indicates not statically significant results p<0.05). The data are presented as the mean±SD, n≥3

Figure 21E:
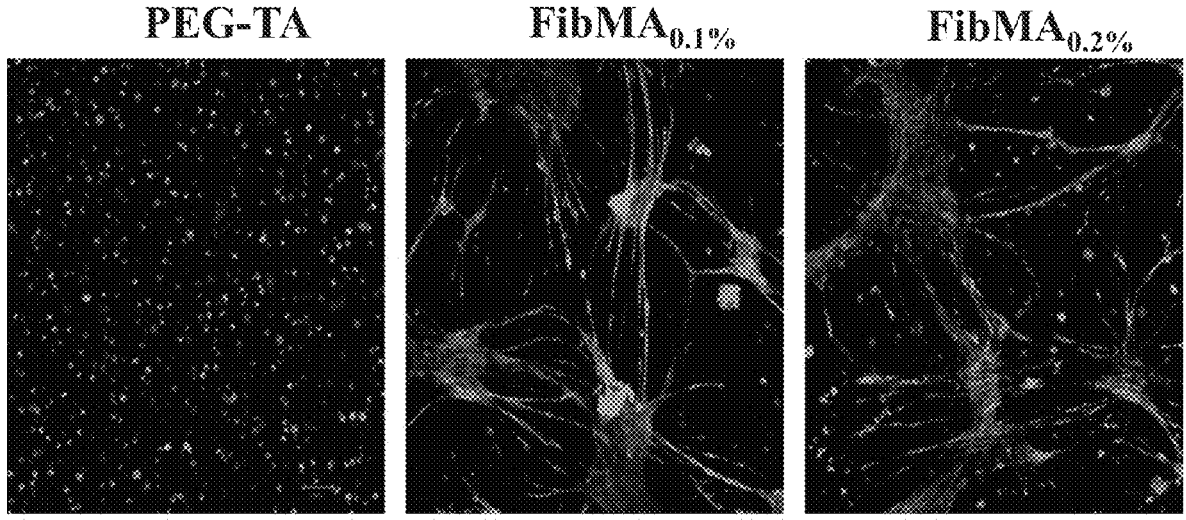

FIG. 21E presents fluorescence images of NHDF encapsulated in the PEG-TA (scale bar=50 μm), FibMA$_{0.1\%}$ (scale bar=100 μm), and FibMA$_{0.2\%}$, (scale bar=100 μm), hydrogels after 21 days in culture.

Figure 22A:
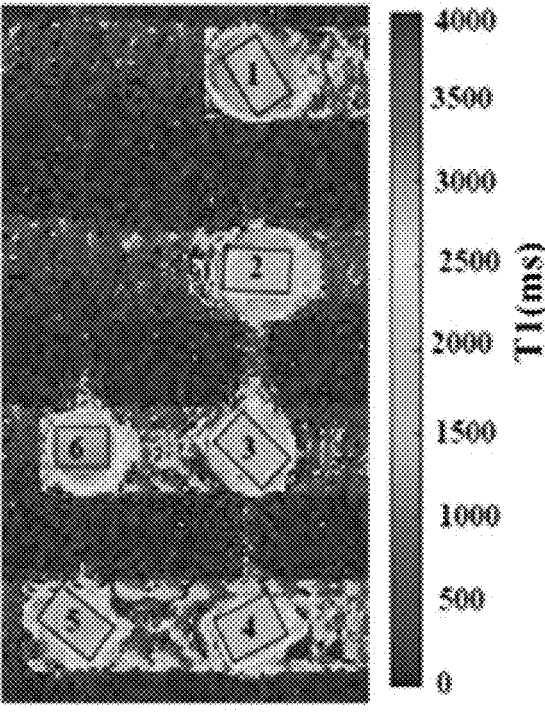
Figure 22B:
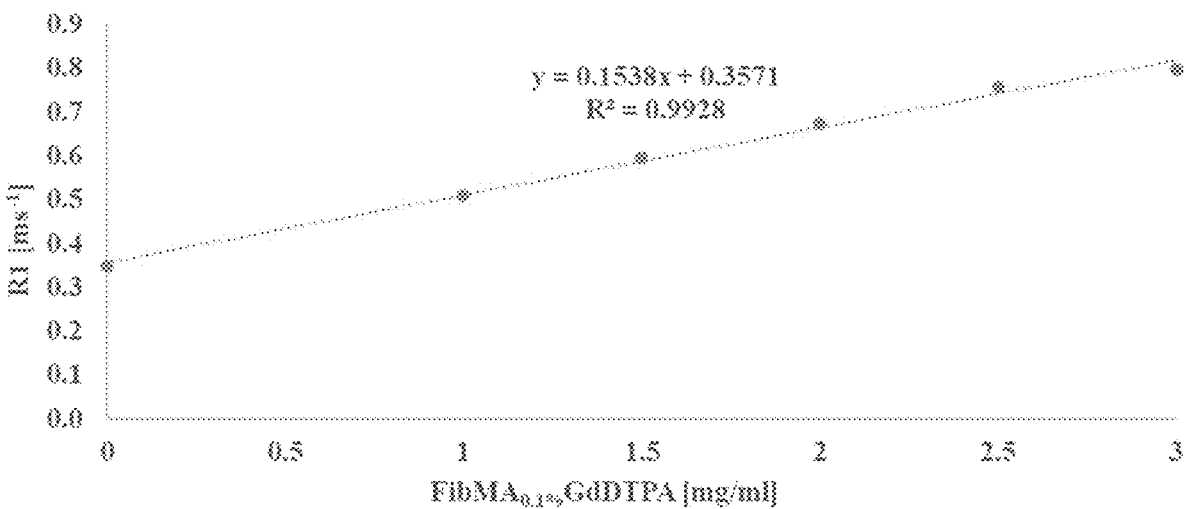

FIGS. 22A-B present a relativity color map of plugs containing different concentrations (0-3 mg/ml) of Gd-labelled FibMA (FibMA$_{0.1\%}$-GdDTPA; FIG. 22A) and a plot generated following the in vitro MRI calibration of FIG. 22A, showing R1 values of FibMA$_{0.1\%}$-GdDTPA as a function of concentration in the hydrogels (FIG. 22B), showing a linear correlation was found between R1 values and the FibMA$_{0.1\%}$-GdDTPA concentration.

FIGS. 23A-I are in vivo MR imaging of FibMA hydrogel plug constructs implanted subcutaneously on the backs of C57BL/6 mice, as imaged before implantation (FIG. 23A) and on consecutive days, as indicated in FIGS. 23B-I. The constructs contain 6 mg/ml FibMA$_{0.1\%}$, 2 mg/ml FibMA$_{0.1\%}$-GdDTPA and 1.5% PEG-TA. Red arrows indicate the plug implant location.

Figure 23J:
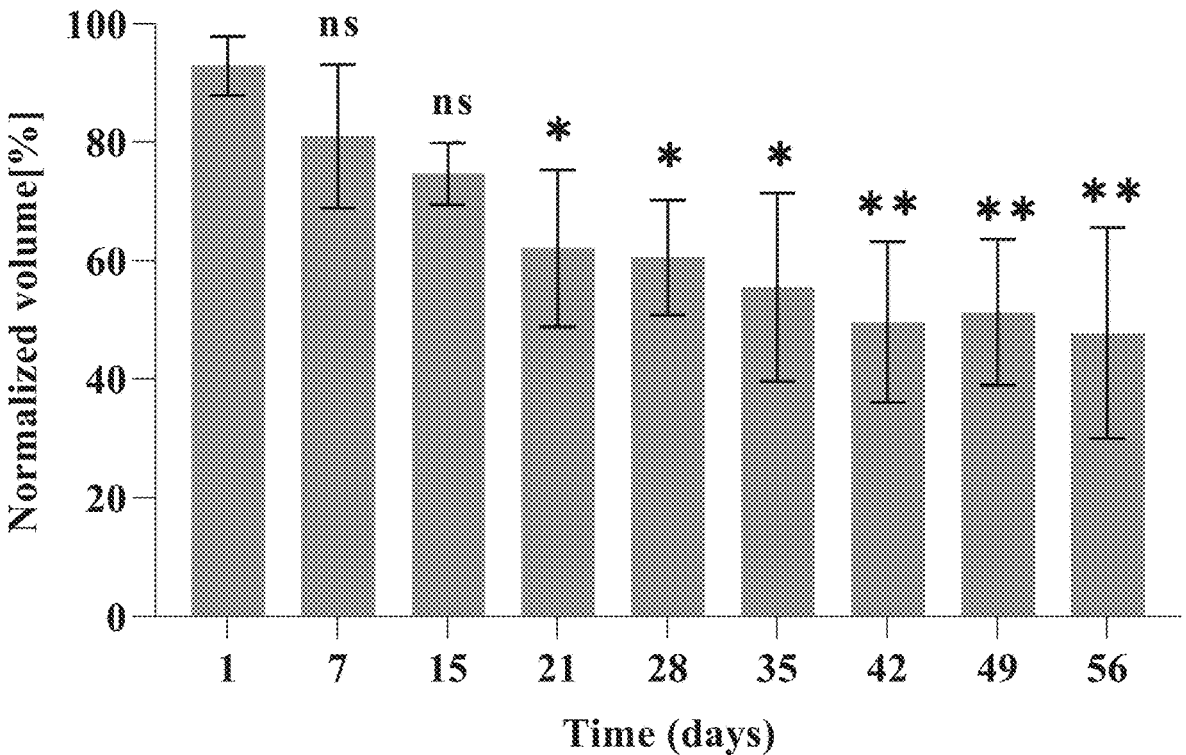

FIG. 23J are bar graphs presenting quantitative analysis of the implant volume up to week 8. The data are presented as the mean±SD.

Figures 24A, 24B, 24C:
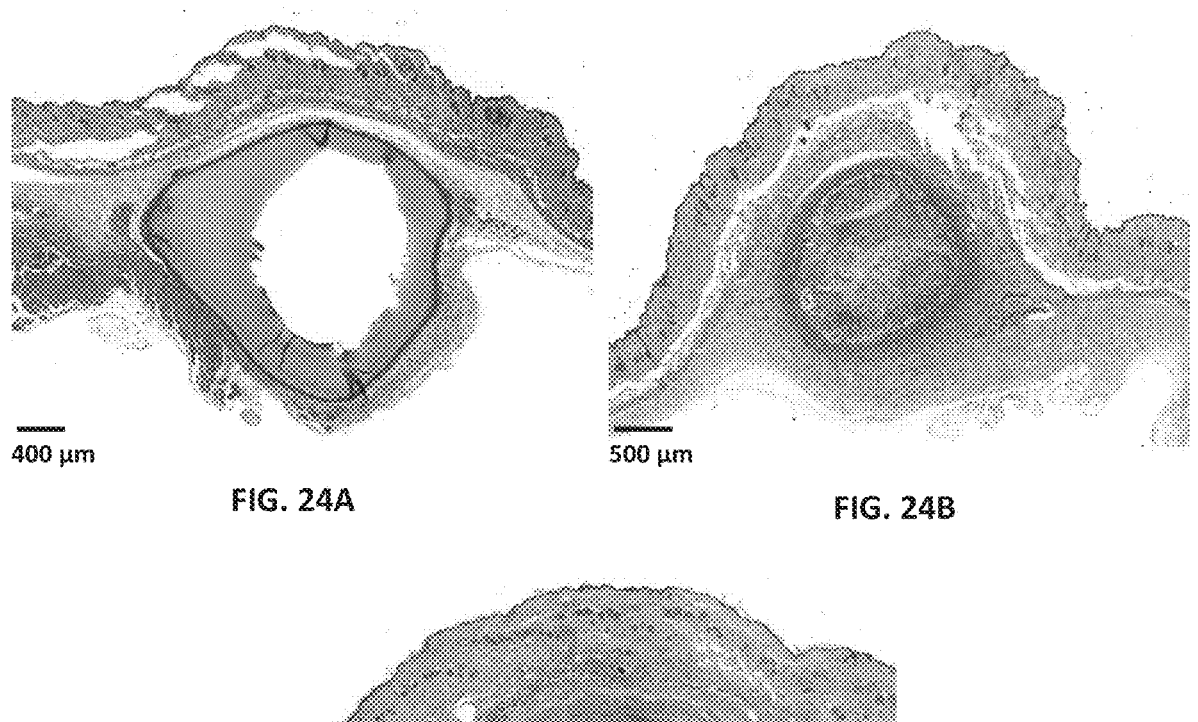

FIGS. 24A-C present images of histological cryosections of H&E-stained specimen taken from the implanted mice (as described for FIGS. 23A-I) at week 1 (FIG. 24A; scale bar=400 μm), week 3 (FIG. 24B; scale bar=500 μm), and week 8 (FIG. 24C; scale bar=500 μm), showing inflammatory response around the implant followed by resorption of the implant.

Figure 25:
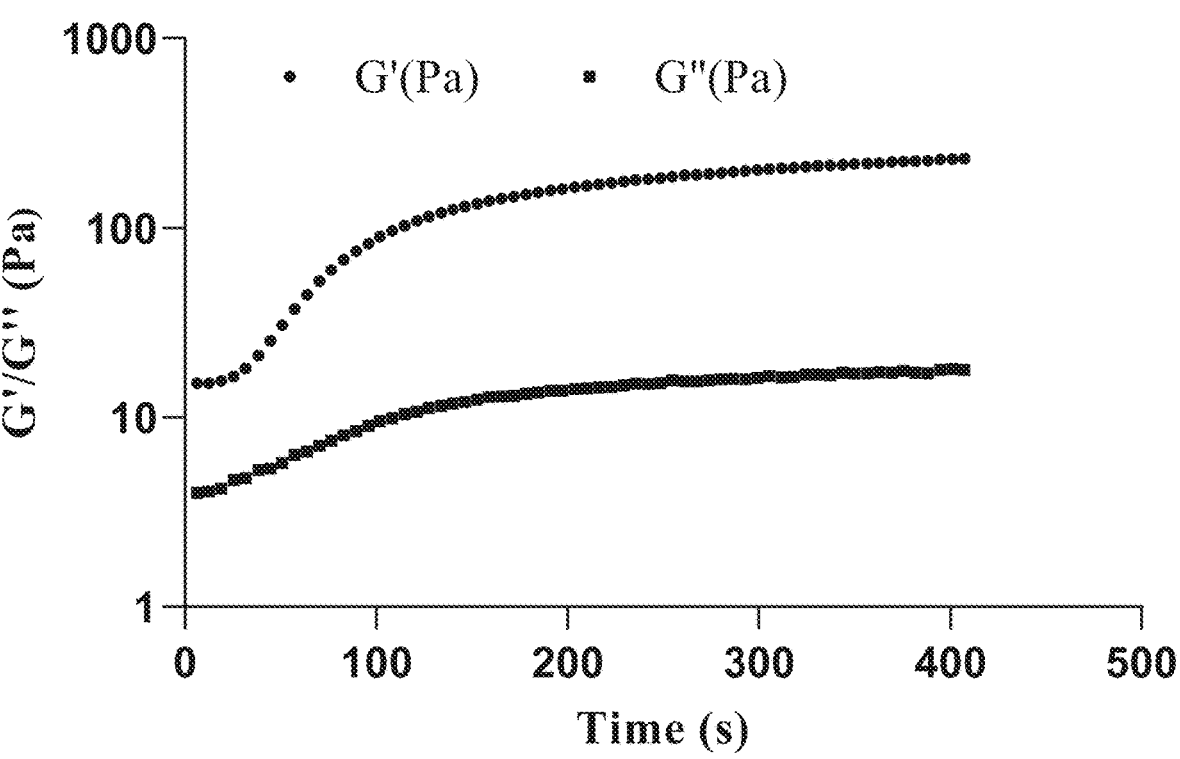

FIG. 25 presents plots showing the rheological properties of FibMA$_{0.2\%}$ (40 mg/ml) hydrogel under oscillatory shear. The FibMA$_{0.2\%}$ hydrogel was analyzed by a time sweep in oscillatory shear at a constant frequency of 2 Hz and an oscillation strain of 1%. The samples were tested at room temperature; UV irradiation was initiated after 15 seconds (indicated by red arrow).

Figure 26A:
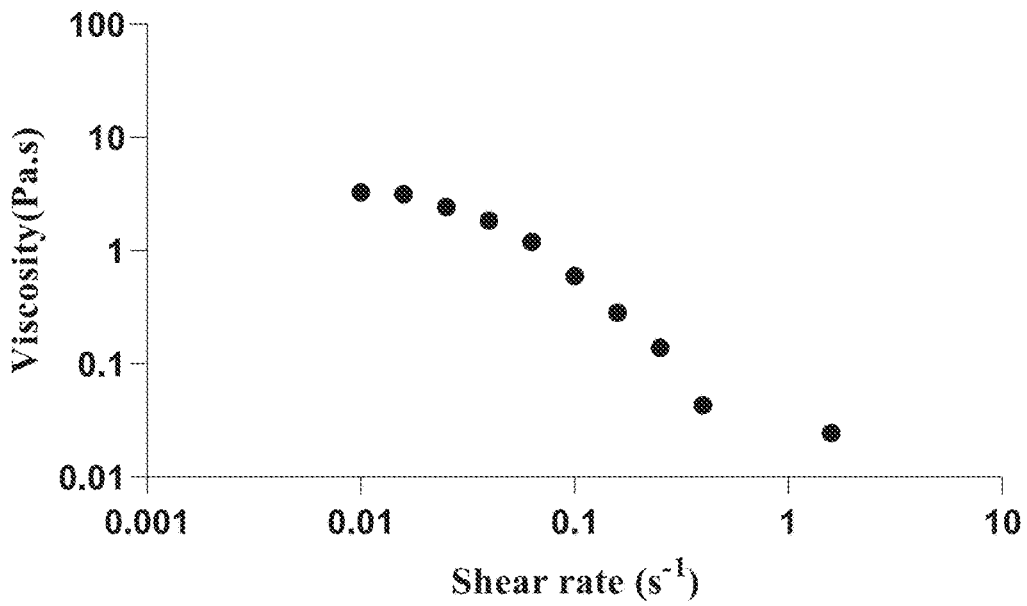
Figure 26B:
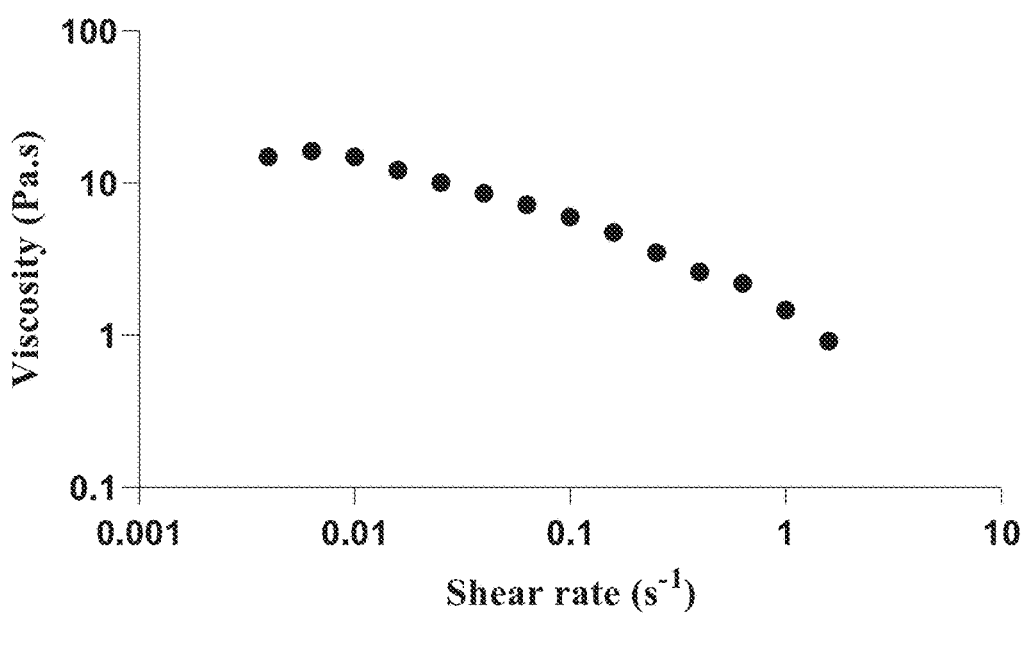

FIGS. 26A-B present data obtained in the viscosity measurements of FibMA$_{0.2\%}$ (40 mg/ml) (FIG. 26A) and FibMA$_{0.2\%}$ (10 mg/ml) (FIG. 26B) under increasing shear rate. The samples were tested at room temperature without UV irradiation. The viscosity was taken as the value at a shear rate of 0.01 s$^{-1}$.

DESCRIPTION OF SPECIFIC EMBODIMENTS OF THE INVENTION

The present invention, in some embodiments thereof, relates to biological materials and, more particularly, but not exclusively, to a curable fibrinogen, to curable formulations containing same, to scaffolds formed therefrom and to uses of curable fibrinogen, curable formulation and/or scaffold in, for example, tissue healing and/or regeneration.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Fibrinogen is the precursor to the commonly known blood clot protein, fibrin. The fibrinogen molecule is roughly 366 kDA, and is comprised of three polypeptide chains: alpha, beta and gamma. The fibrinogen polypeptides contain a set of biological cell-signaling cues specific to cellular remodeling, including the cell-adhesive sequence Arg-Gly-Asp (RGD) and a protease degradation substrate. Fibrinogen also contains roughly 34 residues of the lysine amino acid per each polypeptide chain. FIG. 1 presents a table summarizing the amino acid composition of the polypeptides chains of fibrinogen and fibrin.

According to some embodiments of the present invention there are provided newly designed materials for improving the versatility of fibrinogen hydrogel materials for biomedical applications. This family of materials can be used in the clinic through minimally invasive medical procedures owing to its injectability, or can be adapted as bioinks to the rapidly growing field of bioprinting.

The newly designed materials are based on coupling curable groups to the fibrinogen protein to thereby provide a curable conjugate, which enables a rapid hydrogel formation by either free radical polymerization or other covalent chemical reactions such as, for example, "click" chemistry. Exemplary embodiments relate to methacrylation of the fibrinogen protein (i.e., FibMA). The FibMA conjugate according to these exemplary embodiments is the basis of a scaffold (e.g., a hydrogel) that is created by free radical polymerization.

Some embodiments of the present invention relate to a novel biodegradable hydrogel scaffold formed of a fibrinogen conjugate that features a plurality of curable groups (e.g., methacrylated fibrinogen), upon exposure to a suitable curing condition (e.g., irradiation). According to some embodiments, the hydrogel is an injectable hydrogel and can be implemented as an acellular matrix or as a cellularized scaffold using minimally invasive techniques of administration. The bioactive characteristics of the scaffold promote cell invasion from tissues, as well as support the survival of cells that are encapsulated in the scaffold. The physical, biodegradation and mechanical properties can be controlled by altering the amount of curable groups in the fibrinogen conjugate (e.g., the degree of methacrylation) or by introducing different amounts of additional cross-linking agents (e.g., multifunctional polymeric cross-linking agent) to a curable formulation that comprises the conjugate. The efficacy of this approach has been demonstrated using multiple characterization techniques and in vitro cell culture studies. The findings clearly demonstrate that the new materials can be used as a scaffold for cells, particularly in medical applications that require tissue healing and regeneration. The future applications of this technology may extend beyond the regenerative medicine arena to include such applications as biosensors, biotechnology and diagnostics.

According to some embodiments of the present invention there is provided a scaffold or a three-dimensional object made of a curable conjugate as described herein, and also provided are processes of preparing the scaffold by exposing the conjugate or a formulation containing same to a suitable curing condition. An exemplary such a process is additive manufacturing (e.g., bioprinting).

The fibrinogen constituent provides bioactive motifs for cell adhesion and proteolytic degradation. Control over mechanical properties and biodegradation is afforded by the amount of curable groups (e.g., the degree of methacrylation) on the fibrinogen backbone. The curable conjugate can be formed into a 3-D matrix in the presence of biological materials such as, for example, growth factors, cells, DNA, RNA and/or other bioactive constituents. The matrix can, for example, then be implanted locally to mediate local, sustained release of the bioactive payload. The degradation of the matrix in mediated in vivo by the production of enzymes as well as by non-specific hydrolysis of the methacrylated side chains. Once the matrix (scaffold) is degraded, the bioactive payload is released and can have inductive properties, for example, in tissue healing and regeneration.

This new injectable hydrogel can be implemented as an acellular matrix or as a cellularized scaffold using minimally invasive techniques of administration. The bioactive characteristics of the scaffold promote cell invasion from tissues, as well as support the survival of cells that are encapsulated in the scaffold. The physical, biodegradation and mechanical properties can be controlled by altering the amount of curable groups (e.g., degree of methacrylation) or by introducing different amounts of additional cross-linking agents to the curable formulation containing the conjugate.

Embodiments of the present invention relate to an injectable formulation that comprises a curable conjugate as described herein (e.g., methacrylated fibrinogen) that can form a biodegradable scaffold (e.g., hydrogel). In exemplary embodiments, methacrylated fibrinogen (FibMA) hydrogel precursors are prepared by conjugating methacrylic groups at least to the free amines on fibrinogen lysines. The formation of the FibMA hydrogels was demonstrated using a radical polymerization reaction. The biodegradation and mechanical properties of the hydrogel material were characterized and reported as a function of the composition of the FibMA hydrogels, including degree of fibrinogen methacrylation and addition of functionalized polymeric cross-linker. The FibMA hydrogel was formed in the presence of cells to create a cell-laden scaffold. The hydrogel was also formed in the presence of cellularized tissue constructs to evaluate cell invasion into the FibMA matrix. The bioactive properties of the FibMA scaffold were demonstrated using in vitro characterizations of the cells, including through viability and morphological assessments.

Conjugate:

According to an aspect of some embodiments of the present invention there is provided a conjugate comprising fibrinogen and a plurality of curable groups covalently attached to the fibrinogen. The conjugate is also referred to herein as "curable fibrinogen".

By "curable" it is meant herein a material that is capable of undergoing curing, or hardening (e.g., a substantial change in viscosity and/or shear modulus), when exposed to a suitable curing condition.

A curable material is typically hardened or cured by undergoing polymerization and/or cross-linking.

Curable materials are typically polymerizable materials, which undergo polymerization and/or cross-linking when exposed to a suitable curing condition (e.g., a suitable curing energy or a suitable energy source). The curable materials can alternatively or in addition be thermo-responsive materials, which solidify or harden upon exposure to a temperature change (e.g., heating or cooling) as the curing condition.

In some of any of the embodiments described herein, a curable material is a photopolymerizable material, which polymerizes and/or undergoes cross-linking upon exposure to radiation, as described herein, and in some embodiments the curable material is a UV-curable material, which polymerizes or undergoes cross-linking upon exposure to UV-vis radiation, as described herein.

In some of any of the embodiments described herein, when a curable material is exposed to a curing condition (e.g., radiation), it polymerizes by any one, or combination, of chain elongation, entanglement and cross-linking. The cross-linking can be chemical and/or physical.

In some of any of the embodiments described herein, a curable material can be a mono-functional curable material or a multi-functional curable material.

Herein, a mono-functional curable material comprises one curable group.

By "curable group" it is meant a functional group that can undergo polymerization, entanglement and/or cross-linking when exposed to a curing condition (e.g., radiation, heat, presence of a chemical reagent).

A multi-functional curable material comprises two or more, e.g., 2, 3, 4 or more, curable groups. Multi-functional curable materials can be, for example, di-functional, tri-functional or tetra-functional curable materials, which comprise 2, 3 or 4 curable groups, respectively.

By "curable fibrinogen" or "curable conjugate" or simply a "conjugate" it is meant a fibrinogen as described herein in any of the respective embodiments, which features one or more curable groups as defined herein. According to some embodiments, the one or more curable groups are covalently attached to the fibrinogen. According to some of any of the embodiments described herein, the curable fibrinogen is a multi-functional curable material that comprises a plurality (e.g., two or more) of curable groups, as defined herein, that is, the fibrinogen has a plurality curable groups, as defined herein, covalently attached thereto.

By "fibrinogen" it is meant the whole fibrinogen polypeptide (α, β and/or γ chains of fibrinogen) or a fragment (portion) thereof. Optionally, the conjugate described herein comprises the α, β and γ chains of fibrinogen. In exemplary embodiments, the conjugate comprises a denatured fibrinogen (e.g., a mixture of denatured α, β and γ chains of fibrinogen), having a plurality of curable groups attached thereto, as described herein.

A human fibrinogen comprises α-chain—GenBank Accession No. NP_068657; β-chain—GenBank Accession No. P02675; and γ-chain—GenBank Accession No. P02679.

When a portion of the fibrinogen is used, it preferably includes sufficient biodegradability potential, e.g., it acts as a protease substrate and/or protease target, as well as sufficient cell signaling and/or cell adhesion motives. For example, the human fibrinogen protein contains two RGD adhesion sites at amino acids 114-116 and 591-593 of the α-chain (GenBank Accession No. NP_068657), as well as a protease cleavage site at amino acids 44-45 of the β-chain (GenBank Accession No. P02675).

According to some of any of the embodiments described herein, the curable fibrinogen features one or more, preferably a plurality of, curable groups generated from at least a portion of the amino acid residues forming the fibrinogen, preferably by covalent attachment of a compound that comprises a curable group to functional groups of the side chains of the amino acid residues. Alternatively, or in addition, curable groups can be generated at the N-terminus and/or C-terminus of one or more the units forming the fibrinogen, for example, by covalent attachment of a compound that comprises a curable group to a respective amine or carboxylate.

According to some of any of the embodiments described herein, at least a portion of the curable groups in a curable fibrinogen as described herein are cross-linkable groups, which can undergo cross-linking when exposed to a suitable curing condition, to thereby form a three-dimensional structure.

In some embodiments, the curable groups can undergo polymerization and/or cross-linking via free-radical mechanism.

Exemplary such curable groups include acrylic groups, including acrylate, methacrylate, acrylamide and methacrylamide groups. Other free-radical curable groups may include thiols, vinyl ethers and other groups that feature a reactive double bond.

In some embodiments, the curable groups can undergo polymerization and/or cross-linking via other mechanisms, such as cationic polymerization, or (cationic or anionic) ring opening polymerization. Exemplary such curable groups include, but are not limited to, epoxy-containing groups, caprolactam, caprolactone, oxetane, and vinyl ether.

Other curable groups can include, for example, formation of amide bonds between functional carboxylate and amine group (each being a curable group that reacts with the other and can effect cross-linking); formation of urethane between isocyanate groups and hydroxyl groups via polycondensation in the presence of a catalyst and/or upon exposure to UV radiation; and formation of disulfide bonds between two thiols.

Any other curable groups are contemplated.

The curable groups in the curable fibrinogen can be generated by means of chemical reactions between a material that comprises or can generate the curable group(s) when reacted with chemically-compatible (e.g., intrinsic) functional groups present in the fibrinogen, as described herein, either directly, or by means of a spacer or a linker, using chemistries well known in the art. For example, a material that comprises a curable group and a functional group can be reacted with a compatible functional group in the fibrinogen, for example, a functional group in an amino acid side chain, such that the curable group is a substituent of the amino acid side chain.

In some embodiments, a compatible functional group is first generated within the fibrinogen by chemical modification of chemical groups of the fibrinogen (e.g., chemical groups at the side chain of amino acid residues), and is than reacted with a material that comprises or generates a curable group upon the reaction.

Whenever a curable fibrinogen comprises more than one curable group, the curable groups can be the same of different.

According to some of any of the embodiments described herein, at least a portion, or all, of the curable groups in a curable fibrinogen of the present embodiments are photo-polymerizable groups (e.g., UV-curable groups) that are capable of undergoing polymerization and/or cross-linking upon exposure to irradiation as described herein.

According to some of any of the embodiments described herein the curable group is a photocurable or photopolymerizable group (e.g., an acrylate or methacrylate, or acrylamide or methacrylamide, which are collectively referred to as "acrylic groups").

According to some of any of the embodiments described herein, at least a portion, or all, of the curable groups in a curable fibrinogen of the present embodiments are acrylic groups, as defined herein.

According to some of any of the embodiments described herein, an acrylic group such as methacrylamide can be generated by reacting an acrylate or methacrylate (e.g., acrylic acid, methacrylic acid, acrylic or methacrylic ester, acrylic or methacrylic anhydride) with an amine functional group (of, for example, lysine residues).

According to some of any of the embodiments described herein, an acrylic group such as methacryloyl can be generated by reacting an acrylate or methacrylate (e.g., acrylic acid, methacrylic acid, acrylic or methacrylic ester, acrylic or methacrylic anhydride) with a hydroxy functional group (of, for example, serine and/or threonine residues).

According to some of any of the embodiments described herein, the curable fibrinogen features a plurality of acrylic groups generated by reacting an acrylate or methacrylate (e.g., acrylic acid, methacrylic acid, acrylic or methacrylic ester, acrylic or methacrylic anhydride) with both, one or more amine functional group(s) (of, for example, lysine residues) and one or more hydroxy functional group(s) (of, for example, serine and/or threonine residues).

According to some of any of the embodiments described herein, the curable fibrinogen has a plurality of acrylic groups covalently attached thereto via side chains of amino acid residues therein, for example, by forming acrylamide and/or acryloyl groups.

According to some of any of the embodiments of the present invention, the number of the curable groups in a curable fibrinogen as described herein can determine the degree of curing (e.g., the degree of cross-linking) and can be manipulated in order to achieve a desired curing (e.g., cross-linking) degree.

According to some of any of the embodiments described herein, the curable fibrinogen features a plurality of acrylamide or methacrylamide curable groups generated by reacting an acrylic material with lysine residues as described herein.

According to some of any of the embodiments described herein, the curable fibrinogen features a plurality of acrylamide or methacrylamide curable groups substituting the amine groups of lysine residues in the fibrinogen.

According to some of any of the embodiments described herein, the curable group can be attached to a respective amino acid residue either directly or via a linker. The linker can be, for example, an alkylene chain, or a hydrocarbon, as defined herein. According to some of any of the embodiments described herein, at least a portion, or each, of the curable groups are attached directly to respective amino acid residues of the fibrinogen. According to some of any of the embodiments described herein, at least a portion, or each, of the curable groups are attached to respective amino acid residues via a linker, as described herein, and the linker is other than poly(alkylene glycol) or is non-polymeric. In exemplary embodiments, the linker is a non-polymeric hydrocarbon or an alkylene chain.

According to some of any of the embodiments described herein, at least 10%, or least 20%, or least 30%, or at least 40%, or at least 50%, or at least 60%, or at least 70%, of the amino acid residues in the fibrinogen or the fragment thereof are each independently substituted by a curable group (e.g., a photopolymerizable group). In some embodiments, the curable fibrinogen features from 10 to 50%, or from 10 to 100%, or from 20 to 50%, or from 25 to 50%, or from 20 to 100%, or from 25 to 100%, or from 20 to 70%, or from 25 to 75%, or from 50 to 100%, or from 60 to 100%, or from 70% to 100%, or from 80% to 100%, or from 90% to 100%, of its residues substituted by a curable group, including any intermediate values and subranges therebetween.

According to some of any of the embodiments described herein, at least 10%, or least 20%, or least 30%, or at least 40%, or at least 50%, or at least 60%, or at least 70%, of the lysine residues in the fibrinogen are substituted by a meth-acrylamide or acrylamide group. In some embodiments, the curable fibrinogen features from 10 to 50%, or from 10 to 100%, or from 20 to 50%, or from 25 to 50%, or from 20 to 100%, or from 25 to 100%, or from 20 to 70%, or from 25 to 75%, or from 50 to 100%, or from 60 to 100%, or from 70% to 100%, or from 80% to 100%, or from 90% to 100%, of its lysine residues substituted by a methacrylamide or acrylamide group, including any intermediate values and subranges therebetween. According to some of these embodiments, other amino acid residues are substituted by an acrylic group as described herein.

According to an aspect of some embodiments of the present invention there is provided a process of preparing a curable fibrinogen as described herein. The process is effected, in some embodiments, by reacting a material that comprises a curable group or which generates a curable group in the fibrinogen, in accordance with the embodiments described herein.

The number of curable groups in the fibrinogen can be controlled by manipulating the amount of the material reacted with the fibrinogen for generating the curable groups.

In some embodiments, the material is used in a molar excess with respect to the respective functional groups that are reacted therewith, for example, in a mol ratio of 2:1, 5:1, 10:1, 15:1, 20:1 30:1, 50:1, or, for example, from 1.1:1 to 50:1, including any intermediate values and subranges therebetween, with respect to the chemically compatible functional groups in the fibrinogen (e.g., the amino acid residues featuring such functional groups, for example, lysine), or with respect to the fibrinogen.

According to exemplary embodiments, the material that is reacted for generating the curable groups is an acrylic material that features a reactive group that can chemically react with a chemically compatible group of the collagen as described herein. In exemplary embodiments, the reactive (functional) group is an acrylic anhydride, which can react with either one or both of amine groups (e.g., of lysine residues) and hydroxy groups (e.g., of serine and/or threonine residues) to thereby attach a respective acrylic group directly to the respective amino acid residue.

A conjugate as described herein can further comprise other moieties associated therewith, such as, but not limited to, a labeling agent, as described herein, a targeting moiety, a therapeutically active agent, and any other moiety, as desired. In some embodiments, the additional moiety is attached to the conjugate via chemical bonds (e.g., covalent bonds), for example, to one or more of the amino acid residues (via the side chain), or to one or more of the C-terminus or the N-terminus.

According to some of any of the embodiments described herein, the curable fibrinogen further comprises a labeling agent attached thereto. According to some of these embodiments, the labeling agent is covalently attached to the fibrinogen (or a fragment thereof). According to some of these embodiments, the labeling agent is covalently attached to one or more amino acid residues of the fibrinogen (or a fragment thereof) and/or to the C-terminus and/or the N-terminus of the polypeptide.

As used herein, the phrase "labeling agent" describes a detectable moiety or a probe. Exemplary labeling agents which are suitable for use in the context of these embodiments include, but are not limited to, a fluorescent agent, a radioactive agent, a magnetic agent, a chromophore, a bioluminescent agent, a chemiluminescent agent, a phosphorescent agent and a heavy metal cluster.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}Tc$, $^{18}F$, $^{131}I$ and $^{125}I$.

The term "magnetic agent" describes a substance which is attracted to an externally applied magnetic field. These substances are commonly used as contrast media in order to improve the visibility of internal body structures in Magnetic Resonance Imaging (MRI). The most commonly used compounds for contrast enhancement are gadolinium-based. MRI contrast agents alter the relaxation times of tissues and body cavities where they are present, which, depending on the image weighting, can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process The term "chemiluminescent agent" describes a substance which emits light as the result of a chemical reaction.

The phrase "fluorescent agent" refers to a compound that emits light at a specific wavelength during exposure to radiation from an external source. Exemplary such labeling agents include agents that emit light at the Near IR range (e.g., cyanines).

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

According to some of any of the embodiments described herein, the fibrinogen is denatured fibrinogen.

According to some of any of the embodiments described herein, the fibrinogen is denatured human fibrinogen.

According to some embodiments, the conjugate is devoid of a polymeric moiety.

According to some embodiments, the curable groups are attached directly to the fibrinogen or are attached to the fibrinogen via a linking group which is non-polymeric.

According to some embodiments, the curable groups are attached to the fibrinogen via a linking group which is other than poly(alkylene glycol).

According to some of any of the embodiments described herein, at least a portion, or all, of the curable groups are photopolymerizable (e.g., UV-curable) groups.

According to some of any of the embodiments described herein, at least a portion, or all, of the curable groups are (meth)acrylic groups.

According to some of any of the embodiments described herein, at least a portion, or all, of the curable groups are attached to lysine residues of the fibrinogen.

According to some of any of the embodiments described herein, at least a portion, or all, of the curable groups are attached directly to the fibrinogen.

According to some of any of the embodiments described herein, at least a portion, or all, of the curable groups are attached directly to the lysine residues (e.g., via an amide bond, forming a plurality of acrylamide curable groups).

According to some of any of the embodiments described herein, the curable groups are attached to 10 to 100% of the lysine residues, including any intermediate values and subranges therebetween. As demonstrated in the Examines section that follows, the % of lysine residues that have a curable group attached thereto may affect the mechanical and/or rheological properties of the conjugate, of a formulation comprising same and/or of a scaffold made therefrom.

According to some of any of the embodiments described herein, the curable groups are attached to 50-100%, or to 50-80%, or to 50-70%, or to 50-60%, or to 60-100%, or to 70-100%, or to 80-100%, or to 90-100%, or to 60-80%, or to 60-90%, or to 70-80%, or to 70-90%, or to 80-90%, of the lysine residues, including any intermediate values and subranges therebetween.

According to some of any of the embodiments described herein, the curable groups are attached to 10-50%, or to 10-40%, or to 10-30%, or to 10-20%, or to 20-50%, or to 20-40%, or to 20-30%, or to 30-50%, or to 30-40%, or to 40-50%, of the lysine residues, including any intermediate values and subranges therebetween.

According to an aspect of some embodiments of the present invention there is provided a process of preparing the conjugate as described herein, the process comprising coupling a compound that features at least one curable group and at least one reactive group to the fibrinogen under conditions that promote formation of a covalent bond between the reactive group and a chemically compatible reactive group of the fibrinogen, as described herein.

According to some of any of the embodiments described herein, the reactive group of the fibrinogen is part of a lysine residue.

Curable Formulation:

According to an aspect of some embodiments of the present invention there is provided a curable formulation which comprises the conjugate as described herein in any of the respective embodiments. According to some embodiments, the formulation further comprises a carrier.

According to some of any of the embodiments described herein, the carrier is an aqueous carrier.

According to an aspect of some embodiments of the present invention there is provided a curable formulation that comprises the conjugate (a curable fibrinogen) as described herein and optionally a carrier as described herein.

According to some of any of the embodiments described herein, the curable formulation further comprises a carrier, and in some of these embodiments, the carrier is an aqueous carrier.

The aqueous carrier can be water, a buffer featuring pH in a range of from about 4 to about 10, or from about 6 to about 8, or from about 7 to about 7.4, a basic aqueous solution or an acidic aqueous solution.

The aqueous carrier can comprise salts and other water-soluble materials at varying concentrations.

According to some of any of the embodiments described herein, the carrier is a pharmaceutically, cosmetically or cosmeceutically acceptable carrier.

In some of any of the embodiments described herein, the aqueous carrier comprises a culturing medium. The culturing medium can be a commercially available culturing medium or a custom-made culturing medium. The culture medium can be any liquid medium which allows at least cell survival. Such a culture medium can include, for example, salts, sugars, amino acids and minerals in the appropriate concentrations and with various additives and those of skills in the art are capable of determining a suitable culture medium to specific cell types. Non-limiting examples of such culture medium include, phosphate buffered saline, DMEM, MEM, RPMI 1640, McCoy's 5A medium, medium 199 and IMDM (available e.g., from Biological Industries, Beth Ha'emek, Israel; Gibco-Invitrogen Corporation products, Grand Island, NY, USA).

The culture medium may be supplemented with various antibiotics (e.g., Penicillin and Streptomycin), growth factors or hormones, specific amino acids (e.g., L-glutamine) cytokines and the like.

In some of any of the embodiments described herein, a concentration of the curable fibrinogen in the curable formulation containing same ranges from 0.1 mg/mL to 100 mg/mL, or from 0.1 mg/mL to 50 mg/mL, or from 0.5 mg/mL to 50 mg/mL, or from 0.5 mg/mL to 20 mg/mL, or from 1 mg/mL to 500 mg/mL, or from 1 mg/mL to 100 mg/mL, or from 1 mg/mL to 50 mg/mL, or from 1 mg/mL to 50 mg/mL, or from 1 mg/mL to 40 mg/mL, or from 1 mg/mL to 30 mg/mL, or from 2 mg/mL to 20 mg/mL, or from 5 mg/mL to 15 mg/mL, including any intermediate values and subranges therebetween. A concentration of the curable fibrinogen in a curable formulation containing same can affect the rheological properties of the formulation and of the hardened formulation (hardened product, e.g., scaffold) obtained upon exposure to a curing condition, and can be manipulated as desired.

According to some embodiments, both the number of curable groups attached to the fibrinogen (also referred to herein as degree of cross-linking or DC) and the concentration of the curable fibrinogen can affect the rheological and mechanical properties of the formulation and of the hardened product obtained upon its exposure to a curing condition, and a combination of these two parameters can be controlled as desired.

According to some of any of the embodiments described herein, the curable formulation further comprises one or more additional materials, including, for example, one or more additional curable materials, one or more non-curable materials and/or one or more biological components or materials.

In some of any of the embodiments described herein, a curable material is or comprises a hydrogel forming material, typically upon cross-linking, entanglement, polymerization and/or co-polymerization, when exposed to a curing condition at which the cross-linking, polymerization and/or co-polymerization, and/or entanglement reaction occurs. Such curable materials are also referred to herein as hydrogel-forming curable materials or as gel-forming materials.

The hydrogel-forming material, according to embodiments of the present invention, can be of biological origin or synthetically prepared.

According to some embodiments of the present invention, the formed hydrogel is biocompatible, and is such that when a biological moiety is impregnated or accumulated therein, an activity of the biological moiety is maintained, that is, a change in an activity of the biological moiety is no more than 30%, or no more than 20%, or no more than 10%, compared to an activity of the biological moiety in a physiological medium.

Exemplary polymers or co-polymers usable for forming a hydrogel according to the present embodiments include polyacrylates, polymethacrylates, polyacrylamides, polymethacrylamides, polyvinylpyrrolidone and copolymers of any of the foregoing. Other examples include polyethers, polyurethanes, and poly(ethylene glycol), functionalized by cross-linking groups or usable in combination with compatible cross linking agents.

Some specific, non-limiting examples, include: poly(2-vinylpiridine), poly(acrylic acid), poly(methacrylic acid), poly(N-isopropylacrylamide), poly(N,N'-methylenbisacrylamide), poly(N—(N-propyl)acrylamide), poly(methacyclic acid), poly(2-hydroxyacrylamide), poly (ethylene glycol) acrylate, poly (ethylene glycol) methacrylate, and polysaccharides such as hyaluronic acid, dextran, alginate, agarose, and the like, and any co-polymer of the foregoing.

In exemplary embodiments, the additional curable material is a mono-functional or multi-functional PEO, as described herein.

Hydrogel precursors (hydrogel-forming materials) forming such polymeric chains are contemplated, including any combination thereof.

Hydrogels are typically formed of, or are formed in the presence of, di- or tri- or multi-functional monomers, oligomer or polymers, which are collectively referred to as hydrogel precursors or hydrogel-forming agents or hydrogen-forming materials, having two, three or more polymerizable groups. The presence of more than one polymerizable group renders such precursors cross-linkable, and allow the formation of the three-dimensional network.

Exemplary cross-linkable monomers include, without limitation, the family of di- and tri-acrylates monomers, which have two or three polymerizable functionalities, one of which can be regarded as a cross-linkable functional group. Exemplary diacrylates monomers include, without limitation, methylene diacrylate, and the family of poly (ethylene glycol)$_n$ dimethacrylate (nEGDMA). Exemplary triacrylates monomers include, without limitation, trimethylolpropane triacrylate, pentaerythritol triacrylate, tris (2-hydroxy ethyl) isocyanurate triacrylate, isocyanuric acid tris(2-acryloyloxyethyl) ester, ethoxylated trimethylolpropane triacrylate, pentaerythrityl triacrylate and glycerol triacrylate, phosphinylidynetris(oxyethylene) triacrylate.

In some of any of the embodiments described herein, a curable material, whether monomeric or oligomeric, can be a mono-functional curable material or a multi-functional curable material, as defined herein.

Curable materials usable in the field of bioprinting are predominantly based on either naturally derived materials, including, for example, Matrigel, Alginate, Pectin, Xanthan gum, Gelatin, Chitosan, Fibrin, Cellulose and Hyaluronic acid, which can be isolated from animal or human tissues, or recombinantly-generated, or synthetically-prepared materials, including, for example, polyethyleneglycol; PEG, gelatin methacrylate; GelMA, poly(propylene oxide); PPO, poly (ethylene oxide); PEO; PEG, polyethyleneglycol-diacrylate, polyglutamic acid, gelatin methacrylate; GelMA, PLGA/PLLA, poly(dimethyl siloxane); Nanocellulose; Pluronic F127, short di-peptides (FF), Fmoc-peptide-based hydrogels such as Fmoc-FF-OH, Fmoc-FRGD-OH, Fmoc-RGDF-OH, Fmoc-2-Nal-OH, Fmoc-FG-OH, and thermoplastic polymers such as Polycaprolactone (PCL), Polylactic acid (PLA) or Poly(D,L-lactide-co-glycolide).

Exemplary curable materials usable in the context of the present embodiments include, but are not limited to, Matrigel, Gelatin methacrylate (GelMA), Nanocellulose (nano-scaled structured materials which are UV-curable, including cellulose nanocrystals (CNC), cellulose nanofibrils (CNF), and bacterial cellulose (BC), also referred to as microbial cellulose), Pluronic® materials, including, for example, Pluronic F127 which is fluid at a low temperature forms a gel at a high temperature, above critical micellar concentration (CMC) and Pluronic F127-diacrylate (DA) which is UV-curable, Hyaluronic acid (HA), Acrylated hyaluronic acid (AHA), methacrylated hyaluronic acid (MAHA), Poly-(ethylene glycol) diacrylate (PEGDA), Alginate, Xanthan gum, Pectin, Chitosan which can be crosslinked with a chemical agent such as Glutaraldehyde, Genipin or Sodium Tripolyphosphate (TPP).

Exemplary curable materials are described in the Examples section that follows.

Biological components or materials that can be included in the curable formulation as described herein include, for example, cellular components, including, for example, culturing cells, and other cellular components such as cytokines, chemokines, growth factors; as well as other biological components such as proteins, agents that act to increase cell attachment, cell spreading, cell proliferation, cell differentiation and/or cell migration; an amino acid, peptides, polypeptides, proteins, DNA, RNA, lipids and/or proteoglycans.

Cells may comprise a heterogeneous population of cells or alternatively the cells may comprise a homogeneous population of cells. Such cells can be for example stem cells (such as embryonic stem cells, bone marrow stem cells, cord blood cells, mesenchymal stem cells, adult tissue stem cells), progenitor cells, or differentiated cells such as chondrocytes, osteoblasts, connective tissue cells (e.g., fibrocytes, fibroblasts and adipose cells), endothelial and epithelial cells. The cells may be naïve or genetically modified.

According to one embodiment of this aspect of the present invention, the cells are mammalian in origin.

Furthermore, the cells may be of autologous origin or non-autologous origin, such as postpartum-derived cells (as described in U.S. application Ser. Nos. 10/887,012 and 10/887,446). Typically the cells are selected according to the desired application.

Suitable proteins which can be used include, but are not limited to, extracellular matrix proteins [e.g., collagen, fibronectin, vimentin, microtubule-associated protein 1D, Neurite outgrowth factor (NOF), bacterial cellulose (BC), laminin and gelatin], cell adhesion proteins [e.g., integrin, proteoglycan, glycosaminoglycan, laminin, intercellular adhesion molecule (ICAM) 1, N-CAM, cadherin, tenascin, gicerin, RGD peptide and nerve injury induced protein 2 (ninjurin2)], growth factors [epidermal growth factor, transforming growth factor-$\alpha$, fibroblast growth factor-acidic, bone morphogenic protein, fibroblast growth factor-basic, erythropoietin, thrombopoietin, hepatocyte growth factor, insulin-like growth factor-I, insulin-like growth factor-II, Interferon-$\beta$, platelet-derived growth factor, Vascular Endothelial Growth Factor and angiopeptin], cytokines [e.g., M-CSF, IL-1beta, IL-8, beta-thromboglobulin, EMAP-II, G-CSF and IL-10], proteases [pepsin, low specificity chymotrypsin, high specificity chymotrypsin, trypsin, carboxypeptidases, aminopeptidases, proline-endopeptidase, *Staphylococcus aureus* V8 protease, Proteinase K (PK), aspartic protease, serine proteases, metalloproteases, ADAMTS17, tryptase-gamma, and matriptase-2] and protease substrates.

In addition, calcium phosphate materials, such as hydroxyapatite, for example, in a form of particles, can be used, including, but not limited to, nanoHA and nanoTCP. The particles size should be compatible with the dispensing heads so as to avoid clogging.

Non-curable materials, other than the biological materials as described herein, that can be included in the curable formulation as described herein can be materials that impart a certain property to the formulation or to the hardened formulation and to the part of the object (e.g., scaffold) formed thereby. Such a property can be a physical property (e.g., an optical property such as transparency or opacity, color, a spectral property, heat resistance, electrical property and the like), or a mechanical or rheological property such as viscosity, elasticity, storage modulus, loss modulus, stiffness, hardness, and the like. Alternatively, or in addition, non-curable materials can be such that provide a biological function, for example, therapeutically active agents.

Exemplary non-curable materials include thixotropic agents, reinforcing agents, toughening agents, fillers, colorants, pigments, etc.

According to some of any of the embodiments described herein, the curable formulation comprises one or more biological components or materials such as, but not limited to, cells, growth factors, peptides, heparan sulfate and fibronectin.

According to some of any of the embodiments described herein, the curable formulation is devoid of a biological material that is other than cells.

According to some of any of the embodiments described herein, the curable formulation is devoid of non-cellular biological material.

According to some of any of the embodiments described herein, the curable formulation is devoid of enzymes.

According to some of any of the embodiments described herein, the curable formulation is devoid of non-cellular proteinaceous material.

According to some of any of the embodiments described herein, the curable formulation is devoid of thrombin.

In some of any of the embodiments described herein, a curable formulation further comprises an agent that promotes curing or hardening of the curable material(s) (the curable fibrinogen of the present embodiments and optionally other curable materials that are included in the formulation) when exposed to a curing condition.

The concentration of the agent can be determined in accordance with the concentration of the curable material(s) and the desired degree of curing (e.g., desired cross-linking degree).

When some or all of the curable materials are photocurable materials, the agent is a photoinitiator. The photoinitiator is selected in accordance with the curing mechanism (e.g., free-radical, cationic, etc.).

A free-radical photoinitiator may be any compound that produces a free radical on exposure to radiation such as ultraviolet or visible radiation and thereby initiates a polymerization reaction. Non-limiting examples of suitable photoinitiators include benzophenones (aromatic ketones) such as benzophenone, methyl benzophenone, Michler's ketone and xanthones; acylphosphine oxide type photo-initiators such as 2,4,6-trimethylbenzolydiphenyl phosphine oxide (TMPO), 2,4,6-trimethylbenzoylethoxyphenyl phosphine oxide (TEPO), and bisacylphosphine oxides (BAPO's); benzoins and bezoin alkyl ethers such as benzoin, benzoin methyl ether and benzoin isopropyl ether and the like. Examples of photoinitiators are alpha-amino ketone, and bisacylphosphine oxide (BAPO's).

Exemplary photoinitiators include, but are not limited to, those of the Irgacure® family, riboflavin, rose Bengal, LAP and more.

A free-radical photo-initiator may be used alone or in combination with a co-initiator. Co-initiators are used with initiators that need a second molecule to produce a radical that is active in the photocurable free-radical systems. Benzophenone is an example of a photoinitiator that requires a second molecule, such as an amine, to produce a free radical. After absorbing radiation, benzophenone reacts with a ternary amine by hydrogen abstraction, to generate an alpha-amino radical which initiates polymerization of acrylates. Non-limiting example of a class of co-initiators are alkanolamines such as triethylamine, methyldiethanolamine and triethanolamine.

Suitable cationic photoinitiators include, for example, compounds which form aprotic acids or Bronsted acids upon exposure to ultraviolet and/or visible light sufficient to initiate polymerization. The photoinitiator used may be a single compound, a mixture of two or more active compounds, or a combination of two or more different compounds, i.e. co-initiators. Non-limiting examples of suitable cationic photoinitiators include aryldiazonium salts, diaryliodonium salts, triarylsulphonium salts, triarylselenonium salts and the like. An exemplary cationic photoinitiator is a mixture of triarylsolfonium hexafluoroantimonate salts.

Non-limiting examples of suitable cationic photoinitiators include P-(octyloxyphenyl) phenyliodonium hexafluoroantimonate UVACURE 1600 from Cytec Company (USA), iodonium (4-methylphenyl)(4-(2-methylpropyl)phenyl)-hexafluorophosphate known as Irgacure 250 or Irgacure 270 available from Ciba Speciality Chemicals (Switzerland), mixed arylsulfonium hexafluoroantimonate salts known as UVI 6976 and 6992 available from Lambson Fine Chemicals (England), diaryliodonium hexafluoroantimonate known as PC 2506 available from Polyset Company (USA), (tolylcumyl) iodonium tetrakis (pentafluorophenyl) borate known as Rhodorsil® Photoinitiator 2074 available from Bluestar Silicones (USA), iodonium bis(4-dodecylphenyl)-(OC-6-11)-hexafluoro antimonate known as Tego PC 1466 from Evonik Industries AG (Germany).

According to some of any of the embodiments described herein, the curable formulation further comprises an agent for promoting polymerization and/or cross-linking of the conjugate.

According to some of any of the embodiments described herein, the curable groups are photopolymerizable groups and the agent is a photoinitiator.

According to some of any of the embodiments described herein, an amount of the agent for promoting polymerization and/or cross-linking of the curable material(s) (e.g., a photoinitiator as described herein) ranges from 0.1 to 10% by weight of the total weight of the formulation, including any intermediate values and subranges therebetween.

According to some of any of the embodiments described herein, the curable formulation further comprises a polymeric material that features at least one curable group.

According to some of any of the embodiments described herein, the polymeric material is a mono-functional and/or multi-functional curable synthetic polymer (e.g., a mono-functional and/or multi-functional polyethylene oxide).

According to some of any of the embodiments described herein, the curable group is a photopolymerizable group.

According to some of any of the embodiments described herein, the cross-linking agent is a polymeric material that comprises two or more curable groups as described herein.

According to some of any of the embodiments described herein, the polymeric material is a non-biological polymeric material (a polymeric material that is not derived from a biological source or is not present in a biological substance).

According to some of any of the embodiments described herein, the polymeric material is a synthetic polymeric material.

According to some of any of the embodiments described herein, the polymeric material is a synthetic polymer.

According to some of any of the embodiments described herein, the polymeric material is a biocompatible material.

Exemplary synthetic polymeric material that are usable in the context of these embodiments of the present invention include, but are not limited to, poly(alkylene glycol)s such as polyethylene glycol (PEG or PEO), Hydroxyapatite/polycaprolactone (HA/PLC), polyglycolic acid (PGA), Poly-L-lactic acid (PLLA), Polymethyl methacrylate (PMMA), polyhydroxyalkanoate (PHA), poly-4-hydroxybutyrate (P4HB), polypropylene fumarate (PPF), beta-tricalcium phosphate (beta-TCP) and polytetrafluoroethylene (PTFE). These materials can be modified so to feature two or more curable groups, using methods known in the art.

The (e.g., synthetic) polymeric material can be a linear or branched polymeric material.

According to some of any of the embodiments described herein, the cross-linking agent is a poly(alkylene glycol) that features 2, 3, 4 or more curable groups (e.g., acrylic groups, for example, methacrylate groups). Exemplary such polymeric materials are described in the Examples section that follows.

According to some of any of the embodiments described herein, an average molecular weight of the polymeric material ranges from 1 to 100 kDa, or from 1 to 50 kDa, or from 2 to 50 kDa, or from 5 to 50 kDa, or from 5 to 30 kDa, including any intermediate values and subranges therebetween.

According to some of any of the embodiments described herein, an amount of the polymeric material ranges from 0.5 to 10%, or from 1 to 10%, or from 1 to 5%, or from 2 to 10%, by weight of the total weight of the formulation, including any intermediate values and subranges therebetween.

The number of curable groups in the cross-linking agent, its structure (linear or branched), its molecular weight, and its amount, each independently and altogether may affect the properties of the curable formulation or the hardened product obtained upon exposure to a curing condition.

According to some embodiments, a hydrogel-forming agent or material as described herein is included in the formulation as a cross-linking agent.

According to some of any of the embodiments described herein, the curable formulation is devoid of a cross-linking agent. According to some of these embodiments, the curable fibrinogen is included in the curable formulation in an amount of at least 2% by weight, or at least 3%, preferably at least 4%, by weight, of the total weight of the formulation. According to some of these embodiments, a concentration of the curable fibrinogen is at least 10 mg/mL, or at least 20, preferably at least 30, or at least 40, mg/mL, or is higher.

According to some of any of the embodiments described herein, when a concentration of the curable fibrinogen is lower than 40 mg/mL or lower than 30 mg/mL, or lower than 20 mg/mL, the formulation further comprises a cross-linking agent as described herein in any of the respective embodiments.

According to some of any of the embodiments described herein, when a concentration of the curable fibrinogen is lower than 4% or lower than 3%, or lower than 2%, by weight, of the total weight of the formulation, the formulation further comprises a cross-linking agent as described herein in any of the respective embodiments.

According to some of any of the embodiments described herein, the curable formulation further comprises a porogen. An exemplary porogen is poly(alkylene oxide) (poly(alkylene glycol)).

According to some of any of the embodiments described herein, the curable formulation further comprises a biological material other than the fibrinogen.

According to some of any of the embodiments described herein, the biological material comprises cells.

According to some of any of the embodiments described herein, the curable formulation is for use as a modeling material formulation for additive manufacturing of a three-dimensional object having in at least a portion thereof a fibrinogen-based material, as described in further detail hereinafter.

Scaffold:

According to an aspect of some embodiments of the present invention there is provided a scaffold obtained by subjecting the curable formulation as described herein in any of the respective embodiments to a suitable curing condition.

According to an aspect of some embodiments of the present invention there is provided a scaffold comprising a three-dimensional network formed upon subjecting the conjugate as described herein in any of the respective embodiments or the curable formulation as described herein in any of the respective embodiments to a suitable curing condition (a condition that affects polymerization and/or cross-linking of the curable groups).

According to some of any of the embodiments described herein, the scaffold is formed by an additive manufacturing process (e.g., bioprinting) as described herein.

According to some of any of the embodiments described herein, the scaffold is in a form of a hydrogel.

According to some of any of the embodiments described herein, there is provided a scaffold formed upon exposing the curable formulation as described herein to a curing condition as described herein (e.g., for effecting cross-linking).

According to some embodiments, the scaffold is formed upon cross-linking the curable fibrinogen, alone or with a cross-linking agent, within the carrier (e.g., aqueous carrier) of the curable formulation.

The conjugate described herein can therefore be referred to also as a precursor molecule for generating a scaffold. Thus, the scaffold is formed by cross-linking a plurality of precursor molecules (a plurality of molecules of a curable fibrinogen as described herein) to one another, optionally via a cross-linking agent as described herein.

As used herein, the term "scaffold" describes a two-dimensional or a three-dimensional supporting framework. The scaffold according to embodiments of the present invention is composed of precursor units (comprising the conjugates as described herein) which are cross-linked therebetween, optionally via a cross-linking agent as described herein. The scaffold of the present embodiments can be regarded as a network of fibrinogen molecules that are covalently attached to one another, directly, via a cross-linking between the curable groups and/or by means of a cross-linking agent that connects two or more curable groups (depending on its functionality) within a fibrinogen molecule and/or between two or more fibrinogen molecules.

In some embodiments, a scaffold can be used as a support for cell growth, attachment and/or spreading and thus facilitates tissue generation and/or tissue repair. In some embodiments, a scaffold maintains a desired shape of a tissue and/or cell colony supported thereby.

In some embodiments, the scaffold is in a form of a hydrogel.

Herein and in the art, the term "hydrogel" describes a three-dimensional fibrous network containing at least 20%, typically at least 50%, or at least 80%, and up to about 99.99% (by mass) water. A hydrogel can be regarded as a material which is mostly water, yet behaves like a solid or semi-solid due to a three-dimensional crosslinked solid-like network, made of polymeric chains (e.g., fibrinogen chains), within the liquid dispersing medium. The polymeric chains are inter-connected (crosslinked) by chemical bonds (covalent, hydrogen and ionic/complex/metallic bonds, typically covalent bonds).

Hydrogels may take a physical form that ranges from soft, brittle and weak to hard, elastic and tough material. Soft hydrogels may be characterized by rheological parameters including elastic and viscoelastic parameters, while hard hydrogels are suitably characterized by tensile strength parameters, elastic, storage and loss moduli, as these terms are known in the art.

The softness/hardness of a hydrogel is governed inter alia by the chemical composition of the polymer chains, the "degree of cross-linking" (number of interconnected links between the chains), the aqueous media content and composition, and temperature.

A hydrogel, according to some embodiments of the present invention, may contain macromolecular polymeric and/or fibrous elements which are not chemically connected to the main cross-linked network but are rather mechanically intertwined therewith and/or immersed therein. Such macromolecular fibrous elements can be woven (as in, for example, a mesh structure), or non-woven, and can, in some embodiments, serve as reinforcing materials of the hydrogel's fibrous network. Non-limiting examples of such macromolecules include polycaprolactone, gelatin, gelatin methacrylate, alginate, alginate methacrylate, chitosan, chitosan methacrylate, glycol chitosan, glycol chitosan methacrylate, hyaluronic acid (HA), HA methacrylate, and other non-crosslinked natural or synthetic polymeric chains and the likes. Alternatively, or in addition, such macromolecules are chemically connected to the main crosslinked network of the hydrogel, for example, by acting as a cross-linking agent, or by otherwise forming a part of the three-dimensional network of the hydrogel.

In some of any of the embodiments described herein, the scaffold comprises cross-linked fibrinogen, in which a plurality of fibrinogen units are linked to one another to thereby form a three-dimensional network.

The three-dimensional network or scaffold can be in a form of, for example, a film, a sponge, a porous structure, a hydrogel, and any other form, according to a desired need.

In some embodiments, the scaffold is generated by subjecting a plurality of conjugate molecules, or a curable formulation comprising same, as described herein, to conditions for effecting covalent cross-linking of the curable groups of the conjugate molecules, and optionally of the cross-linking agent, if present in the formulation.

The scaffolds may be administered to subjects in need thereof for the regeneration of tissue such as connective tissue, muscle tissue such as cardiac tissue and pancreatic tissue. Any other tissue as described herein is also contemplated.

According to some embodiments, the scaffold can be used in cell cultures.

The phrase "cell culture" or "culture" as used herein refers to the maintenance of cells in an artificial, e.g., an in vitro environment. The term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms.

According to some of any of the embodiments described herein, the scaffold is characterized by shear storage modulus (G') of at least 50 Pa, at least 100 Pa, or at least 200 Pa or at least 300 Pa or at least 400 Pa, for example, of from 50 to 1,500 Pa, or from 50 to 1,000 Pa, or from 100 to 1,500 Pa, or from 100 to 1,000 Pa, or from 200 to 1,500 Pa, or from 200 to 1,000 Pa, or from 300 to 1,500 Pa, or from 300 to 1,000 Pa, or from 400 to 1,500 Pa, or from 400 to 1,000 Pa, or from 500 to 1,500 Pa, or from 500 to 1,000 Pa, including any intermediate values and subranges therebetween. The shear storage modulus can be determined by methods well known in the art, for example, as described herein in the Examples section that follows.

As used herein and in the art, a "shear modulus" is defined as the ratio of shear stress to the shear strain. The shear modulus may be a complex variable, in which case the "storage modulus" is the real component and the "loss modulus" is the imaginary component. The storage modulus and loss modulus in viscoelastic solids measure the stored energy, representing the elastic portion, and the energy dissipated as heat, representing the viscous portion.

According to some of any of the embodiments described herein, the scaffold is characterized by a swelling capacity (a degree of swelling, as defined herein for Qt) higher than 90% or higher than 95%, or from 80 to about 100%, or from 80 to about 95%, or from 90 to about 100%, or from 90 to about 95%, or from 95 to about 100%, including any intermediate value and subrange therebetween. The swelling capacity can be determined as described herein in the Examples section that follows.

According to some of any of the embodiments described herein, the scaffold is biodegradable.

According to some of any of the embodiments described herein, the scaffold is characterized by a proteolytic degradation that is lower from a proteolytic degradation of fibrinogen (e.g., lower by at least 50%, for example, lower by any value of from 50% to 98%).

According to some of any of the embodiments described herein, the scaffold further comprises cells (e.g., as described herein) embedded therewithin and/or on at least a portion of the surface thereof. The cells may comprise one cell type or a two or more cell types.

Such a scaffold can be formed from a curable formulation that further comprises cells. Alternatively, cells can be seeded in the scaffold once it is formed, as described herein.

According to some of any of the embodiments described herein, a viability of the cells is maintained upon incubating the scaffold for at least 5 days (e.g., at 37° C.).

According to an aspect of some embodiments of the invention, there is provided a process of producing a scaffold as described herein. The process comprises exposing a curable fibrinogen as described herein, or a curable formulation comprising same, as described herein, to a condition that effects curing, as described herein, for example, to a condition that effects cross-linking of the curable groups, thereby producing the scaffold.

Optionally, the exposure to a curing conditions is effected in vivo.

Alternatively, the exposure to a curing condition is effected ex vivo.

The curing condition depends on the chemical properties of the curable groups.

Preferably, the curing condition is biocompatible, namely, uses agents or conditions which are not considered as hazardous in in vivo applications.

According to some embodiments, the curable groups are photocurable groups (e.g., UV-curable groups) and the curing condition comprises irradiation (e.g., at a wavelength of about 365 nm).

When curing is effected in vivo, it is preferable to avoid irradiation doses that are harmful. The maximal dose which is non-harmful will depend, for example, on the type (e.g., wavelength) of irradiation, and on the part of the body exposed to the irradiation. One skilled in the art will readily be capable of determining whether a dose is harmful or non-harmful.

Uses:

According to some of any of the embodiments described herein, the scaffold is for use in tissue healing and/or regeneration.

According to some of any of the embodiments described herein, the scaffold is for use in repairing a damaged tissue.

According to some of any of the embodiments described herein, the scaffold is for use as an artificial tissue or organ.

According to some of any of the embodiments described herein, the scaffold is for use in diagnosis, for example, for sorting cells according to their type, as described herein.

According to some of any of the embodiments described herein, the scaffold is injectable.

According to some of any of the embodiments described herein, the scaffold is formed ex vivo or in vivo.

The scaffold described herein may be useful for inducing formation of a tissue, for example, by serving as a matrix for supporting cellular growth and/or invasion, and/or by providing cells (e.g., embedded in the scaffold) which induce tissue formation. Such properties may be useful for repairing tissue damage.

According to an aspect of some embodiments of the present invention there is provided a method of inducing formation of a tissue in a subject in need thereof, which comprises implanting a scaffold as described herein in the subject. According to these embodiments, the scaffold is formed ex-vivo. According to some of these embodiments, the scaffold is injectable and the implanting is by injecting the scaffold to a location within the subject where formation of a tissue is desired or needed (e.g. via syringe, catheter, and the like). Alternatively, the scaffold is implanted using methods known in the art, for example, using surgical procedures, devices and/or tools (e.g., as a scalpel, spoon, spatula, or other surgical devices).

As used herein throughout, the term "subject" refers to a vertebrate, preferably a mammal, more preferably a human being (male or female) at any age.

Herein, the terms "implant" and "implantation" encompass placing a substance (e.g., a scaffold as described herein) in a body (e.g., in or in the vicinity of an organ) or on a body surface (e.g., on a skin surface).

The method is for inducing in vivo formation of a tissue.

The phrase "in vivo" refers to within a living organism such as a plant or an animal, preferably in mammals, preferably, in human subjects.

A method of inducing in vivo formation of a tissue can be also achieved by administering the scaffold precursor molecules—the curable fibrinogen—to the subject and exposing the curable fibrinogen to a curing condition in vivo.

Thus, according to another aspect of some embodiments of the present invention there is provided a method of inducing in vivo formation of a tissue, which comprises administering to the subject the curable fibrinogen or the curable formulation comprising same, as described herein in any of the respective embodiments and any combination thereof, and exposing the curable fibrinogen or the formulation to a curing condition (that effects polymerization and/or cross-linking of the conjugate).

Herein throughout, the phrase "tissue" refers to part of an organism consisting of an aggregate of cells having a similar structure and function. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue and fat tissue. Preferably, the phrase "tissue" as used herein also encompasses the phrase "organ" which refers to a fully differentiated structural and functional unit in an animal that is specialized for some particular function. Non-limiting examples of organs include head, brain, eye, leg, hand, heart, liver kidney, lung, pancreas, ovary, testis, and stomach.

The scaffold of the present embodiments can be also used for ex vivo formation of a tissue.

Thus according to another aspect of some embodiments of the present invention there is provided a method of inducing ex-vivo formation of a tissue.

As used herein, the phrase "ex vivo" refers to living cells which are derived from an organism and are growing (or cultured) outside of the living organism, preferably, outside the body of a vertebrate, a mammal, or human being. For example, cells which are derived from a human being such as human muscle cells or human aortic endothelial cells and are cultured outside of the body are referred to as cells which are cultured ex vivo.

The method is effected by seeding the scaffold of the present embodiments with cells to thereby induce tissue formation.

The cells are preferably capable of forming a tissue. Such cells can be for example, stem cells such as embryonic stem cells, bone marrow stem cells, cord blood cells, mesenchymal stem cells, adult tissue stem cells, or differentiated cells such as neural cells, retina cells, epidermal cells, hepatocytes, pancreatic cells, osseous cells, cartilaginous cells, elastic cells, fibrous cells, myocytes, myocardial cells, endothelial cells, smooth muscle cells, and hematopoietic cells.

The term "seeding" refers to encapsulating, entrapping, plating, placing and/or dropping cells into the scaffold. It will be appreciated that the concentration of cells which are seeded on or within the scaffold depends on the type of cells used and the composition of scaffold used.

The seeding of the cells can be performed following the formation of the scaffold or by including the cells in the curable formulation.

In some embodiments, following seeding the cells, the cells are cultured in the presence of tissue culture medium and growth factors.

The scaffold of the present invention which is formed in vitro, ex vivo or in vivo can be used to induce tissue formation and/or regeneration and thus treat subjects suffering from tissue damage or loss. The scaffold can also be used as a filler of a tissue.

According to an aspect of some embodiments of the present invention there is provided a method of treating a subject having a disorder characterized by tissue damage or loss.

In some embodiments, the method is effected by implanting the scaffold alone or following seeding such a scaffold with cells, or by administering the curable fibrinogen or curable formulation as described herein into the subject and exposing it to a curing condition, to thereby induce formation of the tissue and treat the disorder characterized by tissue damage or loss.

As used herein the phrase "disorder characterized by tissue damage or loss" refers to any disorder, disease or condition exhibiting a tissue damage (e.g., non-functioning tissue, cancerous or pre-cancerous tissue, broken tissue, fractured tissue, fibrotic tissue, or ischemic tissue) or a tissue loss (e.g., following a trauma, an infectious disease, a genetic disease, and the like) which require tissue regeneration. Examples for disorders or conditions requiring tissue regeneration include, but are not limited to, liver cirrhosis such as in hepatitis C patients (liver tissue), type-1 diabetes (pancreatic tissue), cystic fibrosis (lung, liver, pancreatic tissue), bone cancer (bone tissue), burn and wound repair (skin tissue), age related macular degeneration (retinal tissue), myocardial infarction, myocardial repair, CNS lesions (myelin), articular cartilage defects (chondrocytes), bladder degeneration, intestinal degeneration, and the like. In addition, cosmetic tissue damage or loss is encompassed by the term "disorder".

As used herein, the term "cosmetic" refers to apparent (e.g., visible) tissue, including, but not limited to, skin tissue. Cosmetic tissue damage or loss is typically detrimental aesthetically, and may be detrimental for additional reasons (e.g. psychological factors).

Herein, the phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

It will be appreciated that the cells to be implanted in a subject (e.g., for inducing in vivo tissue formation and/or following ex vivo formation of a tissue), as described herein, may optionally be derived from the treated subject (autologous source), and optionally from allogeneic sources such as embryonic stem cells which are not expected to induce an immunogenic reaction.

According to another aspect of embodiments of the invention, there is provided a method of treating a subject having a disorder characterized by tissue damage or loss (e.g., as described herein), the method comprising administering to the subject (e.g., implanting or injecting, as described herein) a scaffold as described herein, as described herein.

According to another aspect of embodiments of the invention, there is provided a method of treating a subject having a disorder characterized by tissue damage or loss (e.g., as described herein), the method comprising administering to the subject a conjugate as described herein or a curable formulation, as described herein.

A conjugate described herein may be provided as a composition, for example a composition for effecting a method or use described herein. The composition may be for effecting a pharmaceutical (e.g., medicinal) treatment and/or a cosmetic treatment (e.g., as described herein).

A scaffold described herein may be provided as a composition, for example a composition for effecting a method or use described herein. The composition may be for effecting a pharmaceutical (e.g., medicinal) treatment and/or a cosmetic treatment (e.g., as described herein).

Hence, according to an aspect of embodiments of the invention, there is provided a pharmaceutical, cosmetic or cosmeceutical composition comprising a plurality of molecules of a conjugate described herein, the composition being identified for use in inducing formation of a tissue upon being contacted with a tissue and further upon subjecting the composition to a curing condition.

Optionally, the composition is identified for use in inducing formation of a tissue upon further subjecting the plurality of molecules of the conjugate to conditions (e.g., as described herein) that effect curing, as described herein According to a further aspect of embodiments of the invention, there is provided a pharmaceutical, cosmetic or cosmeceutical composition comprising a scaffold as described herein in any of the respective embodiments, the composition being identified for use in inducing formation of a tissue upon being contacted with a tissue and further upon subjecting the composition to a curing condition.

Herein, the phrase "cosmeceutical composition" refers to a composition characterized by both pharmaceutical and cosmetic uses.

Optionally, the composition described herein is packaged in a packaging material and identified in print, in or on the packaging material, for use in inducing formation of tissue and/or for treating a disorder, as described herein.

The composition may further comprise a pharmaceutically acceptable carrier, and be formulated for facilitating its administration (e.g., implantation or injection).

Herein, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Optionally, the carrier is an aqueous carrier, for example, an aqueous solution (e.g., saline).

Kits:

According to an aspect of some embodiments of the present invention there is provided a kit comprising the conjugate as described herein in any of the respective embodiments, or the curable formulation as described herein in any of the respective embodiments, packaged therein, the kit being identified for use in forming a scaffold or a three-dimensional object that comprises, in at least a portion thereof, a fibrinogen-based material, as described herein in any of the respective embodiments or any combination thereof.

According to some of any of the embodiments described herein, the curable formulation further comprises a carrier, and the kit further comprises the carrier or instructions to prepare the formulation with the carrier.

According to some embodiments, the kit comprises the conjugate and the carrier, and optionally a cross-linking agent as described herein, each being individually packaged in the kit. In some embodiments, the kit comprises instructions to prepare the curable formulation.

Optionally, the kit further comprises cells for embedding in the scaffold (e.g., as described herein).

The cells may form a part of the carrier or may be packaged separately.

In some embodiments, the conjugate and the carrier, and optionally the cross-linking agent, if present, are packaged within the kit at a ratio suitable for obtaining a scaffold with the desired properties. Such a ratio can be pre-determined as detailed hereinabove.

Optionally, the instructions further include guidance for selecting a suitable ratio for obtaining a suitable property of the scaffold, in accordance with the description provided herein.

The instructions may further include guidance with regard to selecting the curing condition for obtaining a scaffold with desired properties.

According to an aspect of some embodiments of the present invention there is provided a kit comprising the scaffold as described herein in any of the respective embodiments, or a composition comprising the scaffold, as described herein, packaged therein, the kit being identified for use in any of the methods as described herein.

In some embodiments, the kit may further comprises means for administering (e.g., injecting) or implanting the scaffold to the subject, for example, as described herein.

Additive Manufacturing:

According to an aspect of some embodiments of the present invention there is provided a process of additive manufacturing a three-dimensional object featuring, in at least a portion thereof, a fibrinogen-based material, the process comprising dispensing at least one modeling material formulation to sequentially form a plurality of layers in a configured pattern corresponding to a shape of the object, wherein for at least a portion of the layers, the dispensing is of a modeling material formulation that comprises the conjugate as described herein in any of the respective embodiments or the curable formulation as described herein in any of the respective embodiments, thereby manufacturing the three-dimensional object.

According to some of any of the embodiments described herein, the process further comprises exposing the portion of the layers to a curing condition suitable for hardening the conjugate or the formulation.

According to some of any of the embodiments described herein, at least a portion of the curable groups are photo-curable groups, and the curing condition comprises irradiation.

According to an aspect of some embodiments of the present invention, there is provided three-dimensional biological object featuring, in at least a portion thereof, a fibrinogen-based material, obtainable by the process as described herein.

According to an aspect of some embodiments of the present invention, there is provided a process (a method) of additive manufacturing (AM) of a three-dimensional object. According to embodiments of this aspect, the method is effected by sequentially forming a plurality of layers in a configured pattern corresponding to the shape of the object, thereby forming the object. According to embodiments of this aspect, formation of each layer is effected by dispensing at least one uncured building material, and exposing the dispensed building material to a curing condition to thereby form a hardened (cured) material. According to these embodiments, the at least one uncured building material comprises the curable formulation as described herein.

Herein throughout, the phrase "building material" encompasses the phrases "uncured building material" or "uncured building material formulation" and collectively describes the materials that are dispensed by sequentially forming the layers, as described herein. This phrase encompasses uncured materials which form the final object, namely, one or more uncured modeling material formulation(s), and optionally also uncured materials used to form a support, namely uncured support material formulations. The building material can also include non-curable materials that preferably do not undergo (or are not intended to undergo) any change during the process, for example, biological materials or components (other than a curable fibrinogen conjugate as described herein) and/or other agents or additives as described herein.

The building material that is dispensed to sequentially form the layers as described herein is also referred to herein interchangeably as "printing medium" or "bioprinting medium".

An uncured building material can comprise one or more modeling material formulations, and can be dispensed such that different parts of the object are made upon hardening (e.g., curing) of different modeling formulations, and hence are made of different hardened (e.g., cured) modeling materials or different mixtures of hardened (e.g., cured) modeling materials.

The method of the present embodiments manufactures three-dimensional objects in a layerwise manner by forming a plurality of layers in a configured pattern corresponding to the shape of the object.

Each layer is formed by an additive manufacturing apparatus which scans a two-dimensional surface and patterns it. While scanning, the apparatus visits a plurality of target locations on the two-dimensional layer or surface, and decides, according to a pre-set algorithm, for each target location or a group of target locations, whether or not the target location or group of target locations is to be occupied by a building material, and which type of a building material is to be delivered thereto. The decision is made according to a computer image of the surface.

When the AM is by three-dimensional inkjet printing, an uncured building material, as defined herein, is dispensed from a dispensing head having a set of nozzles to deposit building material in layers on a supporting structure. The AM apparatus thus dispenses building material in target locations which are to be occupied and leaves other target locations void. The apparatus typically includes a plurality of dispensing heads, each of which can be configured to dispense a different building material (for example, different modeling material formulations, each containing a different biological component; or each containing a different curable material; or each containing a different concentration of a curable material, and/or different support material formulations). Thus, different target locations can be occupied by different building materials (e.g., a modeling formulation and/or a support formulation, as defined herein).

The final three-dimensional object is made of the hardened modeling material or a combination of hardened modeling materials or a combination of hardened modeling material/s and support material/s or modification thereof (e.g., following curing). All these operations are well-known to those skilled in the art of additive manufacturing (also known as solid freeform fabrication).

In some exemplary embodiments of the invention an object is manufactured by dispensing a building material that comprises two or more different modeling material formulations, each modeling material formulation from a different dispensing head of the AM apparatus. The modeling material formulations are optionally and preferably deposited in layers during the same pass of the dispensing heads. The modeling material formulations and/or combination of formulations within the layer are selected according to the desired properties of the object.

An exemplary process according to some embodiments of the present invention starts by receiving 3D printing data corresponding to the shape of the object. The data can be received, for example, from a host computer which transmits digital data pertaining to fabrication instructions based on computer object data, e.g., in a form of a Standard Tessellation Language (STL) or a StereoLithography Contour (SLC) format, Virtual Reality Modeling Language (VRML), Additive Manufacturing File (AMF) format, Drawing Exchange Format (DXF), Polygon File Format (PLY), Digital Imaging and Communications in Medicine (DICOM) or any other format suitable for Computer-Aided Design (CAD).

The process continues by dispensing the building material as described herein in layers, on a receiving medium, using one or more dispensing (e.g., printing) heads, according to the printing data.

The dispensing can be in a form of droplets, or a continuous stream, depending on the additive manufacturing methodology employed and the configuration of choice.

The receiving medium can be a tray of a printing system, or a supporting article or medium made of, or coated by, a biocompatible material, such as support media or articles commonly used in bioprinting, or a previously deposited layer.

In some embodiments, the receiving medium comprises a sacrificial hydrogel or other biocompatible material as a mold to embed the printed object, and is thereafter removed by chemical, mechanical or physical (e.g., heating or cooling) means. Such sacrificial hydrogels can be made of, for example, a Pluronic material or of Gelatin.

Once the uncured building material is dispensed on the receiving medium according to the 3D data, the method optionally and preferably continues by hardening the dispensed formulation(s). In some embodiments, the process continues by exposing the deposited layers to a curing condition. Preferably, the curing condition is applied to each individual layer following the deposition of the layer and prior to the deposition of the previous layer.

As used herein throughout, the term "curing" describes a process in which a formulation is hardened. The hardening of a formulation typically involves an increase in a viscosity of the formulation and/or an increase in a storage modulus of the formulation (G'). In some embodiments, a formulation which is dispensed as a liquid becomes solid or semi-solid (e.g., gel) when hardened. A formulation which is dispensed as a semi-solid (e.g., soft gel) becomes solid or a harder or stronger semi-solid (e.g., strong gel) when hardened.

The term "curing" as used herein throughout encompasses, for example, polymerization of monomeric and/or oligomeric materials and/or cross-linking of polymeric chains (either of a polymer present before curing or of a polymeric material formed in a polymerization of the monomers or oligomers). The product of a curing reaction is therefore typically a polymeric material and/or a cross-linked material. This term, as used herein, encompasses also partial curing, for example, curing of at least 20% or at least 30% or at least 40% or at least 50% or at least 60% or at least 70% of the formulation, as well as 100% of the formulation.

Herein, the phrase "a condition that affects curing" or "a condition for inducing curing", which is also referred to herein interchangeably as "curing condition" or "curing inducing condition" describes a condition which, when applied to a formulation that contains a curable material, induces a curing as defined herein. Such a condition can include, for example, application of a curing energy, as described hereinafter to the curable material(s), and/or contacting the curable material(s) with chemically reactive components such as catalysts, co-catalysts, and activators.

When a condition that induces curing comprises application of a curing energy, the phrase "exposing to a curing condition" and grammatical diversions thereof means that the dispensed layers are exposed to the curing energy and the exposure is typically performed by applying a curing energy to the dispensed layers.

A "curing energy" typically includes application of radiation or application of heat.

The radiation can be electromagnetic radiation (e.g., ultraviolet or visible light), or electron beam radiation, or ultrasound radiation or microwave radiation, depending on the materials to be cured. The application of radiation (or irradiation) is effected by a suitable radiation source. For example, an ultraviolet or visible or infrared or Xenon or mercury or lamp, or LED source, can be employed, as described herein.

A curable material or system that undergoes curing upon exposure to radiation is referred to herein interchangeably as "photopolymerizable" or "photoactivatable" or "photocurable".

When the curing energy comprises heat, the curing is also referred to herein and in the art as "thermal curing" and comprises application of thermal energy. Applying thermal energy can be effected, for example, by heating a receiving medium onto which the layers are dispensed or a chamber hosting the receiving medium, as described herein. In some embodiments, the heating is effected using a resistive heater.

In some embodiments, the heating is effected by irradiating the dispensed layers by heat-inducing radiation. Such irradiation can be effected, for example, by means of an IR lamp or Xenon lamp, operated to emit radiation onto the deposited layer.

In some embodiments, heating is effected by infrared radiation applied by a ceramic lamp, for example, a ceramic lamp that produces infrared radiation of from about 3 μm to about 4 μm, e.g., about 3.5 μm.

A curable material or system that undergoes curing upon exposure to heat is referred to herein as "thermally-curable" or "thermally-activatable" or "thermally-polymerizable".

In some of any of the embodiments described herein, hardening the dispensed formulation(s) comprises exposing the dispensed formulation to a curing condition as described herein in any of the respective embodiments, for example, to irradiation (illumination).

In some embodiments, the exposure to a curing condition is for a short time period, for example, a time period of less than 3 minutes, less than 300 seconds, for example, of from 10 seconds to 240 seconds, or from 10 seconds to 120 seconds, to from 10 seconds to 60 seconds, including an intermediate values and subranges therebetween.

In some of any of the embodiments described herein, all the curable materials in the building material are cured under the same curing condition. In some embodiments, all curable materials are photocurable.

In some of any of the embodiments described herein, the method further comprises exposing the cured modeling material formulation(s) either before or after removal of a support material formulation, if such has been included in the building material, to a post-treatment condition. The post-treatment condition is typically aimed at further hardening the cured modeling material(s). In some embodiments, the post-treatment hardens a partially-cured formulation to thereby obtain a completely cured formulation.

In some embodiments, the post-treatment is effected by exposure to heat or radiation, as described in any of the respective embodiments herein.

Some embodiments contemplate the fabrication of an object by dispensing different formulations from different dispensing heads. These embodiments provide, inter alia, the ability to select formulations from a given number of formulations and define desired combinations of the selected formulations and their properties.

According to the present embodiments, the spatial locations of the deposition of each formulation with the layer are defined, either to effect occupation of different three-dimensional spatial locations by different formulations, or to effect occupation of substantially the same three-dimensional location or adjacent three-dimensional locations by two or more different formulations so as to allow post deposition spatial combination of the formulations within the layer.

A system utilized in additive manufacturing may include a receiving medium and one or more dispensing heads. The receiving medium can be, for example, a fabrication tray that may include a horizontal surface to carry the material dispensed from the printing head. In some embodiments, the receiving medium is made of, or coated by, a biocompatible material, as described herein.

The dispensing head may be, for example, a printing head having a plurality of dispensing nozzles arranged in an array of one or more rows along the longitudinal axis of the dispensing head. The dispensing head may be located such that its longitudinal axis is substantially parallel to the indexing direction.

The additive manufacturing system may further include a controller, such as a microprocessor to control the AM process, for example, the movement of the dispensing head according to a pre-defined scanning plan (e.g., a CAD configuration converted to a Standard Tessellation Language (STL) format and programmed into the controller). The dispensing head may include a plurality of jetting nozzles. The jetting nozzles dispense material onto the receiving medium to create the layers representing cross sections of a 3D object.

In addition to the dispensing head, there may be a source of curing energy, for curing the dispensed building material. The curing energy is typically radiation, for example, UV radiation or heat radiation. Alternatively, there may be means for providing a curing condition other than electromagnetic or heat radiation, for example, means for cooling the dispensed building material of for contacting it with a reagent that promotes curing.

Additionally, the AM system may include a leveling device for leveling and/or establishing the height of each layer after deposition and at least partial solidification, prior to the deposition of a subsequent layer.

According to the present embodiments, the additive manufacturing method described herein is for bioprinting a biological object.

As used herein, "bioprinting" means practicing an additive manufacturing process while utilizing one or more bio-ink formulation(s) that comprise(s) biological components, as described herein, via methodology that is compatible with an automated or semi-automated, computer-aided, additive manufacturing system as described herein (e.g., a bioprinter or a bioprinting system).

Herein throughout, the phrase "modeling material formulation", which is also referred to herein interchangeably as "modeling formulation" or "modeling material composition" or "modeling composition", or simply as a "formulation", or a "curable formulation", describes a part or all of the uncured building material (printing medium) which is dispensed so as to form the final object, as described herein. The modeling formulation is an uncured modeling formulation, which, upon exposure to a curing condition, forms the object or a part thereof.

In the context of bioprinting, an uncured building material comprises at least one modeling formulation that comprises one or more biological components or materials (e.g., a curable fibrinogen conjugate as described herein), and is also referred to herein and in the art as "bio-ink" or "bio-ink formulation".

In some embodiments, the bioprinting comprises sequential formation of a plurality of layers of the uncured building material in a configured pattern, preferably according to a three-dimensional printing data, as described herein. At least one, and preferably most or all, of the formed layers (before hardening or curing) comprise(s) one or more biological component(s) as described herein (e.g., a curable fibrinogen conjugate as described herein). Optionally, at least one of the formed layers (before hardening or curing) comprises one or more non-biological curable materials, and/or non-curable biological or non-biological components, preferably biocompatible materials which do not interfere (e.g., adversely affect) with the biological and/or structural features of the biological components (e.g., fibrinogen) in the printing medium and/or bio-ink.

In some embodiments, the components in the bio-ink or the printing medium, e.g., non-curable and curable materials, and/or the curing condition applied to effect curing, are selected such that they do not significantly affect structural and/or functional properties of the biological components in the bio-ink or printing medium.

In some of any of the embodiments described herein, the building material (e.g., the printing medium) comprises modeling material formulation(s) (bio-ink) and optionally support material formulation(s), and all are selected to include materials or combination of materials that do not interfere with the biological and/or structural features of the biological components.

In some of any of the embodiments described herein, the bioprinting method is configured to effect formation of the layers under conditions that do not significantly affect structural and/or functional properties of the biological components in the bio-ink.

In some embodiments, a bioprinting system for effecting a bioprinting process/method as described herein is configured so as to allow formation of the layers under conditions that do not significantly affect structural and/or functional properties of the biological components in the bio-ink.

In some of any of the embodiments described herein, the additive manufacturing (e.g., bioprinting) process and system are configured such that the process parameters (e.g., temperature, shear forces, shear strain rate) do not interfere with (do not substantially affect) the functional and/or structural features of the biological components.

The following describes exemplary AM bioprinting methodologies that are usable in the context of embodiments of the present invention.

A bioprinting method and a corresponding system can be any of the methods and systems known in the art for performing additive manufacturing, and exemplary such systems and methods are described hereinabove. A suitable method and system can be selected upon considering its printing capabilities, which include resolution, deposition speed, scalability, bio-ink compatibility and ease-of-use.

Exemplary suitable bioprinting systems usually contain a dispensing system (either equipped with temperature control module or at ambient temperature), and stage (a receiving medium), and a movement along the x, y and z axes directed by a CAD-CAM software. A curing source (e.g., a light or heat source) which applies a curing energy (e.g., by applying light or heat radiation) or a curing condition to the deposition area (the receiving medium) so as to promote curing of the formed layers and/or a humidifier, can also be included in the system. There are printers that use multiple dispensing heads to facilitate a serial dispensing of several materials.

Generally, bioprinting can be effected using any of the known techniques for additive manufacturing. The following lists some exemplary additive manufacturing techniques, although any other technique is contemplated.

3D Inkjet Printing:

3D Inkjet printing is a common type of 3D printer for both non-biological and biological (bioprinting) applications. Inkjet printers use thermal or acoustic forces to eject drops of liquid onto a substrate, which can support or form part of the final construct. In this technique, controlled volumes of liquid are delivered to predefined locations, and a high-resolution printing with precise control of (1) ink drops position, and (2) ink volume, which is beneficial in cases of microstructure-printing or when small amounts of bioreactive agents or drugs are added, is received. Inkjet printers can be used with several types of ink, for example, comprising multiple types of biological components and/or bioactive agents. Furthermore, the printing is fast and can be applied onto culture plates.

A bioprinting method that utilizes a 3D inkjet printing system can be operated using one or more bio-ink modeling material formulations as described herein, and dispensing droplets of the formulation(s) in layers, on the receiving medium, using one or more inkjet printing head(s), according to the 3D printing data.

Extrusion Printing:

This technique uses continuous beads of material rather than liquid droplets. These beads of material are deposited in 2D, the stage (receiving medium) or extrusion head moves along the z axis, and the deposited layer serves as the basis for the next layer. The most common methods for biological materials extrusion for 3D bioprinting applications are pneumatic or mechanical dispensing systems.

Stereolithography (SLA) and Digital Light Processing (DLP):

SLA and DLP are additive manufacturing technologies in which an uncured building material in a bath is converted into hardened material(s), layer by layer, by selective curing using a light source while the uncured material is later separated/washed from the hardened material. SLA is widely used to create models, prototypes, patterns, and production parts for a range of industries including for Bioprinting.

Laser-Assisted Printing:

Laser-assisted printing technique, in the version adopted for 3D bioprinting, and is based on the principle of laser-induced forward transfer (LIFT), which was developed to transfer metals and is now successfully applied to biological material. The device consists of a laser beam, a focusing system, an energy absorbing/converting layer and a biological material layer (e.g., cells and/or hydrogel) and a receiving substrate. A laser assisted printer operates by shooting a laser beam onto the absorbing layer which convert the energy into a mechanical force which drives tiny drops from the biological layer onto the substrate. A light source is then utilized to cure the material on the substrate.

Laser assisted printing is compatible with a series of viscosities and can print mammalian cells without affecting cell viability or cell function. Cells can be deposited at a density of up to $10^8$ cells/ml with microscale resolution of a single cell per drop.

Electro Spinning:

Electrospinning is a fiber production technique, which uses electric force to draw charged threads of polymer solutions, or polymer melts. According to some of the present embodiments described herein, in at least one of the layers formed during the AM (bioprinting process), the dispensed modeling material formulation comprises a biological component or material as described herein and is regarded as bio-ink, as described herein.

According to the present embodiments, the building material comprises at least one modeling material formulation that comprises a curable fibrinogen (a bio-ink), as described herein in any of the respective embodiments. Such a modeling material formulation is also referred to herein a curable formulation or as a curable fibrinogen formulation, and is preferably a curable formulation as described herein in any of the respective embodiments.

A concentration of the curable fibrinogen in a modeling material formulation containing same can affect the rheological properties of the formulation and of the hardened formulation obtained upon dispensing, and can be manipulated in accordance with AM methodology and conditions employed and desired properties of the final object or a portion thereof.

According to some of any of the embodiments described herein, the printing media (the building material) comprises one or more additional materials, including, for example, one or more additional curable materials, one or more non-curable materials and/or one or more biological components, as described herein in any of the respective embodiments.

According to some of any of the embodiments described herein, the printing media (the building material) comprises a cross-linking agent as described herein.

According to some of any of the embodiments described herein, the additional materials are included in the conjugate-containing curable formulation as described herein or in one or more other modeling material formulations.

Additional curable materials that can be included in the curable formulation or in one or more other modeling material formulations can be any curable material as defined herein, and is preferably a biocompatible material.

In some embodiments the additional curable material is or comprises a hydrogel, as defined herein, which can form a hardened modeling material, typically upon further cross-linking and/or co-polymerization, when exposed to a curing condition at which the cross-linking and/or co-polymerization reaction occurs. Such curable materials are also referred to herein as hydrogel curable materials.

In some embodiments the additional curable material is a cross-linking agent, as defined herein, which can be included in a modeling material formulation that comprises the curable fibrinogen, or in a different modeling material formulation, which may optionally further comprise a carrier. The ratio between the cross-linking agent and the curable fibrinogen at any location can be pre-determined.

According to some of any of the embodiments described herein, one or more the modeling material formulations further comprises cells. The cells can be included in curable formulation that comprises the curable fibrinogen, or in any other modeling material formulation.

Herein throughout, in the context of AM or bioprinting, the term "object" describes a final product of the additive manufacturing which comprises, in at least a portion thereof, a biological component. This term refers to the product obtained by a bioprinting method as described herein, after removal of the support material, if such has been used as part of the uncured building material.

The term "object" as used herein throughout refers to a whole object or a part thereof.

In the context of the present embodiments, the object comprises in at least a portion thereof a fibrinogen-based material.

In some of any of the embodiments described herein, the fibrinogen-based material comprises a scaffold, for example, a hydrogel scaffold, made of a three-dimensional fibrillar network that comprises fibrinogen as described herein. In some of any of the embodiments described herein, the object is in a form of a tissue or organ, which comprises, in at least a portion thereof, a fibrinogen-based material as described herein. Such an object can be formulated in accordance with a respective 3D printing data of a desired organ or tissue, using, in addition to the curable fibrinogen as described herein, additional curable materials and biological materials as described herein.

In some embodiments, the object is an implantable object.

In some embodiments, the object is usable in, or is for use in, constructing an artificial organ or tissue.

The object can further comprise hardened materials formed of one or more of the additional curable materials as described herein in any of the respective embodiments, biological components or materials, as described herein in any of the respective embodiments, and/or non-curable materials as described herein in any of the respective embodiments.

In some embodiments, the object is in a form of a scaffold or film, that can be used in research or therapeutic applications, for example, in repairing a damaged tissue, for example, upon seeding culturing cells therein, or in wound healing.

The object of the present embodiments comprises a myriad of other uses including, but not limited to, in the treatment of diseases such as interstitial cystitis, scleroderma, and rheumatoid arthritis cosmetic surgery, as a healing aid for burn patients, as a wound-healing agent, as a dermal filler, for spinal fusion procedures, for urethral bulking, in duraplasty procedures, for reconstruction of bone and a wide variety of dental, orthopedic and surgical purposes.

The object can be used in any of the methods described herein for a scaffold that is formed ex-vivo.

According to an aspect of some embodiments of the present invention, there is provided a kit that comprises a curable fibrinogen or a curable formulation as described herein in any of the respective embodiments, which is identified for use, or is usable, as a modeling material formulation for additive manufacturing (e.g., bioprinting) of an object as described herein in any of the respective embodiments.

According to some of any of the embodiments described herein, the kit further comprises an aqueous carrier, as described herein in any of the respective embodiments.

In some embodiments, the composition and the aqueous carrier are packaged individually within the kit.

Alternatively, the kit includes instructions to prepare a modeling material formulation as described herein, by mixing the composition with the aqueous carrier.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Herein, the phrase "linking group" describes a group (e.g., a substituent) that is attached to two or more moieties in the compound; whereas the phrase "end group" describes a group (e.g., a substituent) that is attached to a single moiety in the compound via one atom thereof.

Herein, the term "hydrocarbon" describes an organic moiety that includes, as its basic skeleton, a chain of carbon atoms, also referred to herein as a backbone chain, substituted mainly by hydrogen atoms. The hydrocarbon can be saturated or unsaturated, be comprised of aliphatic, alicyclic and/or aromatic moieties, and can optionally be substituted by one or more substituents (other than hydrogen). A substituted hydrocarbon may have one or more substituents, whereby each substituent group can independently be, for example, alkyl, cycloalkyl, alkenyl, alkynyl, alkaryl, aryl, heteroaryl, heteroalicyclic, amine, halo, sulfonate, sulfoxide, phosphonate, hydroxy, alkoxy, aryloxy, thiohydroxy, thioalkoxy, thioaryloxy, cyano, nitro, azo, azide, sulfonamide, carboxy, thiocarbamate, urea, thiourea, silyl, carbamate, amide, and hydrazine, and any other substituents as described herein.

The hydrocarbon moiety can optionally be interrupted by one or more heteroatoms, including, without limitation, one or more oxygen, nitrogen (substituted or unsubstituted, as defined herein for —NR'—) and/or sulfur atoms.

In some embodiments of any of the embodiments described herein the hydrocarbon is not interrupted by any heteroatom, nor does it comprise heteroatoms in its backbone chain, and can be an alkylene chain, or be comprised of alkyls, cycloalkyls, aryls, alkenes and/or alkynes, covalently attached to one another in any order.

As used herein throughout, the term "alkyl" refers to any saturated aliphatic hydrocarbon including straight chain and branched chain groups. Preferably, the alkyl group has 1 to 20 carbon atoms. Whenever a numerical range; e.g., "1 to 20", is stated herein, it implies that the group, in this case the hydrocarbon, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein.

Herein, the term "alkenyl" describes an unsaturated aliphatic hydrocarbon comprise at least one carbon-carbon double bond, including straight chain and branched chain groups. Preferably, the alkenyl group has 2 to 20 carbon atoms. More preferably, the alkenyl is a medium size alkenyl having 2 to 10 carbon atoms. Most preferably, unless otherwise indicated, the alkenyl is a lower alkenyl having 2 to 4 carbon atoms. The alkenyl group may be substituted or non-substituted. Substituted alkenyl may have one or more substituents, whereby each substituent group can independently be, for example, alkynyl, cycloalkyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino.

Herein, the term "alkynyl" describes an unsaturated aliphatic hydrocarbon comprise at least one carbon-carbon triple bond, including straight chain and branched chain groups. Preferably, the alkynyl group has 2 to 20 carbon atoms. More preferably, the alkynyl is a medium size alkynyl having 2 to 10 carbon atoms. Most preferably, unless otherwise indicated, the alkynyl is a lower alkynyl having 2 to 4 carbon atoms. The alkynyl group may be substituted or non-substituted. Substituted alkynyl may have one or more substituents, whereby each substituent group can independently be, for example, cycloalkyl, alkenyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino.

The term "alkylene" describes a saturated or unsaturated aliphatic hydrocarbon linking group, as this term is defined herein, which differs from an alkyl group (when saturated) or an alkenyl or alkynyl group (when unsaturated), as defined herein, only in that alkylene is a linking group rather than an end group.

A "cycloalkyl" group refers to a saturated on unsaturated all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein. When a cycloalkyl group is unsaturated, it may comprise at least one carbon-carbon double bond and/or at least one carbon-carbon triple bond. The cycloalkyl group can be an end group, as this phrase is defined herein, wherein it is attached to a single adjacent atom, or a linking group, as this phrase is defined herein, connecting two or more moieties.

An "aryl" group refers to an all-carbon monocyclic or fused-ring polycyclic (i.e., rings which share adjacent pairs of carbon atoms) end groups having a completely conjugated pi-electron system. Examples, without limitation, of aryl groups are phenyl, naphthalenyl and anthracenyl. The aryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein.

A "heteroaryl" group refers to a monocyclic or fused ring (i.e., rings which share an adjacent pair of atoms) end group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein.

The term "arylene" describes a monocyclic or fused-ring polycyclic linking group, as this term is defined herein, and encompasses linking groups which differ from an aryl or heteroaryl group, as these groups are defined herein, only in that arylene is a linking group rather than an end group.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. When substituted, the substituted group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, oxo, imine, oxime, hydrazone, carbonyl, thiocarbonyl, a urea group, a thiourea group, O-carbamyl, N-carbamyl, O-thiocarbamyl, N-thiocarbamyl, S-thiocarbamyl, C-amido, N-amido, C-carboxy, O-carboxy, sulfonamido, guanyl, guanidinyl, hydrazine, hydrazide, thiohydrazide, and amino, as these terms are defined herein. Representative examples are piperidine, piperazine, tetrahydrofuran, tetrahydropyran, morpholine and the like. The heteroalicyclic group can be an end group, as this phrase is defined herein, wherein it is attached to a single adjacent atom, or a linking group, as this phrase is defined herein, connecting two or more moieties.

Herein, the terms "amine" and "amino" each refer to either a —NR'R" group or a —N⁺R'R"R'" group, wherein R', R" and R'" are each hydrogen or a substituted or non-substituted alkyl, alkenyl, alkynyl, cycloalkyl, heteroalicyclic (linked to amine nitrogen via a ring carbon thereof), aryl, or heteroaryl (linked to amine nitrogen via a ring carbon thereof), as defined herein. Optionally, R', R" and R'" are hydrogen or alkyl comprising 1 to 4 carbon atoms. Optionally, R' and R" (and R'", if present) are hydrogen. When substituted, the carbon atom of an R', R" or R'" hydrocarbon moiety which is bound to the nitrogen atom of the amine is not substituted by oxo (unless explicitly indicated otherwise), such that R', R" and R'" are not (for example) carbonyl, C-carboxy or amide, as these groups are defined herein.

An "azide" group refers to a —N=N⁺=N⁻ end group.

An "alkoxy" group refers to any of an —O-alkyl, —O-alkenyl, —O-alkynyl, —O-cycloalkyl, and —O-heteroalicyclic end group, as defined herein, or to any of an —O-alkylene, —O-cycloalkyl- and —O-heteroalicyclic-linking group, as defined herein.

An "aryloxy" group refers to both an —O-aryl and an —O-heteroaryl group, as defined herein, or to an —O-arylene.

A "hydroxy" group refers to a —OH group.

A "thiohydroxy" or "thiol" group refers to a —SH group.

A "thioalkoxy" group refers to any of an —S-alkyl, —S-alkenyl, —S-alkynyl, —S-cycloalkyl, and —S-heteroalicyclic end group, as defined herein, or to any of an —S-alkylene-, —S-cycloalkyl- and —S-heteroalicyclic-linking group, as defined herein.

A "thioaryloxy" group refers to both an —S-aryl and an —S-heteroaryl group, as defined herein, or to an —S-arylene.

A "carbonyl" or "acyl" group refers to a —C(=O)—R' end group, where R' is defined as hereinabove, or to a —C(=O)— linking group.

A "thiocarbonyl" group refers to a —C(=S)—R' end group, where R' is as defined herein, or to a —C(=S)— linking group.

A "carboxy", "carboxyl", "carboxylic" or "carboxylate" group refers to both "C-carboxy" and "O-carboxy" end groups, as defined herein, as well as to a carboxy linking group, as defined herein.

A "C-carboxy" group refers to a —C(=O)—O—R' group, where R' is as defined herein.

An "O-carboxy" group refers to an R'C(=O)—O— group, where R' is as defined herein.

A "carboxy linking group" refers to a —C(=O)—O— linking group.

An "oxo" group refers to a =O end group.

An "imine" group refers to a =N—R' end group, where R' is as defined herein, or to an =N— linking group.

An "oxime" group refers to a =N—OH end group.

A "hydrazone" group refers to a =N—NR'R" end group, where each of R' and R" is as defined herein, or to a =N—NR'— linking group where R' is as defined herein.

A "halo" group refers to fluorine, chlorine, bromine or iodine.

A "sulfinyl" group refers to an —S(=O)—R' end group, where R' is as defined herein, or to an —S(=O)— linking group.

A "sulfonyl" group refers to an —S(=O)₂—R' end group, where R' is as defined herein, or to an —S(=O)₂— linking group.

A "sulfonate" group refers to an —S(=O)₂—O—R' end group, where R' is as defined herein, or to an —S(=O)₂—O— linking group.

A "sulfate" group refers to an —O—S(=O)₂—O—R' end group, where R' is as defined as herein, or to an —O—S(=O)₂—O— linking group.

A "sulfonamide" or "sulfonamido" group encompasses both S-sulfonamido and N-sulfonamido end groups, as defined herein, as well as a sulfonamide linking group, as defined herein.

An "S-sulfonamido" group refers to a —S(=O)₂—NR'R" end group, with each of R' and R" as defined herein.

An "N-sulfonamido" group refers to an R'S(=O)₂—NR"— end group, where each of R' and R" is as defined herein.

A "sulfonamide linking group" refers to a —S(=O)₂—NR'— linking group, where R' is as defined herein.

A "carbamyl" group encompasses both O-carbamyl and N-carbamyl end groups, as defined herein, as well as a carbamyl linking group, as defined herein.

An "O-carbamyl" group refers to an —OC(=O)—NR'R" end group, where each of R' and R" is as defined herein.

An "N-carbamyl" group refers to an R'OC(=O)—NR"— end group, where each of R' and R" is as defined herein.

A "carbamyl linking group" refers to a —OC(=O)—NR'— linking group, where R' is as defined herein.

A "thiocarbamyl" group encompasses O-thiocarbamyl, S-thiocarbamyl and N-thiocarbamyl end groups, as defined herein, as well as a thiocarbamyl linking group, as defined herein.

An "O-thiocarbamyl" group refers to an —OC(=S)—NR'R" end group, where each of R' and R" is as defined herein.

An "N-thiocarbamyl" group refers to an R'OC(=S)NR"— end group, where each of R' and R" is as defined herein.

An "S-thiocarbamyl" group refers to an —SC(=O)—NR'R" end group, where each of R' and R" is as defined herein.

A "thiocarbamyl linking group" refers to a —OC(=S)—NR'— or —SC(=O)—NR'— linking group, where R' is as defined herein.

An "amide" or "amido" group encompasses C-amido and N-amido end groups, as defined herein, as well as an amide linking group, as defined herein.

A "C-amido" group refers to a —C(=O)—NR'R" end group, where each of R' and R" is as defined herein.

An "N-amido" group refers to an R'C(=O)—NR"— end group, where each of R' and R" is as defined herein.

An "amide linking group" refers to a —C(=O)—NR'— linking group, where R' is as defined herein.

A "urea group" refers to an —N(R')—C(=O)—NR"R'" end group, where each of R', R" and R'" is as defined herein, or an —N(R')—C(=O)—NR"— linking group, where each of R' and R" is as defined herein.

A "thiourea group" refers to an —N(R')—C(=S)—NR"R'" end group, where each of R', R" and R'" is as defined herein, or an —N(R')—C(=S)—NR"— linking group, where each of R' and R" is as defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined herein, or a —P(=O)(OR')—O— linking group, with R' as defined herein.

The term "phosphate" describes an —O—P(=O)(OR')(OR") end group, with each of R' and R" as defined herein, or an —O—P(=O)(OR')—O— linking group, with R' as defined herein.

The term "phosphinyl" describes a —PR'R" end group, with each of R' and R" as defined herein, or a —PR'— linking group, with R' as defined herein.

The term "hydrazine" describes a —NR'—NR"R'" end group, where R', R", and R'" are as defined herein, or to a —NR'—NR"— linking group, where R' and R" are as defined herein.

As used herein, the term "hydrazide" describes a —C(=O)—NR'—NR"R'" end group, where R', R" and R'" are as defined herein, or to a —C(=O)—NR'—NR"— linking group, where R' and R" are as defined herein.

As used herein, the term "thiohydrazide" describes a —C(=S)—NR'—NR"R'" end group, where R', R" and R'" are as defined herein, or to a —C(=S)—NR'—NR"— linking group, where R' and R" are as defined herein.

A "guanidinyl" group refers to an —RaNC(=NRd)-NRbRc end group, where each of Ra, Rb, Rc and Rd can be as defined herein for R' and R", or to an —R'NC(=NR")—NR'"— linking group, where R', R" and R'" are as defined herein.

A "guanyl" or "guanine" group refers to an R" 'R"NC (=NR')— end group, where R', R" and R'" are as defined herein, or to a —R"NC(=NR')— linking group, where R' and R" are as defined herein.

As used herein, the term "alkylene glycol" describes a —O—[(CR'R")$_z$—O]$_y$—R'" end group or a —O—[(CR'R")$_z$—O]$_y$— linking group, with R', R" and R'" being as defined herein, and with z being an integer of from 1 to 10, preferably, from 2 to 6, more preferably 2 or 3, and y being an integer of 1 or more. Preferably R' and R" are both hydrogen. When z is 2 and y is 1, this group is ethylene glycol. When z is 3 and y is 1, this group is propylene glycol. When y is 2-4, the alkylene glycol is referred to herein as oligo(alkylene glycol).

When y is greater than 4, the alkylene glycol is referred to herein as poly(alkylene glycol) or as poly(alkylene oxide). In some embodiments of the present invention, a poly(alkylene glycol) group or moiety can have from 10 to 200 repeating alkylene glycol units, such that z is 10 to 200, preferably 10-100, more preferably 10-50.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:

Fibrinogen was obtained from Seqens In Vitro Diagnostic (reference 2000-70).

Dulbecco's Modified Eagle's Medium (DMEM) was obtained from Gibco, UK.

Fetal bovine serum (FBS), penicillin-streptomycin-ampicillin and trypsin-EDTA were obtained from Biological Industries, Israel.

Linear poly(ethylene glycol) (PEG, 10 kDa) was obtained from Merck KGaA, Darmstadt, Germany.

Star polyethylene oxide (PEO) (4-arm, 20 kDa) and star polyethylene oxide (PEO) (8-arm, 20 kDa) were obtained from Nektar, San Francisco, California.

Herein throughout, polyethylene oxide or PEO are also referred to interchangeably as poly(ethylene glycol) or PEG.

All other materials were obtained from Sigma-Aldrich and used without further modifications or purifications.

NMR Analysis: NMR measurements of the PEG-acrylate and FibMA samples were performed on a Bruker Avance 400 MHz spectrometer. Chemical shifts for $^1$H-NMR are referenced to internal proton-solvent resonances. Samples were dissolved in deuterium oxide ($D_2O$) or chloroform ($CDCl_3$) to a final concentration of 10 mg/ml and the measurements were carried out at room temperature in standard NMR tubes.

Degree of Conversion (DC): The extent of FibMA methacrylation (i.e., the degree of conversion, DC) was determined by $^1$H-NMR spectroscopy using 3-(trimethylsilyl) propionic-2,2,3,3-$d_4$ (TMSP) acid (Sigma-Aldrich, Germany) as an internal reference. All the $^1$H-NMR samples were papered by dissolving 8 mg of each sample in 800 μL of deuterium oxide with 0.5% (w/v) TMSP. The chemical shift scale and the integration were adjusted to the TMSP signal ($\delta(H)=0$ ppm). The DC was calculated using the following formula in which 9H relates to the three $CH_3$ groups of the TMSP, and 2H relates to the two hydrogens at the double bond of the methacryloyl group:

$$DC = \frac{\int \text{methacryloyl(the peaks at 5.2--5.8 ppm)}}{\int TMSP\text{(at 0 ppm)}} \cdot \frac{9H}{2H} \cdot \frac{n(mmole \text{ of } TMSP)}{m(g \text{ of sample})}$$

Acrylation of Poly(ethylene Oxide) (PEO): PEO-diacrylate (PEO-DA), star PEG with 4 acrylates per PEG (PEG-tetra-acrylate, PEG-TA) and star PEG with 8 acrylates per PEG (PEG-octa-acrylate, PEG-OA) were prepared as previously described [Halstenberg et al. Biomacromolecules 3, 710-723 (2002)]. Briefly, anhydrous PEG was reacted with acryloyl chloride at a molar ratio of 1.75:1 relative to the hydroxyl groups on the respective PEG variant. The reaction was carried out under argon in a solution of dichloromethane in the presence of triethylamine. The final products were precipitated in ice-cold diethylether, dried under vacuum for 48 hours, and stored under argon at −80° C. The end-group conversion was confirmed by $^1$H-NMR spectroscopy (data not shown).

Cell-Laden Construct Preparation: Human neonatal dermal fibroblasts (NHDF, Lonza, Israel) were sub-cultured on tissue culture plastic with growth medium comprised of Dulbecco's Modified Eagle's Medium (DMEM, Gibco, UK), 10% fetal bovine serum (FBS) and 1% penicillin-streptomycin-ampicillin (Biological Industries, Israel). The cells were trypsinized using 0.25% trypsin-EDTA (Biological Industries, Israel) and suspended with an FibMA hydrogel precursor solution containing 0.1% w/v photoinitiator and PEG-TA. The FibMA/cell suspension was placed in cylindrical molds (5 mm diameter and 60 μl hydrogel precursor per mold) to form constructs with a final cell density of $3 \times 10^6$ cells/ml. The constructs were cross-linked using blue light photochemistry (405 nm, 2 mW/cm², 1 minute). The cell-laden constructs were incubated in multi-well culture plates with DMEM growth medium for up to three weeks with replenishment of growth medium every 2 days.

Cell Viability: The viability of the cells grown in the hydrogel constructs was confirmed by a Calcein/Ethidium Live/Dead assay, which stains the live cells in green and dead cells in red. For this purpose, 1 ml of PBS solution containing 4 mM calcein acetoxymethyl ester, 2 mM ethidium homodimer-1 was added to each well in 12-well plates containing a single hydrogel construct and incubated for 45 minutes on an orbital shaker at 37° C. After staining, the plugs were washed with PBS for 10 minutes. Cells were microscopically imaged using Zeiss LSM 700 confocal microscope (Carl Zeiss, Oberkochen, Germany).

Cell Proliferation Assay: A Cell Counting Kit-8 (CCK-8) (Sigma-Aldrich, USA) assay was used to determine the proliferation activity of NHDFs (40 μl cell-laden constructs contain $0.5 \times 10^6$ cells/ml). Two different FibMA hydrogel formulations were tested: $FibMA_{0.2\%}$ with 1.6% PEG-TA, $FibMA_{0.1\%}$ with 1.8% PEG-TA. A control PEG hydrogel made from 2.5% PEG-TA was also tested. After 1, 3 and 7 days of in vitro cell culture, the constructs were placed in 96-well plates with 100 μL culture medium containing 10% CCK-8 assay solution. The samples were incubated for 2 hours at 37° C. and 5% $CO_2$. The optical density of the solution was measured at 450 nm (OD450) and detected with a microplate reader (Model 800 TS, Bio-Tek, USA). The optical density at 450 nm was shown to be directly proportional to the number of NHDF cells.

Animals Studies: All procedures were carried out in accordance with the National Institutes of Health Guide for care and use of laboratory animals and were approved by the Animal Ethics Committee of the Technion, Haifa, Israel. C57BL/6 mice (8 weeks) were anesthetized by intramuscular injections of Ketamine (40 mg/kg) and Xylasine (15 mg/kg) and dorsal subcutaneous pocket was formed. A single hydrogel implant was inserted into the pocket and the incision was closed with suture. Animals were checked once a week until 8 weeks post implantation for any abnormalities in the behavior or at the wound site. Animals were humanly sacrificed after 8 weeks.

Histological Assessment: Following sacrifice, all tissue samples were processed for histology by first placing the skin samples in paraformaldehyde solution (4% in PBS, Santa Cruz Biotechnology, Dallas, TX, USA) and then embedding the tissue in paraffin. Sections of the specimen (4-5 μm thick) were obtained at distinct time points in the experiment, including week 1, week 3, and week 8. These were stained with Hematoxylin & Eosin (H&E, Sigma) and scanned using the Panoramic 250 Flash III automated digital scanner (3D Histech Ltd, Budapest, Hungary) using a 20X/ 0.8 Plan Apochromat objective.

Statistical Analysis: All the results are expressed as the mean±standard deviation (SD). GraphPad Prism 9 software was used for all the statistical analysis. For each variable, data from at least three independent experiments were measured and analyzed, unless otherwise stated. One-way analysis of variance (ANOVA) was performed for comparison of quantitative properties of hydrogels where a single parameter was examined. Two-way ANOVA was performed for comparison where two parameters were examined. A $p<0.05$ was used to signify a statistically significant difference in the data.

Example 1

Preparation of Fibrinogen-MA Hydrogels

Generally stated, according to some embodiments of the present invention, the fibrinogen molecules are transformed into FibMA hydrogels using two sequential steps: 1) fibrinogen methacrylation; and 2) 3-D matrix formation, as described in further detail in the following.

Fibrinogen Methacrylation (Preparation of Fibrinogen Featuring Methacrylic Groups):

Methacrylated Fibrinogen, FibMA, was prepared by chemically conjugating methacrylic groups to the free amines on the fibrinogen (mainly through the Lysine amino acid residues, although other amino acid residues are also contemplated), as generally depicted in FIGS. 2A-B. Fibrinogen molecules were reacted with methacrylic anhydride (MAA) to form FibMA hydrogel precursor. The heteromeric fibrinogen is comprised of two subunits of three chains each, held together by disulfide rings. The MAA reacts, for example, with amine groups (e.g., of the lysine residues), as shown in FIG. 2B, and possibly also with hydroxy groups at the side chain of other amino acid residues, as shown in FIG. 2A, on the polypeptides to form the FibMA molecule. Methacrylic acid is also produced by this reaction.

Fibrinogen (0.5 gram, 0.309 mmole of lysine residues), was dissolved at 10% (w/v) in phosphate buffered saline (PBS; 150 mM) with 8M urea, at room temperature, and the pH of the solution was adjusted to 9.4 by adding 2M NaOH. An excess of methacrylic anhydride MAA (1.7 mmole, 254 $\mu$l; 0.4% v/v) was added to the fibrinogen solution and the reaction mixture was stirred for 2-3 hours at room temperature. Other variants of FibMA were made similarly but with different v/v concentrations of MAA (e.g., FibMA$_{0.2\%}$, FibMA$_{0.1\%}$, and FibMA$_{0.05\%}$, which refer to FibMA with 0.2%, 0.1% and 0.05%, v/v, MAA, respectively). The pH of the solution was maintained at 9.0-9.4 with constant stirring by adding 2M NaOH. The reaction was completed when the pH of the solution stabilized. The final pH of the solution was adjusted to 7.4 to stop the reaction by adding 2M HCl solution. The final product was filtered and dialyzed against PBS (150 mM) at 4° C. for 2 days with at least two changes of PBS per day (Spectrum, 12-14 kDa MW cutoff). FibMA was sterilized by filtering through 0.22 $\mu$m filter (produced by Merck KGaA, Darmstadt, Germany). The Nanodrop techniques was used in order to determine the fibrinogen concentration in the samples (Thermo Scientific™ Nano-Drop 2000).

FibMA Hydrogel Formation:

The FibMA hydrogel precursor is water soluble and can be injected as a liquid precursor for in situ gelation, or alternatively, it can be formed into a 3-D matrix ex situ and implanted thereafter. The formation of the hydrogel from the FibMA precursor can be facilitated by a number of cross-linking reactions that conjugate the reactive methacrylate groups, thus connecting the fibrinogen molecules into a contiguous polymer network. Using a light activated free radical polymerization reaction, for example, the FibMA chains are crosslinked rapidly into a hydrogel in the presence of a photo-initiator and light. Additional functionalized polymeric constituents may be added to the mixture in order to change the mechanical properties and biodegradation properties of the hydrogel. The addition of PEO-diacrylate (PEO-DA) and other multi-functional PEO-acrylates has been demonstrated herein as a representative example, and was shown to alter the mechanical properties of the FibMA matrix.

Generally, a hydrogel was formed by mixing the FibMA precursor solution (5-20 mg/ml) with PEO-diacrylate (PEO-DA or PEG-DA), PEO-triacrylate (PEO-TA or PEG-TA), or PEO-octaacrylate (PEO-OA or PEG-OA) (10-20 kDa, 0.5-3% w/v), which was added to increase cross-linking density of the FibMA network. The precursor solution was mixed with 0.1% (v/v) photoinitiator (from a stock solution made of 10% w/v Irgacure™2959 (Ciba Specialty Chemicals, Tarrytown, New York.) in 70% ethanol and deionized water). The solution was subjected to a UV light irradiation (365 nm, 5 mW/cm$^2$) for 5 minutes to thereby polymerize into a hydrogel. Alternatively, the precursor solution can be mixed with 0.1% Lithium phenyl-2,4,6-trimethylbenzoylphosphinate (LAP) photoinitiator and subjected to blue light irradiation (405 nm, 2 mW/cm$^2$) for 1 minute.

Example 2

Characterization

Degree of Modification:

The chemical conjugation of methacrylic groups to the free amines on e.g., the lysine amino acid residues of the fibrinogen was controlled by mixing stoichiometric quantities of methacrylic anhydride (MMA) used in the reaction, based on the actual known number of lysine residues on the fibrinogen polypeptides (See, FIG. 1). Each fibrinogen molecule (three polypeptide chains) contains 103 lysine residues. This ratio of fibrinogen molecules (nFibrinogen) to lysine residues (nLysine) is thus 1:103. The ratio of lysine residues to MMA molecules (nMMA) determines the final degree of the fibrinogen methacrylation.

For the purpose of demonstrating the ability to control the degree of methacrylation, several reactions were carried out at different ratios (nLysine:nMMA), as described in Table 1 hereinbelow.

The resulting products from each reaction were characterized by NMR.

Proton NMR (i.e., $^1$H-NMR) is a technique that can be used to verify the chemical conjugation of methacrylate moieties on the fibrinogen backbone. Although the technique cannot quantify this reaction, the chemical modifications can be identified qualitatively by comparing the $^1$H-NMR spectra of the fibrinogen to the FibMA spectra.

FIG. 3A shows representative spectra of both native and methacrylated fibrinogen (i.e., FibMA), with the new proton peaks belonging to methacryloyl groups of FibMA appearing between 6.4-5.3 ppm and at 1.9 ppm. FibMA displayed specific chemical shifts between 5.9-5.8 and 5.6-5.3 ppm for acrylic protons (C$\underline{H}_2$=C(CH$_3$)CONH—) of methacrylamide groups and at 1.9 ppm for methyl protons (CH$_2$=C(C$\underline{H}_3$)CO—) of methacryloyl groups, as well as additional small peaks at 6.1 ppm for acrylic protons (CH$_2$=C(CH$_3$)COO—) of methacrylate groups. FIG. 3B presents another representative spectra, showing the new proton peaks belonging to methacryloyl groups of FibMA$_{0.4\%}$ appearing between 5.8-5.3 ppm and at 2.2 ppm. It can be seen that all the FibMA conjugates display specific chemical shifts between 5.7-5.3 ppm for acrylic protons (C$\underline{H}_2$=C(CH$_3$)CONH—) of methacrylamide groups and at 2.2 ppm for methyl protons of methacrylamide groups (CH$_2$=C(C$\underline{H}_3$)CO—), as well as an additional small peak at 5.8 ppm for the amide proton (CON$\underline{H}$).

Quantitative $^1$H-NMR analysis was used to determine the degree of conjugation (DC) in the FibMA product. The quantification uses an internal reference, 3-(trimethylsilyl) propionic-2,2,3,3-d$_4$ (TMSP) acid, as described hereinabove. The DC in FibMA products was calculated for at least 3 different batches and is summarized in Table 1 below. The most right column shows the factor by which the DC in FibMA (FibMA$_{0.4\%}$) is higher compared to the other products.

TABLE 1

| Reaction | n(lysine):n(MAA) | DC (mmol/gram) (mean ± SD; n = 3) | FibMA$_{0.4\%}$ DC/product DC |
|---|---|---|---|
| FibMA (FibMA$_{0.4\%}$) | 1:5.7 | 0.306 ± 0.052 | 1 |
| FibMA0.5 (FibMA$_{0.2\%}$) | 1:2.85 | 0.166 ± 0.006 | 1.85 ± 0.26 |
| FibMA0.25 (FibMA$_{0.1\%}$) | 1:1.42 | 0.0725 ± 0.005 | 4.24 ± 0.55 |
| FibMA0.125 (FibMA$_{0.05\%}$) | 1:0.71 | 0.027 ± 0.005 | 11.42 ± 0.23 |

Fourier-transform infrared spectroscopy (FTIR) is also a technique that was used to obtain an infrared spectrum of absorption or emission of the FibMA. FTIR measurements were performed using a Bruker Tensor 27 spectrometer equipped with TGS detector and Bruker Platinum ATR, diamond, single reflection accessory. Spectra were collected in ATR mode over the wavenumber range 4000-600 cm$^{-1}$ at 4 cm$^{-1}$ resolution. Background was subtracted using the Opus software (Bruker Instruments, Billerica, MA). Both native fibrinogen (red) and FibMA (blue) were analyzed using this technique, before and after the methacrylation reaction, and the obtained spectra are shown in FIG. 4A. A new peak can be seen around 980 ppm. FibMA conjugates having different degrees of methacrylation were also analyzed in the FTIR to identify the new peak in the all the variations tested. FIG. 4B presents the spectra of the four tested variants; each variant showing the new peak at around 980 ppm.

Mechanical Properties:

The mechanical (e.g., rheological) properties of the FibMA were characterized by oscillatory shear rheometry. A TA Instruments AR-G2 rheometer (New Castle, DE, USA), with 20-mm parallel plate geometry was used to characterize the different batches of the FibMA$_{0.4\%}$ under constant strain oscillatory shear. Each measurement was conducted using 200 μl of the precursor solution with 0.1% (w/v) Irgacure 2959 photoinitiator (Ciba, Basel, Switzerland) and gap size of 400 μm. The samples were cross-linked by irradiation with UV light (365 nm, 5 mW/cm$^2$) after 15 seconds until the shear storage modulus reaches its plateau value. Time sweep oscillatory tests were conducted under constant strain amplitude of 1% and a constant frequency of 2 Hz, which was determined to be the linear viscoelastic (LVR) region of the FibMA.

The obtained data is presented in FIGS. 5A-B, and show that the shear storage and loss moduli (G' and G", respectively) show constant values within the linear viscoelastic regions (LVR) both under amplitude sweep (FIG. 5A) and frequency sweep (FIG. 5B) measurements.

As shown, in the LVR region, the storage modulus was higher than the loss modulus (G'>G"), indicating that the obtained FibMA hydrogel behaves like a gel, or solid-like structure. The extended range of the LVR indicates high stability of the FibMA hydrogel.

The shear storage modulus of the FibMA$_{0.4\%}$ was characterized for hydrogels made of formulations that included a multi-functional PEO-acrylate (acting as a crosslinker) in the precursor solution. The PEO crosslinkers used were a 4-arm star PEO (20 kDa) with 4 acrylates per PEO (PEO-tetra-acrylate, PEO-TA/PEG-TA), an 8-arm star PEO (20 kDa) with 8 acrylates per PEO (PEO-octa-acrylate, PEO-OA/PEG-OA), and a regular PEO-diacrylate (PEG-DA/PEG-DA) crosslinker (10 kDa) with 2 acrylates per PEO molecule. As shown in FIG. 6, the addition of 2% (w/v) of each crosslinker to the precursor solution resulted in an increase in the shear storage modulus, G'(Pa), upon completion of the free-radical photo-crosslinking reaction.

The plateau shear modulus values of hydrogels made of FibMA$_{0.4\%}$ formulations that included the various multi-functional PEO-acrylates were also compared to hydrogels formed using the respective crosslinking PEO alone, in order to ascertain the contribution of the FibMA to the polymer network's structural properties. The obtained data is presented in FIGS. 7A-B and 18A-E.

As shown in FIG. 7A, all three crosslinkers were able to form a gel network, with significantly lower storage modulus values as compared to their respective FibMA gel. The difference in modulus values between the two gels represents the contribution of the FibMA to the network formation. The PEO-TA demonstrated the largest difference in terms of the shear storage modulus of the two gels, suggesting a more idealized interaction between the FibMA and PEO-TA during the cross-linking reaction.

Additional data is presented in FIGS. 18A-C and show that during the crosslinking reaction, in all the tested formulations, the shear storage modulus of the hydrogels increased much more than the loss modulus (i.e., G'>>G"), indicating that the FibMA material behaves like an elastic gel.

The time for the hydrogels to reach 10, 50 and 90% of the G'$_{max}$ was calculated directly from the linear region of the time-sweep measurements of the G' curves. These values are presented respectively as t$_{10}$, t$_{50}$ and t$_{90}$ in FIG. 18D. The results show that the type of crosslinker also affected the polymerization reaction kinetics, indicating that the FibMA with PEG-TA provides the fastest reaction.

The propagation rates were also calculated directly from the slope of the G' curve and are presented in FIG. 18E. The results show that the propagation rate of FibMA with PEG-TA was more than two times higher than that of FibMA with PEG-DA, and 1.5 times higher than FibMA with PEG-OA.

The amount of crosslinker required to from the FibMA hydrogel was determined by combining the FibMA with a PEO crosslinker during the radical polymerization reaction while incrementally increasing the concentration of the crosslinker PEO-TA into the FibMA solution. The rheological properties of resultant gel after photopolymerization was characterized by oscillatory shear measurements. The plateau shear storage modulus was characterized for PEO-TA with and without FibMA$_{0.4\%}$ (5 mg/ml), starting from a concentration of 1.2% w/v, and increasing to 2% w/v, in 0.2% w/v increments. Below a concentration of 1.2% w/v, the FibMA$_{0.4\%}$ would not form an elastic gel and the G' was similar in value to G" (data not shown).

Consequently, as shown in FIGS. 19A-F show, PEG-TA alone was not able to from a polymeric network at a concentration of 1.2% w/v, while a PEG-TA hydrogel was able to form at 1.4% w/v.

The data presented in FIG. 8 and FIGS. 19G-H, show that while a linear increase in modulus as a function of concentration is seen for the PEO-TA hydrogel, a non-linear relationship can be seen for the FibMA-PEO-TA hydrogel. This disproportionate increase in the shear modulus with increasing concentrations of PEO-TA represents a synergistic effect in the hydrogel crosslinking between the PEO-TA and the FibMA.

The effect of the degree of conversion on the hydrogel formation was also investigated using time sweep oscillatory rheological measurements. Hydrogel precursors were polymerized on the rheometer and characterized for shear storage and loss modulus using two different FibMA formulations (FibMA$_{0.4\%}$ and FibMA$_{0.1\%}$, both with 2% w/v PEG-TA). These formulations were compared to hydrogels made from 2% w/v PEG-TA only.

The results are presented in FIGS. 20A-F and show that the degree of conversion had a significant effect on the hydrogel rheological properties. The FibMA$_{0.4\%}$ hydrogels exhibited the highest G'$_{max}$ of all the formulations. The kinetics of the free-radical polymerization, characterized by t$_{10}$, t$_{50}$ and t$_{90}$, were also affected by the degree of conversion of each formulation. The increasing degree of conversion facilitated improved reaction kinetics in the FibMA$_{0.4\%}$ hydrogels compared to the FibMA$_{0.1\%}$ formulation, and both FibMA formulations reacted faster than PEG-TA hydrogels. The propagation rate of the reaction, as measured from the slope of the G' curve, revealed the lowest rate for the FibMA$_{0.1\%}$ formulation and highest propagation for the FibMA$_{0.4\%}$ formulation, with PEG-TA exhibiting a rate in between the two.

The FibMA$_{0.2\%}$ solution at a concentration of 4% (w/v) was able to form a hydrogel network by photopolymerization without the addition of a polymeric crosslinker (see, FIG. 25). The maximum shear storage modulus of the hydrogels made from 40 mg/ml FibMA$_{0.2\%}$ was G'$_{max}$=231.6±16.95 Pa. The maximum shear loss modulus of the hydrogels made from 40 mg/ml FibMA$_{0.2\%}$ was G"$_{max}$=17.13±2.47 Pa.

The 4% (40 mg/ml) FibMA FibMA$_{0.2\%}$ solution features a high viscosity of 17.96±3.29 Pa·s (see, FIG. 26B).

A lower viscosity can be obtained with a concentration of FibMA lower than 1% w/w (lower than 10 mg/ml) (see, FIG. 26A). Hydrogel formation of such a solution is effected in the presence of a crosslinker (e.g., a polymeric crosslinker). The viscosity (Pa·s) of 10 mg/ml FibMA$_{0.2\%}$ and 1.5% PEG-TA was 3.173±0.079.

Differential Photocalorimetry (DPC):

Differential Photocalorimetry (DPC) studies were conducted to differentiate the degrees of methacrylation on the FibMA with respect to the free radical photopolymerization reaction. The DPC allows enthalpy changes in a material to be measured during and after exposure to light of certain wavelengths for different periods of time at different temperatures. UV-differential photocalorimetric experiments were performed on FibMA (FibMA$_{0.4\%}$) and FibMA0.5 (FibMA$_{0.2\%}$), using a Mettler Toledo Differential Scanning calorimeter (DSC), with a HSS7 sensor, a Hamamatsu LC8UV spot light source and cross-linking using UV light (365 nm, 5 mW/cm$^2$). In all experiments, the FibMA precursor solution containing all the constituents were tested and compared to an identical reference precursor solution that does not contain the photoinitiator (a reference solution). Unmodified (native) fibrinogen and PEO-TA were used as negative and positive controls, respectively.

The results are presented in FIGS. 9A-B and show that the enthalpy of the photopolymerization reaction was nearly two-fold higher for the FibMA (FibMA$_{0.4\%}$) when compared to the FibMA0.5 (FibMA$_{0.2\%}$), indicating that fewer methacrylate groups caused a reduction in the cross-linking reaction energy.

Swelling (Water Uptake):

The swelling characterization of the FibMA hydrogels was performed to determine the degree of crosslinking. The swelling experiments were conducted as follows: Each FibMA solution (8 mg/ml) containing different ratios of PEO-TA and 0.1 (w/v) % Irgacure2959 was gelled under UV light (365 nm with an intensity of 3.5 mW/cm$^2$) for 5 minutes in a Teflon mold (14.5 mm diameter, 5.0 mm height, 0.6 mL sample volume). The FibMA hydrogels were then immersed in PBS for 24 hours at 37° C., after which the swelling weight, Ws, was measured. The hydrogels were subsequently lyophilized to obtain their respective dry weight, Wd. The degree of swelling, Qt was calculated using the formula:

$$Qt=(Ws-Wd)/Ws*100\%.$$

The swelling results show that the FibMA gel can imbibe large amounts of water (up to 97% of its weight). Furthermore, there were no significant changes in the swelling ratios between the samples, suggesting that the very high water content of the gels make it inherently difficult to identify their degree of crosslinking using this methodology.

Table 2 below presents the degree of swelling (Qt) of different FibMA hydrogel formulations containing PEO-TA crosslinker.

TABLE 2

| Hydrogel | Qt (mean ± SD; n = 3)s |
|---|---|
| FibMA$_{0.4\%}$ + 2% PEO-TA | 97.13 ± 0.28 |
| FibMA$_{0.4\%}$ + 1.4% PEO-TA | 96.88 ± 0.30 |
| FibMA$_{0.2\%}$ + 2% PEO-TA | 96.99 ± 0.27 |
| FibMA$_{0.2\%}$ + 1.4% PEO-T | 97.42 ± 0.33 |

Proteolytic Degradation:

The biodegradation of the FibMA and PEG-TA hydrogels was evaluated experimentally using an in vitro degradation assay. For this purpose, the FibMA hydrogels and their respective precursor solutions were incubated in collagenase solutions of 0.1, 0.5, and 1 mg/mL in PBS for 48 hours at 37° C. The supernatant solution was thereafter evaluated by SDS polyacrylamide electrophoresis (SDS-PAGE), and the degradation byproducts were visualized using a coomassie brilliant blue staining (Thermo fisher Scientific, California, United States). The stained gels were digitally imaged and the results are presented in FIG. 10. As can be seen, the precursor solutions of fibrinogen and FibMA$_{0.4\%}$ generate different degradation fragments. The modification of fibrinogen chains with MAA groups, i.e., FibMA, led to a reduction in its susceptibility to the collagenase degradation, as indicated by the markedly fewer degradation fragments in the SDS-PAGE profiles of FibMA.

The control group for each sample show the SDS-PAGE profile of the protein without collagenase. The differences between the control and the collagenase incubated samples in the SDS-PAGE profiles was markedly different for the FibMA and the fibrinogen treatments. Consequently, the control group contains only protein precursors, but these undergo a protein reduction step during the SDS-PAGE processing.

The results further demonstrate a significant difference between the fragments of the FibMA precursor solution (center panel) and FibMA hydrogels (right panel). The degradation of the cross-linked FibMA hydrogels shows the smallest number of degradation fragments.

Taken together, these results indicate that the fibrinogen methacrylation causes a marked reduction in the protease susceptibility of the protein.

Example 3

Tissue Culture Assay

The FibMA hydrogels described herein can be used, inter alia, as a matrix for cell delivery, or as a bioink for 3D bioprinting. In these capacities, the encapsulating FibMA hydrogel provides the cells with the basic bioactive motifs required for cell survival.

The biocompatibility of the FibMA hydrogels was therefore tested by encapsulating cells within the hydrogel during the photopolymerization reaction and culturing the cells in 3D for up to three weeks.

The cells were grown in a FibMA hydrogel for a number of days or weeks and then visualized within the hydrogel using fluorescence and phase contrast microscopy (see, FIG. 11). Additional bioactivity can be introduced into the matrix for stimulating cell differentiation and proliferation.

A live/dead assay was used to examine the biocompatibility of the FibMA hydrogel as an encapsulating hydrogel. This assay takes cells suspended in the hydrogel precursor solution, encapsulates these cells in the hydrogel during the photopolymerization, and documents the cell survival over several days in 3D culture. Neonatal human dermal fibroblast (NHDF) were cultured in the FibMA for up to 8 days. The viability was confirmed by a Calcein/Ethidium Live/Dead assay, as described herein.

NHDF cells were cultured in $FibMA_{0.2\%}$ hydrogels made with 1.6% w/v PEG-TA ($G'_{max}$=443±4.77 Pa and $G''_{max}$=1.38±0.31 Pa). Cells were also cultured in $FibMA_{0.1\%}$ made with 1.8% w/v PEG-TA ($G'_{max}$=377±3.6 Pa and $G''_{max}$=1.3±0.15 Pa). Hydrogels made from only PEG-TA, 2.5% w/v, containing NHDF cells were also tested ($G'_{max}$=432±2.7 Pa and $G''_{max}$=0.78±0.11 Pa, similarly to the FibMA hydrogels).

As shown in FIG. 12 and FIGS. 21A-B, live/dead staining indicated that cells in all tested materials displayed high viability green staining over the entire period of cultivation, and only very few dead cells (red stained) were observed. Most the cells in the hydrogel remained rounded during the 8 days, and a few cells were observed forming cellular extensions in the matrix. NHDF cells were viable in the $FibMA_{0.2\%}$ and $FibMA_{0.1\%}$ hydrogels for up to 21 days, whereas the PEG-TA hydrogels did not support the viability of the cells over the same time. The number of spread cells and the cells that could establish cell-cell contacts was increase in the $FibMA_{0.1\%}$ hydrogels, when compared with $FibMA_{0.4\%}$ and $FibMA_{0.2\%}$ hydrogels.

Quantification of the cell viability in the hydrogels was done by counting live cells and comparing to the total number of cells in the construct, and the results are presented in FIG. 21C. These data were normalized to the percent of viable cells observed on day 1. The cell viability was greater than 90% at day 21 in both the $FibMA_{0.2\%}$ and $FibMA_{0.1\%}$ hydrogels, whereas the PEG-TA hydrogels exhibited a significantly lower viability of 45% at the same time point ($p<0.01$, $n\geq3$).

The CCK-8 assay results, presented in FIG. 21D, indicated a similar trend, with an increase in the normalized optical density (OD) value of the $FibMA_{0.1\%}$ and $FibMA_{0.2\%}$ over the 7 days of in vitro culture, and a significant reducing in the OD for the PEG-TA at the same time-point ($p<0.001$, $n\geq3$). Consequently, the OD of the PEG-TA already decreased to half the initial value by day 3, confirming the observed poor viability in the PEG-TA hydrogels. Cell viability was also visualized on the surface of the FibMA and PEG-TA hydrogels.

FIG. 21E shows the elongated morphology of the NHDF cells on the surface of $FibMA_{0.2\%}$ and $FibMA_{0.1\%}$ hydrogels, and rounded morphologies of the cells on the surface of the PEG-TA hydrogels. These results, which underscore the ability of the cells to form cell adhesions with the FibMA surface in 2D culture, were also observed on the $FibMA_{0.4\%}$ and $FibMA_{0.05\%}$ formulations (data not shown).

Some prior studies have shown that the addition of Polyethylene oxide (PEO, 10 kDa) as a porogen that can lead to the formation of highly interconnected and hierarchical pores structures within a dense hydrogel matrix. The addition of PEO was examined with FibMA hydrogels, in order to evaluate if the porogen can improve the formation of cellular extensions within the encapsulating hydrogels.

An additional FibMA formulation of the hydrogel was prepared for this purpose using 0.8% PEO with FibMA0.25 pre-gel solutions. Cells cultivated in these hydrogels did not show any enhanced propensity for the formation of cellular interconnections or extensions, when compared to the control FibMA hydrogels. Most of the cells encapsulated in FibMA0.25/PEO hydrogels remained round (see, FIG. 12).

In general, the results from the cell encapsulation studies reveal that the FibMA hydrogels are highly biocompatible as indicated by the high degree of cell viability observed within the network after 8 days. Although most of the cells are rounded in the FibMA ($FibMA_{0.4\%}$) hydrogel, there are a few cells that begin to form extensions in the FibMA0.25 ($FibMA_{0.1\%}$) hydrogel, indicating that the process of proteolytic degradation of this formulation has begun at this timepoint. Assuming that the degree of methacrylation of the fibrinogen is somehow correlated to the resistance of the material to proteolytic degradation, one can expect that further proteolysis can be achieved with lower methacrylated fibrinogen formulations. Additional culture time may also promote further cell-mediated proteolysis of the FibMA matrix, resulting is higher degree of cell spreading and cellular network formations within the matrix. Taken together, the results suggest that control over proteolytic cellular remodeling can be accomplished by controlling the degree of methacrylation of the fibrinogen material.

To test this, NHDFs were cultured in the FibMA0.25 ($FibMA_{0.1\%}$) hydrogels for extended durations in order to correlate between the formation of cellular extensions within the matrix and the proteolytic degradation that may occur over extended culture times. The extended culture time lasted 20 days and the viability results from this study, shown in FIG. 13A, showed high viability throughout the extended culture duration. Some of the cells can be seen forming extension in the FibMA0.25 ($FibMA_{0.1\%}$) matrix as early as day 5. The number of cells forming cellular extensions increases with time, but even after 20 days in culture, many of the NDFs are still rounded in this material. The viability of NHDF cells ($3\times10^6$ cells/ml) cultures in a hydrogel formed of 40 mg/ml $FibMA_{0.2\%}$ without a crosslinking agent has also been demonstrated (FIG. 13B).

A different cell type was also encapsulated in the FibMA hydrogels, namely the C2C12 muscle progenitor cell line. These cells are considered more challenging to 3D culture in encapsulating hydrogels and were entrapped in the FibMA ($FibMA_{0.4\%}$) hydrogel scaffold upon photopolymerization. The C2C12 cells ($8^{th}$ passage) were suspended in FibMA hydrogel precursor at a cell concentration of $6\times10^6$ cells/ml and cultured for up to 10 days after gelation. The FibMA formulation was supplemented with 1.6% w/v PEO-TA to form a hydrogel with shear modulus of G'=520±4.86 Pa, and G''=2.13±0.16 Pa. Control hydrogels containing C2C12 cells were produced from PEO-TA 3% (w/v) alone, such that the shear modulus of the hydrogels was similar to the FibMA hydrogel treatment (G'=503±6.6 Pa, and G''=1.51±0.09 Pa). The results are presented in FIG. 14 and indicated that the C2C12 were highly viable in the FibMA hydrogel for up to 10 days, whereas the PEO-TA hydrogels did not maintain the high cellular viability. The C2C12 cells remain rounded in the FibMA matrix during the entire duration of the culture period, suggesting that the proteolytic degradation of the matrix may be hindering the formation of lamellipodia.

A tissue growth assay called the gel-in-gel assay was also conducted, where cellular construct beads were made to resemble tissues that can invade an acellular FibMA hydrogel encapsulating them. The tissue beads are encapsulated by the acellular FibMA matrix by UV light photopolymerization. The gel-in-gel system is cultured for up to one week under standard tissue culture conditions. The chemotactic invasion of cells from the beads into the encapsulating FibMA matrix is measured morphometrically. The cell invasion assay was performed using MDA-MB-231 cancer cell lines and NDHFs, both cultivated in the tissue construct beads. The MDA-MB-231 and NHDF cells are pre-labeled with fluorescence markers for mCherry and GFP, respectively. These beads are then placed inside FibMA hydrogels as illustrated in FIG. 15. The fluorescence tissue constructs are placed in 300 μl of FibMA precursor solution (with photoinitiator) in a 48-well plate and exposed to UV light for 5 minutes. Cellular invasion from the tissue beads to the FibMA matrix was visualized by fluorescence microscopy for up to 6 days.

The results from the gel-in-gel assay are shown in FIG. 16 and reveal that the predominant cell invasion into the FibMA matrix was from the MDA-MB-231 cancer cell line (red). The NHDFs (green) were mostly confined to the initial round boundaries of the tissue construct beads at day 3, suggesting that their invasion into the FibMA was less efficient. By day 6, more NHDFs were seen invading the FibMA matrix. The fact that the predominant invasion observed was by the cancer cells is consistent with the notion that cancer cells do not require proteolytic degradation to invade soft tissues. These results indicate that the resistance of the FibMA matrix to proteolysis because of the high degree of fibrinogen methacrylation hinders that mesenchymal invasion of the NHDFs, but not the ameboid invasion of the MDA-MB-231 cells.

Such preferential invasion can also be used to design cell diagnostic assays that require sorting of cell types based on their primary mechanism of migration and invasion.

Example 4

In Vivo Biodegradation Study

An in vivo biodegradation study involved the subcutaneous implantation of gadolinium-labeled FibMA hydrogels, followed by MRI analysis of the hydrogel biodegradation. Synthesis of FibMA-Gadolinium-Diethylenetriaminepentaacetic Acid (FibMA-GdDTPA):

FibMA-Gadolinium-Diethylenetriaminepentaacetic Acid, FibMA-GdDTPA, was prepared in a two-step reaction, in accordance with a previously described procedure [Berdichevski et al. *Proc. Natl. Acad. Sci. U.S.A.* 112, 5147-5152 (2015)]. Briefly, DTPA dianhydride (Sigma-Aldrich, Steinheim, Germany) was dissolved in anhydrous dimethyl sulfoxide (90 mg/mL) and added gradually to 10 mL of FibMA (pH 8.8, 9 mg/mL). The pH was constantly adjusted to 8.5 using 5M NaOH during the course of adding the DTPA. The reaction mixture was stirred for 2 hours at room temperature. The intermediate FibMA-DTPA product was purified by dialysis against 1M PBS for 24 hours at 4° C. Next, the purified FibMA-DTPA was adjusted to pH 6.5. Gadolinium (III) chloride hexahydrate (Sigma-Aldrich, Steinheim, Germany) was dissolved in PBS and added to the FibMA-DTPA solution. The reaction solution was stirred for 24 hours at 4° C. The final product (FibMA-GdDTPA) was purified by dialysis against PBS for 3 days. The product was stored at −80° C. for up to 1 month before use.

In vitro MRI was performed on a 9.4 T scanner (Bruker Biospec, Ettlingen, Germany), using a transmit/receive cylindrical volume coil (86 mm diameter). T1 maps were acquired using a Rapid Acquisition with Relaxation Enhancement (RARE) pulse sequence with variable repetition time. TR=100, 200, 300, 400, 500, 600, 800, 1000, 1500, 2000, 3000, 4000, 5000, 6000, 8000, [ms]; TE=25 ms; RARE factor=8; 2.5 mm slice thickness; 250 μm in plane resolution; field of view (FOV)=4.8×4.0 cm$^2$; matrix size=192×160; and scan time=about 10 minutes. T1-map images were calculated by performing exponential curve fitting for each pixel using a custom-build software in Matlab (MathWorks, MA). R1 values were calculated from T1 values by R1=1/T1. Table 3 below summarizes the relaxation time T1 and relaxation rate R1.

TABLE 3

| Plug number | FibMA$_{0.1\%}$ Gd-DTPA (mg/ml) | FibMA$_{0.1\%}$ (mg/ml) | PEG-TA % | T1 (ms) | R1 (ms$^{-1}$) |
|---|---|---|---|---|---|
| 1 | 0 | 8 | 1.5 | 2866 | 0.349 |
| 2 | 1 | 7 | 1.5 | 1964 | 0.509 |
| 3 | 1.5 | 6.5 | 1.5 | 1681 | 0.595 |
| 4 | 2 | 6 | 1.5 | 1484 | 0.674 |
| 5 | 2.5 | 5.5 | 1.5 | 1319 | 0.758 |
| 6 | 3 | 5 | 1.5 | 1257 | 0.796 |

FIGS. 22A-B present a graphical representation of the obtained calibration data. An optimal concentration of FibMA$_{0.1\%}$-GdDTPA (2 mg/ml) was identified using this in vitro MRI calibration. The 2 mg/ml Gd-labelled material showed T1 value which allowed to distinguish between the Gd-labelled hydrogel constructs and the surrounding aqueous environment, as seen in rectangle #5 in FIG. 22A.

The exemplary formulation was then used to prepare the constructs for in vivo imaging.

In vivo MRI was performed using a 1 T micro-MRI (Aspect M2, Aspect Imaging, Israel), equipped with a cylindrical radiofrequency volume coil (35 mm inner diameter) for signal excitation and reception. The animals were under anesthesia prior to imaging using 0.5-1.5% isoflurane, supplemented with oxygen (0.8 L/minute). Respiration was monitored using an Aspect M2 (Aspect Imaging, Israel). The T1-weighted images were acquired for each animal using: GRE-SP (Gradient Echo) sequence with slice thickness=1 mm, FOV=6.4×6.4 cm, matrix dimension=128×128, repetition/echo time (TR/TE)=12.6/3.2 ms, 30° pulse, number of excitations=4.

The experiments were performed using a 1 T micro-MRI (Aspect M2, Aspect Imaging, Israel) with 5-mm cylindrical hydrogel constructs made from 60 μl solution containing FibMA$_{0.1\%}$ (6 mg/ml), FibMA$_{0.1\%}$-GdDTPA (2 mg/ml) and 1.5% w/v PEG-TA (G'$_{max}$=331.8±13.15, G"$_{max}$=1.1±0.1). The hydrogels were implanted in C57BL/6 mice in dorsal subcutaneous pockets created as described herein. The MR images were acquired immediately after the implantation and weekly for up to 8 weeks.

FIGS. 23A-I show the plugs still visible eight weeks post-implantation. Quantitative analysis of the MR images, as seen in FIG. 23J, showed a progressive degradation of the implant volume from week to week. By the third week after implantation, there was a significant reduction in the initial implant volume (p<0.05, n=3). At the eighth week post-implantation, the implant size was reduced by nearly 50% of its initial volume (p<0.01, n=3).

Histological samples stained with H&E also demonstrated the in vivo biodegradation of the FibMA hydrogels during the 8-week implantation. After 1 week, the samples remained intact with inflammatory invasion observed only at the periphery of the hydrogel implant (FIG. 24A). By the third week, the FibMA hydrogels were invaded by inflammatory cells almost throughout (FIG. 24B). After the eighth week, the inflammatory infiltrate was somewhat reduced with much of the hydrogel cleared from the implant site (FIG. 24C). Remnants of the inflammatory process were still visible after 8 weeks along with smaller fragments of hydrogel being cleared from the implant locale.

Example 5

Intermediate Concluding Remarks

One of the currently available curable biological materials that is frequently used in bioprinting and other methods of scaffold formations is gelatin methacrylate (GelMA). Table 4 below summarized the advantageous features of the exemplary curable, hydrogel forming, precursor (conjugate) of the present embodiments, fibrinogen methacrylate (FibMA) over GelMA.

TABLE 4

| | GelMA | FibMA |
| --- | --- | --- |
| Sources of the native protein | The gelatin is made by the partial hydrolysis of denatured collagen. The main sources of this collagen is pig, bovine or fish. | The fibrinogen is obtained from human blood plasma. It can be purified from a patient's own blood (autologous), or it can be derived from pooled blood samples (allogeneic). |
| | The average molecular weight (MW) of the gelatin is highly variable, and can range between 15000 and 400000 Daltons. The MW depends on several factors, including the origins of the raw materials, the pretreatment methods and the hydrolytic processing parameters (e.g., the pH, temperature and time). This high variability in the raw protein makes the final properties of the GelMA highly variable in terms of degree of substitution, mechanics, etc. | The average molecular weight of fibrinogen is 340 kDa. There is no variability in the MW of this protein so that the final properties of the FibMA are highly consistent and not variable from batch to batch. |
| | There are three types of hydrolytic processes of collagen: physical, chemical and enzymatic. Each one contains 3 stages: pretreatment of the raw materials, extraction of gelatin and purification. | Fibrinogen is typically isolated from blood plasma using a few possible precipitation techniques, e.g., cryo-precipitation, ammonium sulphate precipitation. |
| Bio-ink | GelMA can undergo chemical crosslinking by light-activated radical polymerization after injection from the printer head. The degree of the cross-linking will be dependent on the properties of the GelMA, which are highly variable (see above). Therefore the final printed product has highly inconsistent properties. | FibMA can be chemically crosslinked by light-activated radical polymerization after injection from the printer head. The degree of crosslinking depends on the properties of the FibMA, which are very consistent (see above). Therefore, the final printed product should have very reliable and reproducible properties. |
| | GelMA, like gelatin, can also undergo a sol-gel transition from high temperature to low temperature. The extent of this behavior depends on the degree of methacrylation. Therefore, the printability of GelMA dictates usage of a printer with a feature of precise control over the temperature of the nozzle. | FibMA has no sol-gel transition temperature. Therefor it does not undergo phase transitions in the printing apparatus. Any simple printer can accommodate the FibMA as a bioink. |
| Matrix for tissue repair | GelMA is not expected to be approved for use in human patients because it is derived from denatured animal tissue. It is purely an experimental substrate for R&D use only. | FibMA is designed for use in human clinical applications. There are no constraints to FDA approval (or CE-mark) of FibMA because all raw materials are human-derived and predicated for use in humans. |

As demonstrated herein, unlike the methacrylation reaction of gelatin, the fibrinogen methacrylation required a denaturation in 8M urea to unravel the tertiary structure of the protein, thereby exposing primary amines on the lysine residues to the MAA reaction. Upon completion of the reaction, the urea was removed by dialysis against PBS. In the absence of the urea during the reaction, the methacrylation resulted in an insoluble protein when reconstituted in PBS (not shown). The extent of fibrinogen methacrylation, as verified by $^1$H-NMR, was controlled using stoichiometric reaction conditions with constant temperature and duration. The number of methacrylate groups on the final fibrinogen product was determined to be proportional to the molar ratio of MAA to fibrinogen in the reaction (see, Table 1).

The formation of a hydrogel from the soluble FibMA product was verified by in situ rheological characterization. Photopolymerization rheometery measures loss and storage moduli of the hydrogel during its polymerization reaction by light-activated chemistry. The results indicated that the FibMA can form a gel network when a reactive crosslinker is included in the hydrogel precursor solution. The formation of a polymer gel network in a solution of below 8 mg/ml FibMA was evident only when a minimum of 1.2% w/v PEG-TA (20 kDa) was present in the solution. At a concentration of 40 mg/ml, a hydrogel is formed (e.g., using the FibMA$_{0.2\%}$ conjugate) also in the absence of a reactive cross-linker.

The FibMA hydrogels were evaluated for their ability to enable 3D cell culture in their capacity as potential carriers for cells therapy, scaffold for tissue engineering and bio-inks for bioprinting. Upon encapsulation in the FibMA hydrogels during photopolymerization, the cells become entrapped in a dense, amorphous polymer network that has formed around them. The cells remain highly viable (above 90%) over the course of three weeks in culture within the FibMA hydrogels, whereas PEG-TA control hydrogels exhibit a significantly reduce viability of the cells (below 50% after 21 days) (FIGS. 21A-D). The indispensability of bioactive domains on the fibrinogen backbone of the FibMA is evidenced by the significant difference in viability between the two treatments. Although the cells are metabolically active in the FibMA hydrogels, they remain rounded in 3D culture in the hydrogel matrix. The morphology of the encapsulated cells is mostly rounded even after 21 days, and not affected by the DC of the FibMA. In contrast, cells growing on the surface of the FibMA hydrogel form elongated morphologies and exhibit formation of multicellular networks after 21 days in culture (FIG. 21E).

These different morphological patterns of the cells within and on the surface of the FibMA hydrogels may be explained, e.g., by the confining effects of a hydrogel with limited proteolytic degradability. Furthermore, in the 40 mg/ml FibMA$_{0.2\%}$ hydrogels, the cells were able to from extensions and become spread in 3D within the network (FIG. 13B).

The proteolytic degradation of the FibMA hydrogels was tested by an in vitro assay that employs bacterial collagenase in solution. SDS-PAGE results from this assay confirmed that FibMA hydrogels, when incubated in the collagenase solution, exhibited limited proteolysis, whereas the FibMA precursor solution was more readily degraded by the collagenase in solution. The limited degradation may be attributed to a high degree of crosslinking of the FibMA hydrogels, which would purportedly limit proteolytic infiltration and reduce acceptability of proteases to the degradation sites on the fibrinogen backbone. Another factor required for mesenchymal migration into the matrix is cell adhesion, and for this reason one could not preclude that limited accessibility to cell adhesion sites on the FibMA backbone could be reducing cell invasion in the matrix. However, the FibMA supports cell adhesion in 2D culture, suggesting that limited cell invasion in 3D culture is due to reduced proteolysis.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A conjugate comprising fibrinogen and a plurality of curable groups that can undergo polymerization, entanglement and/or cross-linking when exposed to a curing condition covalently attached to the fibrinogen, the conjugate being devoid of a polymeric moiety, wherein the fibrinogen is denatured fibrinogen.

2. The conjugate of claim 1, wherein at least a portion, or all, of the curable groups are photopolymerizable groups.

3. The conjugate of claim 1, wherein at least a portion, or all, of the curable groups are (meth)acrylic groups.

4. The conjugate of claim 1, wherein at least a portion, or all, of the curable groups are attached to lysine residues of the fibrinogen.

5. The conjugate of claim 4, wherein said curable groups are attached to 10 to 100% of the lysine residues of the fibrinogen.

6. The conjugate of claim 1, further comprising a labeling agent covalently attached thereto.

7. A process of preparing the conjugate of claim 1, the process comprising coupling a compound that features at least one curable group and at least one reactive group to the fibrinogen under conditions that promote formation of a covalent bond between said reactive group and a chemically compatible reactive group of the fibrinogen.

8. A curable formulation comprising the conjugate of claim 1 and a carrier, the conjugate comprising fibrinogen and a plurality of curable groups that can undergo polymerization, entanglement and/or cross-linking when exposed to a curing condition covalently attached to the fibrinogen, the conjugate being devoid of a polymeric moiety, wherein the fibrinogen is denatured fibrinogen.

9. The curable formulation of claim 8, wherein said carrier is an aqueous carrier.

10. The curable formulation of claim 9, wherein a concentration of the conjugate in the formulation ranges from 1 to 500, or from 1 to 20, or from 5 to 20, mg/mL.

11. The curable formulation of claim 8, wherein said curable groups are photopolymerizable groups, the curable formulation further comprising a photoinitiator.

12. The curable formulation of claim 8, further comprising a cross-linking agent.

13. The curable formulation of claim 12, wherein an amount of said cross-linking agent ranges from 0.5 to 10% by weight of the total weight of the formulation.

14. The curable formulation of claim 8, further comprising a biological material other than said fibrinogen.

15. The curable formulation of claim 14, wherein said biological material comprises cells.

* * * * *